United States Patent
Chen et al.

(10) Patent No.: US 12,129,478 B1
(45) Date of Patent: Oct. 29, 2024

(54) ENGINEERED ADENOSINE DEAMINASES AND BASE EDITORS THEREOF

(71) Applicant: Lumiere Therapeutics Co., Ltd., Jiangsu (CN)

(72) Inventors: Bohong Chen, Guangzhou (CN); Yang Hu, Guangzhou (CN); Yulin Yu, Guangzhou (CN); Shaoyun Lin, Guangzhou (CN); Wenqiong Tan, Guangzhou (CN)

(73) Assignee: Lumiere Therapeutics Co., Ltd., Jiangsu (CN)

( * ) Notice: Subject to any disclaimer, the term of this patent is extended or adjusted under 35 U.S.C. 154(b) by 0 days.

(21) Appl. No.: 18/457,276

(22) Filed: Aug. 28, 2023

(30) Foreign Application Priority Data

Jun. 28, 2023 (CN) .......................... 202310776962.5

(51) Int. Cl.
| | | |
|---|---|---|
| *C12N 15/90* | (2006.01) | |
| *C12N 5/071* | (2010.01) | |
| *C12N 9/22* | (2006.01) | |
| *C12N 9/78* | (2006.01) | |
| *C12N 15/11* | (2006.01) | |
| *C12N 15/85* | (2006.01) | |

(52) U.S. Cl.
CPC ........... *C12N 15/90* (2013.01); *C12N 5/0686* (2013.01); *C12N 9/22* (2013.01); *C12N 9/78* (2013.01); *C12N 15/11* (2013.01); *C12N 15/85* (2013.01); *C12Y 305/04004* (2013.01); *C12Y 305/04005* (2013.01); *C12N 2310/20* (2017.05); *C12N 2800/107* (2013.01)

(58) Field of Classification Search
None
See application file for complete search history.

(56) References Cited

U.S. PATENT DOCUMENTS

| | | | |
|---|---|---|---|
| 2022/0348894 A1* | 11/2022 | Bowen | C12N 9/78 |
| 2023/0140953 A1* | 5/2023 | Slaymaker | C12N 15/102 424/94.6 |
| 2024/0076652 A1* | 3/2024 | Liu | A61P 43/00 |

OTHER PUBLICATIONS

TRNA adenosine(34) deaminase TadA [*Mangrovibacter* sp. MFB070] NCBI Reference Sequence: WP_036116397.1, Genbank, Jul. 5, 2022, 1 page.
TRNA adenosine(34) deaminase TadA [*Zophobihabitans entericus*] NCBI Reference Sequence: WP_166917507.1, Genbank, Jul. 5, 2022, 2 pages.
TRNA adenosine(34) deaminase TadA [*Erwinia* sp. 198] NCBI Reference Sequence: WP_125289504.1, Genbank, Jul. 5, 2022, 2 pages.

* cited by examiner

*Primary Examiner* — Neil P Hammell
*Assistant Examiner* — Khaleda B Hasan
(74) *Attorney, Agent, or Firm* — Sheppard, Mullin, Richter & Hampton LLP

(57) ABSTRACT

Disclosed are adenosine deaminases, base editors comprising the adenosine deaminases and complexes comprising the base editors. The adenosine deaminases and the base editors exhibited superior adenine editing effects and achieved A·T base pair to G·C base pair transformation at DNA level.

21 Claims, 32 Drawing Sheets
Specification includes a Sequence Listing.

FIG. 1A

| Arabinose Con. | 0 nM | 20 nM | 40 nM |
|---|---|---|---|
| dCas9 control | 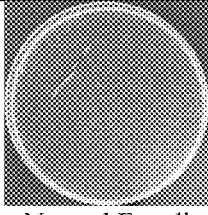 Normal E. coli growth. Bacterial colonies grew evenly throughout the plate. | 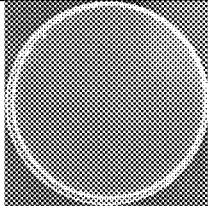 No E. coli growth | 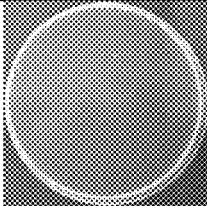 No E. coli growth |
| TadA-8e-dCas9 | 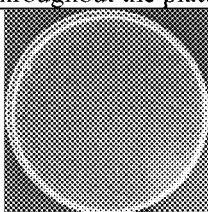 Normal E. coli growth. Bacterial colonies grew evenly throughout the plate. | 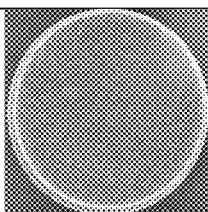 Normal E. coli growth. Bacterial colonies grew evenly throughout the plate. | 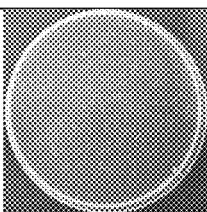 Normal E. coli growth. Bacterial colonies grew evenly throughout the plate. |
| MaTadA-WT-dCas9 | 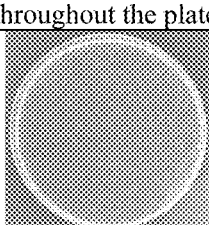 Normal E. coli growth. Bacterial colonies grew evenly throughout the plate. | 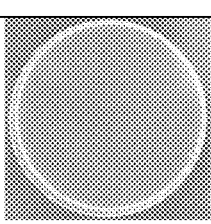 No E. coli growth | 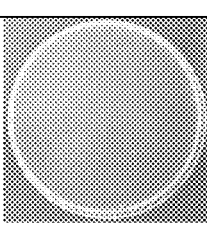 No E. coli growth |
| MaTadA1.0-dCas9 | 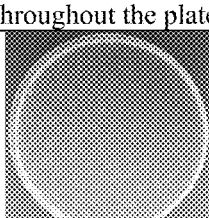 Normal E. coli growth. Bacterial colonies grew evenly throughout the plate. | 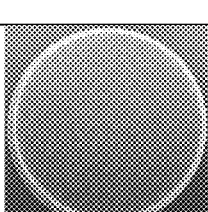 Normal E. coli growth. Bacterial colonies grew evenly throughout the plate. | 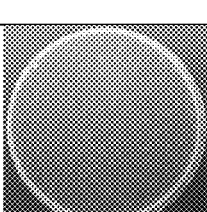 E. coli growth but with fewer colonies and lower density |

FIG. 1B

| Arabinose Con. | 0 nM | 20 nM | 40 nM |
|---|---|---|---|
| ZoTadA-WT-dCas9 | Normal E. coli growth Bacterial colonies grew evenly throughout the plate. | No E. coli growth | No E. coli growth |
| ZoTadA1.0-dCas9 | Normal E. coli growth Bacterial colonies grew evenly throughout the plate. | Normal E. coli growth Bacterial colonies grew evenly throughout the plate. | Normal E. coli growth Bacterial colonies grew evenly throughout the plate. |
| ErTadA-WT-dCas9 | Normal E. coli growth Bacterial colonies grew evenly throughout the plate. | No E. coli growth | No E. coli growth |
| ErTadA1.0-dCas9 | Normal E. coli growth Bacterial colonies grew evenly throughout the plate. | Normal E. coli growth Bacterial colonies grew evenly throughout the plate. | with E. coli growth but with fewer colonies and lower density |

FIG. 1C

| Arabinose Con. | 0 nM | 20 nM | 40 nM |
|---|---|---|---|
| MaTadA1.1-dCas9 | 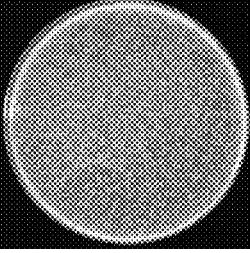<br>Normal E. coli growth<br>Bacterial colonies grew evenly throughout the plate. | 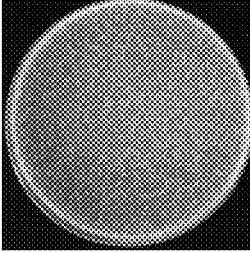<br>Normal E. coli growth<br>Bacterial colonies grew evenly throughout the plate. | 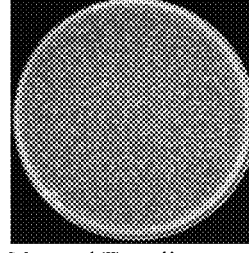<br>Normal E. coli growth<br>Bacterial colonies grew evenly throughout the plate. |
| MaTadA1.2-dCas9 | 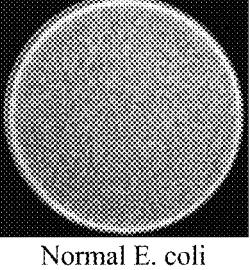<br>Normal E. coli growth<br>Bacterial colonies grew evenly throughout the plate. | 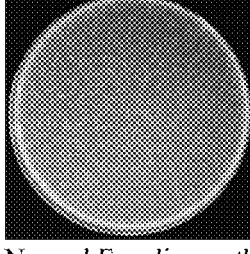<br>Normal E. coli growth<br>Bacterial colonies grew evenly throughout the plate. | 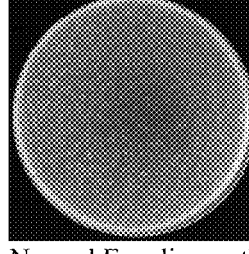<br>Normal E. coli growth<br>Bacterial colonies grew evenly throughout the plate. |
| MaTadA1.3-dCas9 | 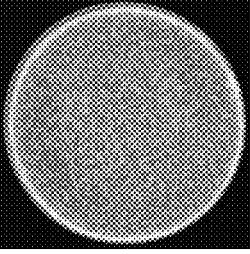<br>Normal E. coli growth<br>Bacterial colonies grew evenly throughout the plate. | 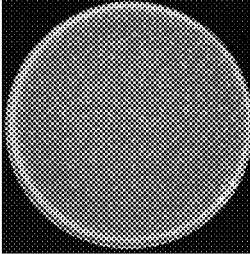<br>Normal E. coli growth<br>Bacterial colonies grew evenly throughout the plate. | 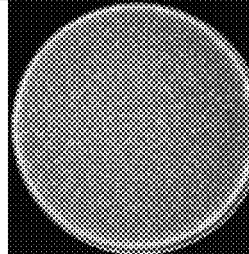<br>Normal E. coli growth<br>Bacterial colonies grew evenly throughout the plate. |

FIG. 1D

| Arabinose Con. | 0 nM | 20 nM | 40 nM |
|---|---|---|---|
| MaTadA1.4-dCas9 | 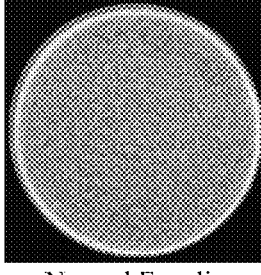 Normal E. coli growth Bacterial colonies grew evenly throughout the plate. | 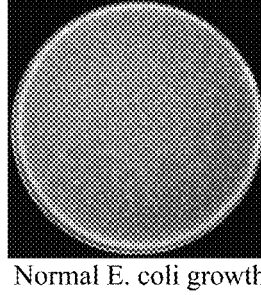 Normal E. coli growth Bacterial colonies grew evenly throughout the plate. | 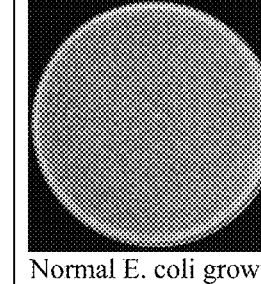 Normal E. coli growth Bacterial colonies grew evenly throughout the plate. |
| MaTadA1.5-dCas9 | 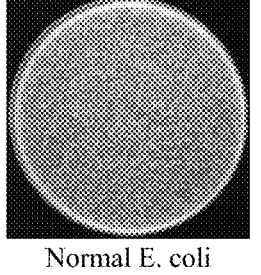 Normal E. coli growth Bacterial colonies grew evenly throughout the plate. | 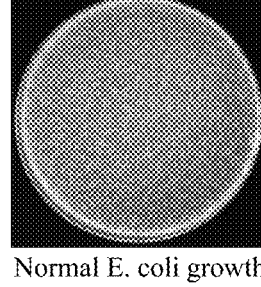 Normal E. coli growth Bacterial colonies grew evenly throughout the plate. | 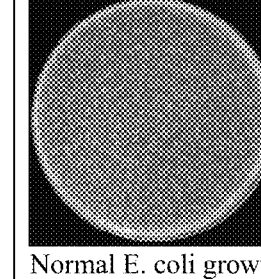 Normal E. coli growth Bacterial colonies grew evenly throughout the plate. |

FIG. 2

| Arabinose Con. | 0 nM | 20 nM | 40 nM |
|---|---|---|---|
| dCas9 control | 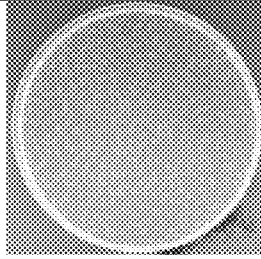 Normal E. coli growth Bacterial colonies grew evenly throughout the plate. | 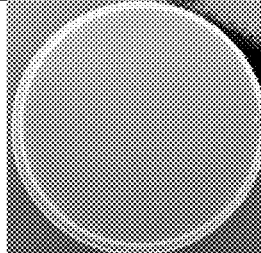 No E. coli growth | 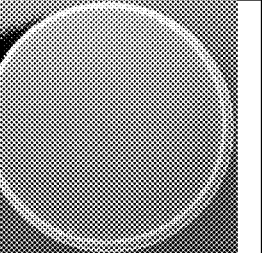 No E. coli growth |
| TadA-8e-dCas9 | 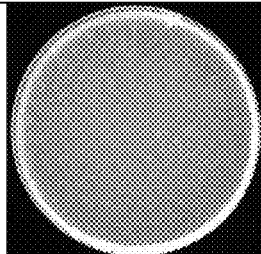 Normal E. coli growth Bacterial colonies grew evenly throughout the plate. | 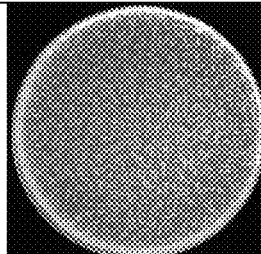 Normal E. coli growth Bacterial colonies grew evenly throughout the plate. | 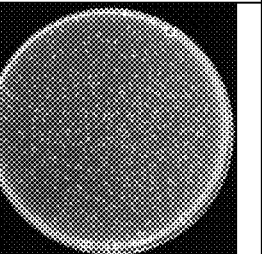 Normal E. coli growth Bacterial colonies grew evenly throughout the plate. |
| MaTadA-WT-dCas9 | 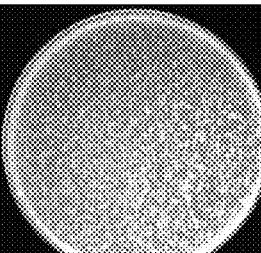 Normal E. coli growth Bacterial colonies grew evenly throughout the plate. | 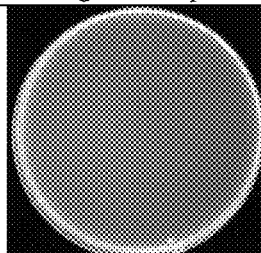 No E. coli growth | 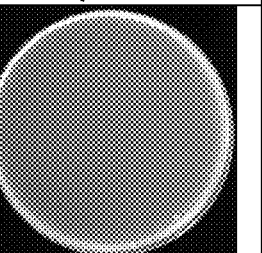 No E. coli growth |
| MaTadA1.0-dCas9 | 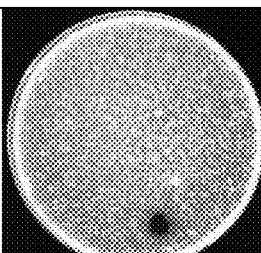 Normal E. coli growth Bacterial colonies grew evenly throughout the plate. | 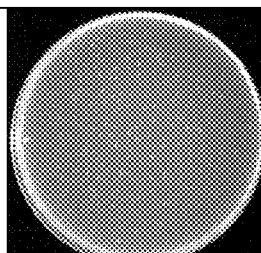 with E. coli growth but with fewer colonies and lower density | 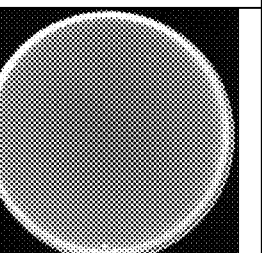 with E. coli growth but with least colonies and lowest density |

FIG. 3A

| | | |
|---|---|---|
| dCas9 control | [sequencing trace image] (No Editing) 5'-CTGCATTTATGTCAGACTTG-3' (SEQ ID NO: 42) | SEQ ID NO: 55<br>SEQ ID NO: 56<br>SEQ ID NO: 76<br><br>SEQ ID NO: 55<br>SEQ ID NO: 55 |
| TadA-8e-dCas9 | [sequencing trace image] High Editing Efficiency. Red A5 (position 5 from 5' end of SEQ ID NO: 42) and A9 (position 9 from 5' end of SEQ ID NO: 42) peaks were edited to blue G peaks. | SEQ ID NO: 55<br>SEQ ID NO: 56<br>SEQ ID NO: 76<br><br>SEQ ID NO: 55<br>SEQ ID NO: 57 |
| MaTadA 1.0-dCas9 | [sequencing trace image] Editing Competent with overlapping peaks. Red A5 peak was edited to blue G peak. A9 peak was partly edited to G peak, resulting in overlapping peaks at this position. | SEQ ID NO: 55<br>SEQ ID NO: 56<br>SEQ ID NO: 73<br><br>SEQ ID NO: 55<br>SEQ ID NO: 58 |
| ZoTadA1 .0-dCas9 | [sequencing trace image] Editing Competent with overlapping peaks. A5 peak was partly edited to G peak, resulting in overlapping peaks at this position. A9 peak was not edited. | SEQ ID NO: 59<br>SEQ ID NO: 83<br>SEQ ID NO: 73<br><br>SEQ ID NO: 59<br>SEQ ID NO: 59 |
| ErTadA1 .0-dCas9 | [sequencing trace image] Editing Competent with overlapping peaks. A5 peak was partly edited to G peak, resulting in overlapping peaks at this position. A9 peak was not edited. | SEQ ID NO: 55<br>SEQ ID NO: 56<br>SEQ ID NO: 73<br><br>SEQ ID NO: 55<br>SEQ ID NO: 60 |

FIG. 3B

| | | |
|---|---|---|
| dCas9 control | GGACGCGTACACCCCAAGTCTGACATAAATgcagtttaaggttt<br>CCTGCGCATGTGGGGTTCAGACTGTATTTAcgtcaaattccaaa<br>　　　　　　　　　　　　　　　　　　　　1　　　　5<br>　　　　　　　　　　　　　　　　　　　M Q F K V<br>　　　　　　　　PAM<br>GGACGCGTACACCCCAAGTCTGACATAAATgcagtttaaggttt<br>GGACGCGTACACCCCAAGTCTGACATAAATGCAGTTTAAGGTTT<br>[chromatogram trace]<br>(No Editing)5'-CTGCATTTATGTCAGACTTG-3' (SEQ ID NO: 42) | SEQ ID NO: 61<br>SEQ ID NO: 62<br>SEQ ID NO: 77<br><br>SEQ ID NO: 61<br>SEQ ID NO: 61 |
| MaTadA1.1-dCas9 | GGACGCGTACACCCCAAGTCTGACATAAATgcagtttaaggttt<br>CCTGCGCATGTGGGGTTCAGACTGTATTTAcgtcaaattccaaa<br>　　　　　　　　　　　　　　　　　　　　1　　　　5<br>　　　　　　　　　　　　　　　　　　　M Q F K V<br>　　　　　　　　PAM<br>GGACGCGTACACCCCAAGTCTGACATAAATgcagtttaaggttt<br>GGACGCGTACACCCCAAGTCTGACATAAAGGCAGTTTAAGGTTT<br>[chromatogram trace]<br>High Editing Efficiency. Red A5 peak was edited to blue G peak. | SEQ ID NO: 61<br>SEQ ID NO: 62<br>SEQ ID NO: 77<br><br>SEQ ID NO: 61<br>SEQ ID NO: 78 |
| MaTadA1.2-dCas9 | GGACGCGTACACCCCAAGTCTGACATAAATgcagtttaaggttt<br>CCTGCGCATGTGGGGTTCAGACTGTATTTAcgtcaaattccaaa<br>　　　　　　　　　　　　　　　　　　　　1　　　　5<br>　　　　　　　　　　　　　　　　　　　M Q F K V<br>　　　　　　　　PAM<br>GGACGCGTACACCCCAAGTCTGACATAAATgcagtttaaggttt<br>GGACGCGTACACCCCAAGTCTGACATAAATGCAGTTTAAGGTTT<br>[chromatogram trace]<br>Editing Competent with overlapping peaks. Red A5 peak was partly edited to blue G peak, resulting in overlapping peaks at this position. | SEQ ID NO: 61<br>SEQ ID NO: 62<br>SEQ ID NO: 77<br><br>SEQ ID NO: 61<br>SEQ ID NO: 61 |

FIG. 3C

| MaTadA1.3-dCas9 | GGACGCGTACACCCCAAGTCTGACATAAATgcagtttaaggttt<br>CCTGCGCATGTGGGGTTCAGACTGTATTTAcgtcaaattccaaa<br>　　　　　　　　　　　　　　　　　　　　1　　　　5<br>　　　　　　　　　　　　　　　　　　　M Q F K V<br>　　　　　　　　　PAM<br>GGACGCGTACACCCCAAGTCTGACATAAATgcagtttaaggttt<br>GGACGCGTACACCCCAAGTCTGACATAAATGCAGTTTAAGGTTT<br>[chromatogram trace]<br>Editing Competent with overlapping peaks. A5 peak was partly edited to G peak, resulting in overlapping peaks at this position. | SEQ ID NO: 61<br>SEQ ID NO: 62<br><br>SEQ ID NO: 77<br><br><br>SEQ ID NO: 61<br>SEQ ID NO: 61 |
| MaTadA1.4-dCas9 | GGACGCGTACACCCCAAGTCTGACATAAATgcagtttaaggttt<br>CCTGCGCATGTGGGGTTCAGACTGTATTTAcgtcaaattccaaa<br>　　　　　　　　　　　　　　　　　　　　1　　　　5<br>　　　　　　　　　　　　　　　　　　　M Q F K V<br>　　　　　　　　　PAM<br>GGACGCGTACACCCCAAGTCTGACATAAATgcagtttaaggttt<br>GGACGCGTACACCCCAAGTCTGACATAAATGCAGTTTAAGGTTT<br>[chromatogram trace]<br>Inferior Editing Effect. A5 peak was edited at low level to G peak (weak blue peak at the bottom). | SEQ ID NO: 61<br>SEQ ID NO: 62<br><br>SEQ ID NO: 77<br><br><br>SEQ ID NO: 61<br>SEQ ID NO: 61 |
| MaTadA1.5-dCas9 | GGACGCGTACACCCCAAGTCTGACATAAATgcagtttaaggttt<br>CCTGCGCATGTGGGGTTCAGACTGTATTTAcgtcaaattccaaa<br>　　　　　　　　　　　　　　　　　　　　1　　　　5<br>　　　　　　　　　　　　　　　　　　　M Q F K V<br>　　　　　　　　　PAM<br>GGACGCGTACACCCCAAGTCTGACATAAATgcagtttaaggttt<br>GGACGCGTACACCCCAAGTCTGACATAAATGCAGTTTAAGGTTT<br>[chromatogram trace]<br>Editing Competent with overlapping peaks. A5 peak was partly edited to G peak, resulting in overlapping peaks at this position. | SEQ ID NO: 61<br>SEQ ID NO: 62<br><br>SEQ ID NO: 77<br><br><br>SEQ ID NO: 61<br>SEQ ID NO: 61 |

FIG. 4

| | | |
|---|---|---|
| dCas9 control | attaacctgatgttctggggaatataAGctaagatgtcacggAGGtctagacgg<br>taattggactacaagaccccttatatCgattctacagtgccTCCagatctgcc | SEQ ID NO: 63<br>SEQ ID NO: 64 |
| | 95  100<br>I  N  L  M  F  W  G  I<br>PAM | SEQ ID NO: 79 |
| | attaacctgatgttctggggaatataAGctaagatgtcacggAGGtctagacgg<br>ATTAACCTGATGTTCTGGGGAATATAGCTAAGATGTCACGGAGGTCTAGACGG | SEQ ID NO: 65<br>SEQ ID NO: 66 |
| | (No Editing) 5'-atatAGctaagatgtcacgg-3' (SEQ ID NO: 43) | |
| TadA-8e-dCas9 | attaacctgatgttctggggaatataAGctaagatgtcacggAGGtctagacgg<br>taattggactacaagaccccttatatCgattctacagtgccTCCagatctgcc | SEQ ID NO: 63<br>SEQ ID NO: 64 |
| | 95  100<br>I  N  L  M  F  W  G  I<br>PAM | SEQ ID NO: 79 |
| | attaacctgatgttctggggaatataAGctaagatgtcacggAGGtctagacgg<br>ATTAACCTGATGTTCTGGGGAATGTGGCTAAGATGTCACGGAGGTCTAGACGG | SEQ ID NO: 63<br>SEQ ID NO: 67 |
| | High Editing Efficiency. Green A2 (position 2 from 5' end of SEQ ID NO: 43) and A4 (position 4 from the 5' end of SEQ ID NO: 43) peaks were edited to black G peaks. | |
| MaTadA1.0-dCas9 | attaacctgatgttctggggaatataAGctaagatgtcacggAGGtctagacgg<br>taattggactacaagaccccttatatCgattctacagtgccTCCagatctgcc | SEQ ID NO: 63<br>SEQ ID NO: 64 |
| | 95  100<br>I  N  L  M  F  W  G  I<br>PAM | SEQ ID NO: 79 |
| | attaacctgatgttctggggaatataAGctaagatgtcacggAGGtctagacgg<br>ATTAACCTGATGTTCTGGGGAATGTGGCTAAGATGTCACGGAGGTCTAGACGG | SEQ ID NO: 63<br>SEQ ID NO: 67 |
| | Editing Competent with overlapping peaks. Green A2 peak was partly edited to G peak, resulting in overlapping peaks at this position. A4 peak was edited to G peak. | |

FIG. 5A

| | | |
|---|---|---|
| dCas9 control | CTCTACTGTTTCTCCATACCCGTTTTTTTGGACGCGTACACCCAAGTCTGACATAAATgcagtttaaggtttacacctataaaagagagagccg<br>GAGATGACAAAGAGGTATGGGCAAAAAACCTGCGCATGTGGGT... aaattccaaatgtggatatttctctctcggc<br>(No Editing) | SEQ ID NO: 55<br>SEQ ID NO: 56<br>SEQ ID NO: 76<br>SEQ ID NO: 55<br>SEQ ID NO: 55 |
| TadA-8e-dCas9 | CTCTACTGTTTCTCCATACCCGTTTTTTTGGACGCGTACACCCAAGTCTGACATAAATgcagtttaaggtttacacctataaaagagagagccg<br>GAGATGACAAAGAGGTATGGGCAAAAAACCTGCGCATGTGGGT... <br>High Editing Efficiency | SEQ ID NO: 55<br>SEQ ID NO: 56<br>SEQ ID NO: 76<br>SEQ ID NO: 55<br>SEQ ID NO: 70 |
| MaTadA1.0-1-dCas9 | CTCTCTACTGTTTCTCCATACCCGTTTTTTTGGACGCGTACACCCAAGTCTGACATAAATgcagtttaaggtttacacctataaaagagagagccgt<br>GAGATGACAAAGAGGTATGGGCAAAAAACCTGCGCATGTGGG... <br>Editing Competent with overlapping peaks. A5 peak was partly edited to G peak, resulting in overlapping peaks at this position. A9 peak was not edited. | SEQ ID NO: 68<br>SEQ ID NO: 69<br>SEQ ID NO: 76<br>SEQ ID NO: 68<br>SEQ ID NO: 71 |
| MaTadA1.0-2-dCas9 | CTCTCTACTGTTTCTCCATACCCGTTTTTTTGGACGCGTACACCCAAGTCTGACATAAATgcagtttaaggtttacacctataaaagagagagccgt<br>GAGATGACAAAGAGGTATGGGCAAAAAACCTGCGCATGTGGG... <br>Editing Competent with overlapping peaks. A5 peak was partly edited to G peak, resulting in overlapping peaks at this position. A9 peak was not edited. | SEQ ID NO: 68<br>SEQ ID NO: 69<br>SEQ ID NO: 76<br>SEQ ID NO: 68<br>SEQ ID NO: 71 |
| MaTadA1.0-3-dCas9 | CTCTCTACTGTTTCTCCATACCCGTTTTTTTGGACGCGTACACCCAAGTCTGACATAAATgcagtttaaggtttacacctataaaagagagagccg<br>GAGATGACAAAGAGGTATGGGCAAAAAACCTGCGCATGTGGG... <br>Editing Competent with overlapping peaks. A5 peak was completely edited to G peak. A9 peak was partly edited to G peak, resulting in overlapping peaks at this position. | SEQ ID NO: 68<br>SEQ ID NO: 69<br>SEQ ID NO: 76<br>SEQ ID NO: 68<br>SEQ ID NO: 58 |

FIG. 5B

| ZoTadA1.0-1-dCas9 | | SEQ ID NO: 68<br>SEQ ID NO: 69<br>SEQ ID NO: 76<br><br>SEQ ID NO: 68<br>SEQ ID NO: 74 |
|---|---|---|
| | Editing Competent with overlapping peaks. A5 peak was completely edited to G peak. A9 peak was partly edited to G peak, resulting in overlapping peaks at this position. | |
| ZoTadA1.0-2-dCas9 | | SEQ ID NO: 68<br>SEQ ID NO: 69<br>SEQ ID NO: 76<br><br>SEQ ID NO: 68<br>SEQ ID NO: 74 |
| | Editing Competent with overlapping peaks. A5 peak was completely edited to G peak. A9 peak was partly edited to G peak, resulting in overlapping peaks at this position. | |
| ZoTadA1.0-3-dCas9 | | SEQ ID NO: 68<br>SEQ ID NO: 69<br>SEQ ID NO: 76<br><br>SEQ ID NO: 68<br>SEQ ID NO: 74 |
| | Editing Competent with overlapping peaks. A5 peak was completely edited to G peak. A9 peak was partly edited to G peak, resulting in overlapping peaks at this position. | |

FIG. 5C

| ErTadA1.0-1-dCas9 | | SEQ ID NO: 68<br>SEQ ID NO: 69<br>SEQ ID NO: 76 |
|---|---|---|
| | | SEQ ID NO: 68<br>SEQ ID NO: 75 |
| | Editing Competent with overlapping peaks. A5 peak was completely edited to G peak. A9 peak was partly edited to G peak, resulting in overlapping peaks at this position. | |
| ErTadA1.0-2-dCas9 | | SEQ ID NO: 68<br>SEQ ID NO: 69<br>SEQ ID NO: 76 |
| | | SEQ ID NO: 68<br>SEQ ID NO: 72 |
| | Editing Competent with overlapping peaks. A5 peak was completely edited to G peak. A9 peak was partly edited to G peak, resulting in overlapping peaks at this position. | |
| ErTadA1.0-3-dCas9 | | SEQ ID NO: 68<br>SEQ ID NO: 69<br>SEQ ID NO: 76 |
| | | SEQ ID NO: 68<br>SEQ ID NO: 71 |
| | Editing Competent with overlapping peaks. A5 peak was partly edited to G peak (with overlapping peaks). A9 peak was not edited to G peak. | | pX330

| sgRNA(5'-3') | | G | A2 | A3 | C | A5 | C | A7 | A8 | A9 | G | C | A12 | T | A14 | G | A16 | C | T | G | C |
|---|---|---|---|---|---|---|---|---|---|---|---|---|---|---|---|---|---|---|---|---|---|
| A→G editing efficiency (%) | T | 2 | 3 | 7 | 0 | 7 | 0 | 6 | 5 | 5 | 9 | 0 | 5 | 97 | 3 | 11 | 5 | 2 | 93 | 2 | 0 |
| | G | 90 | 4 | 2 | 0 | 5 | 0 | 4 | 3 | 3 | 86 | 1 | 3 | 0 | 3 | 83 | 4 | 4 | 5 | 96 | 3 |
| | C | 1 | 1 | 2 | 98 | 2 | 98 | 3 | 2 | 0 | 3 | 97 | 1 | 0 | 2 | 0 | 1 | 91 | 1 | 2 | 97 |
| | A | 7 | 92 | 90 | 2 | 87 | 2 | 88 | 91 | 93 | 3 | 2 | 91 | 3 | 93 | 6 | 91 | 2 | 1 | 0 | 0 |

| sgRNA(3'-5') | | T21 | G | G | G | G | C | T15 | G | G | C | C | A | C | G | C | T6 | C | A | C | G | C |
|---|---|---|---|---|---|---|---|---|---|---|---|---|---|---|---|---|---|---|---|---|---|---|
| A→G editing efficiency (%) | T | 92 | 1 | 1 | 2 | 2 | 4 | 94 | 2 | 1 | 4 | 2 | 2 | 0 | 3 | 3 | 67 | 2 | 4 | 3 | 0 | 3 |
| 0 | G | 5 | 96 | 96 | 97 | 94 | 4 | 3 | 95 | 93 | 3 | 0 | 2 | 3 | 92 | 2 | 2 | 1 | 4 | 3 | 95 | 94 |
| | C | 3 | 1 | 1 | 0 | 2 | 91 | 2 | 1 | 2 | 92 | 96 | 4 | 95 | 2 | 93 | 29 | 95 | 4 | 92 | 2 | 1 |
| | A | 0 | 1 | 3 | 2 | 2 | 1 | 0 | 2 | 3 | 1 | 2 | 92 | 3 | 3 | 2 | 2 | 2 | 88 | 2 | 3 | 2 | pX330-MaTadA-WT-nCas9-P992L

| sgRNA(3'-5') | | T | G | G | G | G | C | T | G | G | C | C | A | C | G | C | T | C | A | C | G | C |
|---|---|---|---|---|---|---|---|---|---|---|---|---|---|---|---|---|---|---|---|---|---|---|
| A→G editing efficiency (%) | T | 91 | 1 | 1 | 3 | 2 | 5 | 95 | 2 | 2 | 6 | 0 | 3 | 0 | 2 | 4 | 92 | 3 | 3 | 0 | 4 | 3 |
| 0 | G | 5 | 96 | 95 | 94 | 93 | 4 | 4 | 95 | 92 | 3 | 1 | 2 | 3 | 91 | 3 | 2 | 2 | 5 | 3 | 91 | 93 |
| | C | 3 | 1 | 2 | 0 | 2 | 91 | 2 | 1 | 2 | 90 | 97 | 4 | 94 | 2 | 93 | 4 | 93 | 5 | 95 | 2 | 2 |
| | A | 0 | 2 | 2 | 3 | 3 | 1 | 0 | 2 | 4 | 1 | 2 | 91 | 3 | 5 | 0 | 2 | 2 | 87 | 2 | 3 | 2 | pX330-TadA-8e-P992L

| sgRNA(3'-5') | | T21 | G | G | G | G | C | T15 | G | G | C | C | A | C | G | C | T6 | C | A | C | G | C |
|---|---|---|---|---|---|---|---|---|---|---|---|---|---|---|---|---|---|---|---|---|---|---|
| A→G editing efficiency (%) | T | 94 | 1 | 2 | 2 | 4 | 4 | 95 | 1 | 4 | 0 | 0 | 5 | 0 | 7 | 5 | 71 | 3 | 7 | 0 | 4 | 3 |
| 80 | G | 4 | 95 | 95 | 95 | 92 | 3 | 3 | 94 | 91 | 3 | 1 | 2 | 2 | 87 | 2 | 1 | 1 | 3 | 2 | 89 | 93 |
| | C | 2 | 1 | 1 | 0 | 1 | 93 | 3 | 2 | 1 | 96 | 98 | 4 | 96 | 2 | 92 | 26 | 95 | 4 | 97 | 2 | 1 |
| | A | 0 | 2 | 3 | 3 | 3 | 0 | 0 | 3 | 4 | 1 | 2 | 89 | 2 | 5 | 1 | 2 | 1 | 86 | 2 | 4 | 2 |

| sgRNA(3'-5') | | T | G | G | G | G | C | T | G | G | C | C | A | C | G | C | T6 | C | A | C | G | C |
|---|---|---|---|---|---|---|---|---|---|---|---|---|---|---|---|---|---|---|---|---|---|---|
| A→G editing efficiency (%) | T | 92 | 1 | 1 | 2 | 3 | 4 | 96 | 2 | 4 | 8 | 0 | 4 | 0 | 6 | 4 | 96 | 3 | 6 | 0 | 6 | 4 |
| 00 | G | 4 | 95 | 94 | 95 | 93 | 3 | 2 | 94 | 91 | 3 | 1 | 2 | 2 | 89 | 1 | 1 | 1 | 2 | 2 | 89 | 93 |
| | C | 2 | 1 | 2 | 0 | 1 | 94 | 1 | 3 | 2 | 89 | 98 | 4 | 96 | 1 | 94 | 1 | 95 | 4 | 96 | 2 | 1 |
| | A | 1 | 2 | 2 | 3 | 2 | 0 | 0 | 2 | 3 | 1 | 2 | 90 | 2 | 4 | 1 | 2 | 1 | 87 | 2 | 4 | 2 |

SEQUENCE LISTING

```
Sequence total quantity: 83
SEQ ID NO: 1          moltype = AA  length = 170
FEATURE               Location/Qualifiers
source                1..170
                      mol_type = protein
```

```
                      organism  = synthetic construct
SEQUENCE: 1
MTGSETDHIR WMRHALTLAQ RAWDEGEVPV GAVLVYQGQV IGEGWNRPIG HHDPTAHAEM    60
MALRQGGIVL QNYRLLDTTL YVTLEPCVMC AGAMVHSRIG QLIYGASDVK TGAAGSLMDV   120
LGHPGMNHKV SVAGGVLAQE CAGLLSDFFR MRRQVHKANK QATRQQSEEQ              170

SEQ ID NO: 2          moltype = AA   length = 170
FEATURE               Location/Qualifiers
source                1..170
                      mol_type = protein
                      organism = synthetic construct
SEQUENCE: 2
MTGSETDHIR WMRHALTLAQ RARDEGEVPV GAVLVLQGQV IGEGWNRAIG LHDPTAHAEM    60
MALRQGGIVL QNYRLLDTTL YVTFEPCVMC AGAMVHSRIG QLIYGVSNSK RGAAGSLMNV   120
LNYPGMNHKV SVAGGVLAQE CAGLLCDFYR MPRQVFNANK QATRQQSINQ              170

SEQ ID NO: 3          moltype = AA   length = 170
FEATURE               Location/Qualifiers
source                1..170
                      mol_type = protein
                      organism = synthetic construct
SEQUENCE: 3
MTGSETDHIR WMRHALTLAQ RAKDEGEVPV GAVLVVQGQV IGEGWNRAIG VHDPTAHAEM    60
MALRQGGIVL QNYRLLDTTL YVTWEPCVMC AGAMVHSRIG QLIYGISNSK KGAAGSLMNV   120
LNYPGMNHKV SVAGGVLAQE CAGLLCDFYR MPRQVWNANK QATRQQSINQ              170

SEQ ID NO: 4          moltype = AA   length = 170
FEATURE               Location/Qualifiers
source                1..170
                      mol_type = protein
                      organism = synthetic construct
SEQUENCE: 4
MTGSETDHIR WMRHALTLAQ RAHDEGEVPV GAVLVIQGQV IGEGWNRAIG IHDPTAHAEM    60
MALRQGGIVL QNYRLLDTTL YVTYEPCVMC AGAMVHSRIG QLIYGLSNSK HGAAGSLMNV   120
LNYPGMNHKV SVAGGVLAQE CAGLLCDFYR MPRQVYNANK QATRQQSINQ              170

SEQ ID NO: 5          moltype = AA   length = 170
FEATURE               Location/Qualifiers
source                1..170
                      mol_type = protein
                      organism = synthetic construct
SEQUENCE: 5
MTGSETDHIR WMRHALTLAQ RARDEGEVPV GAVLVPQGQV IGEGWNRAIG PHDPTAHAEM    60
MALRQGGIVL QNYRLLDTTL YVTFEPCVMC AGAMVHSRIG QLIYGPSNSK RGAAGSLMNV   120
LNYPGMNHKV SVAGGVLAQE CAGLLCDFYR MPRQVFNANK QATRQQSINQ              170

SEQ ID NO: 6          moltype = AA   length = 170
FEATURE               Location/Qualifiers
source                1..170
                      mol_type = protein
                      organism = synthetic construct
SEQUENCE: 6
MTGSETDHIR WMRHALTLAQ RARDEGEVPV GAVLVLQGQV IGEGWNRAIG LHDPTAHAEM    60
MALRQGGIVL QNYRLLDTTL YVTFEPCVMC AGAMVHSRIG QLIYGVSNSK RGAAGSLMQV   120
LNYPGMNHKV SVAGGVLAQE CAGLLCDFYR MPRQVFNANK QATRQQSINQ              170

SEQ ID NO: 7          moltype = AA   length = 170
FEATURE               Location/Qualifiers
source                1..170
                      mol_type = protein
                      organism = synthetic construct
SEQUENCE: 7
MTGSETDHIR WMRHALTLAQ RARDEGEVPV GAVLVLQGQV IGEGWNRAIG LHDPTAHAEM    60
MALRQGGIVL QNYRLLDTTL YVTFEPCVMC AGAMVHSRIG QLIYGVSNSK RGAAGSLMRV   120
LNYPGMNHKV SVAGGVLAQE CAGLLCDFYR MPRQVFNANK QATRQQSINQ              170

SEQ ID NO: 8          moltype = AA   length = 170
FEATURE               Location/Qualifiers
source                1..170
                      mol_type = protein
                      organism = synthetic construct
SEQUENCE: 8
MTGSETDHIR WMRHALTLAQ RARDEGEVPV GAVLVLQGQV IGEGWNRAIG LHDPTAHAEM    60
MALRQGGIVL QNYRLLDTTL YVTFEPCVMC AGAMVHSRIG QLIYGVSNSK KGAAGSLMNV   120
LNYPGMNHKV SVAGGVLAQE CAGLLCDFYR MPRQVFNANK QATRQQSINQ              170

SEQ ID NO: 9          moltype = AA   length = 170
FEATURE               Location/Qualifiers
source                1..170
```

```
                        mol_type = protein
                        organism = synthetic construct
SEQUENCE: 9
MTGSETDHIR WMRHALTLAQ RARDEGEVPV GAVLVLQGQV IGEGWNRAIG LHDPTAHAEM    60
MALRQGGIVL QNYRLLDTTL YVTFEPCVMC AGAMVHSRIG QLIYGVSNSR KGAAGSLMNV   120
LNYPGMNHKV SVAGGVLAQE CAGLLCDFYR MPRQVFNANK QATRQQSINQ              170

SEQ ID NO: 10           moltype = AA  length = 170
FEATURE                 Location/Qualifiers
source                  1..170
                        mol_type = protein
                        organism = synthetic construct
SEQUENCE: 10
MTGSETDHIR WMRHALTLAQ RARDEGEVPV GAVLVLQGQV IGEGWNRAIG LHDPTAHAEM    60
MALRQGGIVL QNYRLLDTTL YVTFEPCVMC AGAMVHSRIG QLIYGVSNSK RGAAGSLMNV   120
LNYPGMNHKV SVAGGVLAQE CAGLLCDFHR MPRQVFNANK QATRQQSINQ              170

SEQ ID NO: 11           moltype = AA  length = 8
FEATURE                 Location/Qualifiers
source                  1..8
                        mol_type = protein
                        organism = synthetic construct
SEQUENCE: 11
SGGSSGGS                                                              8

SEQ ID NO: 12           moltype = AA  length = 169
FEATURE                 Location/Qualifiers
source                  1..169
                        mol_type = protein
                        organism = synthetic construct
SEQUENCE: 12
MSELYSDEYW MEQALERAKR AEQQNEIPVG AVVVLNNQII GEGWNQTITL HNPTAHAEIM    60
ALEEAGLSQQ NYRLVGATLY VTLEPCMMCA GAIIHSRIER LVYGASDFKT GAAGSFIDLL   120
RYPGINHCVQ ISSGVLQEQC SSLLSEFFRR RRQEIKQQKK SQESLLVES               169

SEQ ID NO: 13           moltype = AA  length = 169
FEATURE                 Location/Qualifiers
source                  1..169
                        mol_type = protein
                        organism = synthetic construct
SEQUENCE: 13
MSELYSDEYW MEQALERAKR ARQQNEIPVG AVVVLNNQII GEGWNQAITL HNPTAHAEIM    60
ALEEAGLSQQ NYRLVGATLY VTFEPCMMCA GAIIHSRIER LVYGSNVKR GAAGSFINLL   120
NYPGINHCVQ ISSGVLQEQC SSLLCEFYRR PRQVINQQKK SQESLLINS               169

SEQ ID NO: 14           moltype = AA  length = 169
FEATURE                 Location/Qualifiers
source                  1..169
                        mol_type = protein
                        organism = synthetic construct
SEQUENCE: 14
MSELYSDEYW MEQALERAKR AKQQNEIPVG AVVVLNNQII GEGWNQAITL HNPTAHAEIM    60
ALEEAGLSQQ NYRLVGATLY VTWEPCMMCA GAIIHSRIER LVYGISNIKK GAAGSFINLL   120
NYPGINHCVQ ISSGVLQEQC SSLLCEFYRR PRQIINQQKK SQESLLINS               169

SEQ ID NO: 15           moltype = AA  length = 169
FEATURE                 Location/Qualifiers
source                  1..169
                        mol_type = protein
                        organism = synthetic construct
SEQUENCE: 15
MSELYSDEYW MEQALERAKR AHQQNEIPVG AVVVLNNQII GEGWNQAITL HNPTAHAEIM    60
ALEEAGLSQQ NYRLVGATLY VTYEPCMMCA GAIIHSRIER LVYGLSNLKH GAAGSFINLL   120
NYPGINHCVQ ISSGVLQEQC SSLLCEFYRR PRQLINQQKK SQESLLINS               169

SEQ ID NO: 16           moltype = AA  length = 169
FEATURE                 Location/Qualifiers
source                  1..169
                        mol_type = protein
                        organism = synthetic construct
SEQUENCE: 16
MSELYSDEYW MEQALERAKR ARQQNEIPVG AVVVLNNQII GEGWNQAITL HNPTAHAEIM    60
ALEEAGLSQQ NYRLVGATLY VTFEPCMMCA GAIIHSRIER LVYGPSNPKR GAAGSFINLL   120
NYPGINHCVQ ISSGVLQEQC SSLLCEFYRR PRQPINQQKK SQESLLINS               169

SEQ ID NO: 17           moltype = AA  length = 170
FEATURE                 Location/Qualifiers
source                  1..170
                        mol_type = protein
```

```
                        organism = synthetic construct
SEQUENCE: 17
MSDTQIDEKW MRHALTLARR AWEEGEVPVG AVLVQGDTVI GEGWNRPIGY HDPTAHAEIM    60
ALRQGGKVLE NYRLLDTTLY VTLEPCVMCA GAMVHGRVGR LVFGARDEKT GAAGSLLDIL   120
GHAGMNHQVS VEQGVLAAEC AAMLSNFFRQ RRAEKKALRD RLRAELLKGE              170

SEQ ID NO: 18           moltype = AA  length = 170
FEATURE                 Location/Qualifiers
source                  1..170
                        mol_type = protein
                        organism = synthetic construct
SEQUENCE: 18
MSDTQIDEKW MRHALTLARR AREEGEVPVG AVLVLGDTVI GEGWNRAIGL HDPTAHAEIM    60
ALRQGGKVLE NYRLLDTTLY VTFEPCVMCA GAMVHGRVGR LVFGVRNSKR GAAGSLLNIL   120
NYAGMNHQVS VEQGVLAAEC AAMLCNFYRQ PRAVFNALRD RLRAELLKIN              170

SEQ ID NO: 19           moltype = AA  length = 170
FEATURE                 Location/Qualifiers
source                  1..170
                        mol_type = protein
                        organism = synthetic construct
SEQUENCE: 19
MSDTQIDEKW MRHALTLARR AKEEGEVPVG AVLVVGDTVI GEGWNRAIGV HDPTAHAEIM    60
ALRQGGKVLE NYRLLDTTLY VTWEPCVMCA GAMVHGRVGR LVFGIRNSKK GAAGSLLNIL   120
NYAGMNHQVS VEQGVLAAEC AAMLCNFYRQ PRAIWNALRD RLRAELLKIN              170

SEQ ID NO: 20           moltype = AA  length = 170
FEATURE                 Location/Qualifiers
source                  1..170
                        mol_type = protein
                        organism = synthetic construct
SEQUENCE: 20
MSDTQIDEKW MRHALTLARR AHEEGEVPVG AVLVIGDTVI GEGWNRAIGI HDPTAHAEIM    60
ALRQGGKVLE NYRLLDTTLY VTYEPCVMCA GAMVHGRVGR LVFGLRNSKH GAAGSLLNIL   120
NYAGMNHQVS VEQGVLAAEC AAMLCNFYRQ PRALYNALRD RLRAELLKIN              170

SEQ ID NO: 21           moltype = AA  length = 170
FEATURE                 Location/Qualifiers
source                  1..170
                        mol_type = protein
                        organism = synthetic construct
SEQUENCE: 21
MSDTQIDEKW MRHALTLARR AREEGEVPVG AVLVPGDTVI GEGWNRAIGP HDPTAHAEIM    60
ALRQGGKVLE NYRLLDTTLY VTFEPCVMCA GAMVHGRVGR LVFGPRNSKR GAAGSLLNIL   120
NYAGMNHQVS VEQGVLAAEC AAMLCNFYRQ PRAPFNALRD RLRAELLKIN              170

SEQ ID NO: 22           moltype = AA  length = 1368
FEATURE                 Location/Qualifiers
source                  1..1368
                        mol_type = protein
                        organism = synthetic construct
SEQUENCE: 22
MDKKYSIGLA IGTNSVGWAV ITDEYKVPSK KFKVLGNTDR HSIKKNLIGA LLFDSGETAE    60
ATRLKRTARR RYTRRKNRIC YLQEIFSNEM AKVDDSFFHR LEESFLVEED KKHERHPIFG   120
NIVDEVAYHE KYPTIYHLRK KLVDSTDKAD LRLIYLALAH MIKFRGHFLI EGDLNPDNSD   180
VDKLFIQLVQ TYNQLFEENP INASGVDAKA ILSARLSKSR RLENLIAQLP GEKKNGLFGN   240
LIALSLGLTP NFKSNFDLAE DAKLQLSKDT YDDDLDNLLA QIGDQYADLF LAAKNLSDAI   300
LLSDILRVNT EITKAPLSAS MIKRYDEHHQ DLTLLKALVR QQLPEKYKEI FFDQSKNGYA   360
GYIDGGASQE EFYKFIKPIL EKMDGTEELL VKLNREDLLR KQRTFDNGSI PHQIHLGELH   420
AILRRQEDFY PFLKDNREKI EKILTFRIPY YVGPLARGNS RFAWMTRKSE ETITPWNFEE   480
VVDKGASAQS FIERMTNFDK NLPNEKVLPK HSLLYEYFTV YNELTKVKYV TEGMRKPAFL   540
SGEQKKAIVD LLFKTNRKVT VKQLKEDYFK KIECFDSVEI SGVEDRFNAS LGTYHDLLKI   600
IKDKDFLDNE ENEDILEDIV LTLTLFEDRE MIEERLKTYA HLFDDKVMKQ LKRRRYTGWG   660
RLSRKLINGI RDKQSGKTIL DFLKSDGFAN RNFMQLIHDD SLTFKEDIQK AQVSGQGDSL   720
HEHIANLAGS PAIKKGILQT VKVVDELVKV MGRHKPENIV IEMARENQTT QKGQKNSRER   780
MKRIEEGIKE LGSQILKEHP VENTQLQNEK LYLYYLQNGR DMYVDQELDI NRLSDYDVDA   840
IVPQSFLKDD SIDNKVLTRS DKNRGKSDNV PSEEVVKKMK NYWRQLLNAK LITQRKFDNL   900
TKAERGGLSE LDKAGFIKRQ LVETRQITKH VAQILDSRMN TKYDENDKLI REVKVITLKS   960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGD              1368

SEQ ID NO: 23           moltype = AA  length = 1368
FEATURE                 Location/Qualifiers
source                  1..1368
```

```
                        mol_type = protein
                        organism = synthetic construct
SEQUENCE: 23
MDKKYSIGLA IGTNSVGWAV ITDEYKVPSK KFKVLGNTDR HSIKKNLIGA LLFDSGETAE    60
ATRLKRTARR RYTRRKNRIC YLQEIFSNEM AKVDDSFPHR LEESFLVEED KKHERHPIFG   120
NIVDEVAYHE KYPTIYHLRK KLVDSTDKAD LRLIYLALAH MIKFRGHFLI EGDLNPDNSD   180
VDKLFIQLVQ TYNQLFEENP INASGVDAKA ILSARLSKSR RLENLIAQLP GEKKNGLFGN   240
LIALSLGLTP NFKSNFDLAE DAKLQLSKDT YDDDLDNLLA QIGDQYADLF LAAKNLSDAI   300
LLSDILRVNT EITKAPLSAS MIKRYDEHHQ DLTLLKALVR QQLPEKYKEI FFDQSKNGYA   360
GYIDGGASQE EFYKFIKPIL EKMDGTEELL VKLNREDLLR KQRTFDNGSI PHQIHLGELH   420
AILRRQEDFY PFLKDNREKI EKILTFRIPY YVGPLARGNS RFAWMTRKSE ETITPWNFEE   480
VVDKGASAQS FIERMTNFDK NLPNEKVLPK HSLLYEYFTV YNELTKVKYV TEGMRKPAFL   540
SGEQKKAIVD LLFKTNRKVT VKQLKEDYFK KIECFDSVEI SGVEDRFNAS LGTYHDLLKI   600
IKDKDFLDNE ENEDILEDIV LTLTLFEDRE MIEERLKTYA HLFDDKVMKQ LKRRRYTGWG   660
RLSRKLINGI RDKQSGKTIL DFLKSDGFAN RNFMQLIHDD SLTFKEDIQK AQVSGQGDSL   720
HEHIANLAGS PAIKKGILQT VKVVDELVKV MGRHKPENIV IEMARENQTT QKGQKNSRER   780
MKRIEEGIKE LGSQILKEHP VENTQLQNEK LYLYYLQNGR DMYVDQELDI NRLSDYDVDH   840
IVPQSFLKDD SIDNKVLTRS DKNRGKSDNV PSEEVVKKMK NYWRQLLNAK LITQRKFDNL   900
TKAERGGLSE LDKAGFIKRQ LVETRQITKH VAQILDSRMN TKYDENDKLI REVKVITLKS   960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKYLDEII  EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGD              1368

SEQ ID NO: 24          moltype = DNA   length = 510
FEATURE                Location/Qualifiers
source                 1..510
                       mol_type = other DNA
                       organism = synthetic construct
SEQUENCE: 24
atgaccggtt ccgaaactga ccacatccgt tggatgcgcc acgcactgac cctggcacag    60
cgtgctcgtg atgaaggtga agtaccggta ggtgccgttc tggttctgca aggtcaggtt   120
atcggcgagg gttggaatcg tgccattggt ctgcacgatc cgactgctca tgctgagatg   180
atggccctgc gtcagggcgg cattgttctg cagaactatc gtctgctgga caccaccctg   240
tacgtaactt tcgaaccgtg cgtcatgtgc gctggtgcga tggttcactc tcgtatcggc   300
cagctgattt acggtgtctc taacagcaaa cgtggtgcca cgggtagcct gatgaacgtt   360
ctgaattacc cgggcatgaa ccacaaggtt tctgttgctg gtggtgttct ggctcaggaa   420
tgcgcgggcc tgctgtgcga ttttaccgt atgccgcgtc aggtcttcaa cgcgaacaaa    480
caggcgaccc gtcaacaatc catcaaccag                                     510

SEQ ID NO: 25          moltype = DNA   length = 510
FEATURE                Location/Qualifiers
source                 1..510
                       mol_type = other DNA
                       organism = synthetic construct
SEQUENCE: 25
atgacaggca gtgaaaccga ccatattaga tggatgagac atgccctcac actggcccag    60
agagctagag atgaaggtga ggttcccgtg ggagccgtgc tggtgctgca gggcaggtt    120
atcggcgaag gctggaacag ggccattggc ctccacgatc ccaccgctca tgcagagatg   180
atggccctca gacaaggcgg aattgtcctg cagaactaca ggctcctgga caacacactc   240
tatgtgacct tgaacccctg tgttatgtgc gctggcgcaa tggttcattc acgcattgga   300
cagctcatct atggcgtgag caatagtaaa cgcggcgctc ccgggagcct gatgaacgtc   360
ctgaattatc ccggtatgaa tcataaagtc tccgtcgccg gaggcgtgct ggcacaagag   420
tgtgcagggc tgctgtgtga ctttaccgg atgcctaggc aagttttcaa cgctaacaag    480
caggctaccc gccagcagag catcaatcag                                     510

SEQ ID NO: 26          moltype = AA    length = 32
FEATURE                Location/Qualifiers
source                 1..32
                       mol_type = protein
                       organism = synthetic construct
SEQUENCE: 26
SGGSSGGSSG SETPGTSESA TPESSGGSSG GS                                   32

SEQ ID NO: 27          moltype = AA    length = 4
FEATURE                Location/Qualifiers
source                 1..4
                       mol_type = protein
                       organism = synthetic construct
SEQUENCE: 27
SGGS                                                                   4

SEQ ID NO: 28          moltype = DNA   length = 507
FEATURE                Location/Qualifiers
source                 1..507
                       mol_type = other DNA
```

-continued

```
                        organism = synthetic construct
SEQUENCE: 28
atgagcgaac tgtatagcga cgaatactgg atggaacaag cactggaacg tgctaaacgt    60
gcccgtcagc agaacgaaat cccagttggt gctgttgtgg tcctgaacaa ccagatcatc   120
ggtgaaggct ggaaccaggc aattaccctg cataaccta ccgcacacgc agaaatcatg    180
gcgctggaag aagccggcct gtctcagcaa aattaccgtc tggttggcgc gactctgtac   240
gtgactttcg aaccgtgtat gatgtgcgct ggcgctatta ttcactcccg catcgaacgt   300
ctggtgtacg gcgtgtctaa cgttaaacgc ggcgcggctg gttccttcat taatctgctg   360
aactacccgg gcatcaacca ctgcgttcag attagctccg gcgtgctgca agaacagtgt   420
tcttccctgc tgtgtgaatt ctaccgtcgt cctcgtcagg ttatcaacca gcagaaaaag   480
agccaggagt ccctgctgat taactcc                                       507

SEQ ID NO: 29           moltype = DNA  length = 507
FEATURE                 Location/Qualifiers
source                  1..507
                        mol_type = other DNA
                        organism = synthetic construct
SEQUENCE: 29
atgtctgagc tgtattctga cgagtattgg atggagcaag ccctggaaag agctaaacgg    60
gctcgccagc agaatgagat tcccgtcggc gccgtggtgg tgctgaataa tcagatcata   120
ggtgagggtt ggaatcaggc cattactctg cacaacccaa ccgcccacgc cgagattatg   180
gccctggaag aagcagggct gtcacaacag aactaccgtc tggtcggcgg tactctgtac   240
gtcacatttg agccctgtat gatgtgtgct ggcgccatta tccactcccg catcgaaaga   300
ctggtgtatg gtgtgtccaa tgtgaaacgc ggcgcagccg gatctttcat caaccctgctc  360
aattatccag ggattaacca ctgcgtccaa atttctagtg gcgtcctgca ggaacaatgc   420
tcatcccctcc tgtgcgagtt ttatagaagg ccacgccagg tgattaatca gcaaaagaag   480
tcccaagaga gtctgctgat caacagt                                        507

SEQ ID NO: 30           moltype = DNA  length = 510
FEATURE                 Location/Qualifiers
source                  1..510
                        mol_type = other DNA
                        organism = synthetic construct
SEQUENCE: 30
atgtccgata cccagatcga tgaaaagtgg atgcgccatg ccctgaccct ggcccgccgt    60
gctcgtgaag aaggcgaagt accggttggt gctgtactgg tcctgggcga taccgttatc   120
ggtgaaggtt ggaaccgtgc gattggtctg cacgacccga ccgctcacgc ggagattatg   180
gcactgcgtc aaggcggcaa ggttctggaa aactaccgcc tgctggacac caccctgtat   240
gttaccttcg agccgtgtgt aatgtgtgcg ggtgcgctg ttcatggtcg tgtcggtcgt   300
ctggttttcg gtgtgcgtaa ctctaaacgt ggtgctgcgg gtagcctgct gaatatcctg   360
aactacgcgg gtatgaacca tcaggtctct gttgagcagg gtgtactggc ggctgaatgc   420
gctgccatgc tgtgtaactt ctaccgtcag cctcgtgctg ttttcaacgc tctgcgtgat   480
cgtctgcgtg cggagctgct gaaaatcaac                                     510

SEQ ID NO: 31           moltype = DNA  length = 510
FEATURE                 Location/Qualifiers
source                  1..510
                        mol_type = other DNA
                        organism = synthetic construct
SEQUENCE: 31
atgagtgata cacagatcga cgagaaatgg atgagacacg ccctcacact ggccaggagg    60
gcaagggagg agggcgaagt ccctgtcgga gctgtgctgg tcctcggcga taccgtgatt   120
ggtgagggct ggaatagagc tattggcctg catgatccta cagcacacgc tgaaatcatg   180
gcactccggc aaggcggcaa ggttctggag aactatcgcc tgctggacac aaaccctgtac  240
gtcacctttg aaccatcgt catgtgtgcc ggagcaatgg tcacggcag agtgggacgg   300
ctggtcttcg gcgtgcggaa cagcaaacgc ggtgctgcag gttccctcct gaacatactg   360
aattacgcag gaatgaacca tcaggtgagc gttgagcagg gagtcctggc tgcagaatgc   420
gccgctatgc tctgcaactt ttacaggcag ccaagggccg tgttcaacgc cctccgcgac   480
agactgaggg ccgaactcct gaaaatcaat                                     510

SEQ ID NO: 32           moltype = DNA  length = 21
FEATURE                 Location/Qualifiers
source                  1..21
                        mol_type = other DNA
                        organism = synthetic construct
SEQUENCE: 32
cccaagaaga agaggaaagt c                                              21

SEQ ID NO: 33           moltype = AA  length = 7
FEATURE                 Location/Qualifiers
source                  1..7
                        mol_type = protein
                        organism = synthetic construct
SEQUENCE: 33
PKKKRKV                                                              7

SEQ ID NO: 34           moltype = AA  length = 30
FEATURE                 Location/Qualifiers
source                  1..30
```

```
                        mol_type = protein
                        organism = synthetic construct
SEQUENCE: 34
MDSLLMNRRK FLYQFKNVRW AKGRRETYLC                                          30

SEQ ID NO: 35           moltype = AA   length = 18
FEATURE                 Location/Qualifiers
source                  1..18
                        mol_type = protein
                        organism = synthetic construct
SEQUENCE: 35
KRTADGSEFE SPKKKRKV                                                       18

SEQ ID NO: 36           moltype = AA   length = 17
FEATURE                 Location/Qualifiers
source                  1..17
                        mol_type = protein
                        organism = synthetic construct
SEQUENCE: 36
KRTADGSEFE PKKKRKV                                                        17

SEQ ID NO: 37           moltype = AA   length = 4
FEATURE                 Location/Qualifiers
source                  1..4
                        mol_type = protein
                        organism = synthetic construct
SEQUENCE: 37
GGGS                                                                      4

SEQ ID NO: 38           moltype = AA   length = 5
FEATURE                 Location/Qualifiers
source                  1..5
                        mol_type = protein
                        organism = synthetic construct
SEQUENCE: 38
SGGGS                                                                     5

SEQ ID NO: 39           moltype = AA   length = 16
FEATURE                 Location/Qualifiers
source                  1..16
                        mol_type = protein
                        organism = synthetic construct
SEQUENCE: 39
SGSETPGTSE SATPES                                                         16

SEQ ID NO: 40           moltype = DNA   length = 24
FEATURE                 Location/Qualifiers
source                  1..24
                        mol_type = other DNA
                        organism = synthetic construct
SEQUENCE: 40
tccggaggat ctagcggagg ctcc                                                24

SEQ ID NO: 41           moltype = DNA   length = 24
FEATURE                 Location/Qualifiers
source                  1..24
                        mol_type = other DNA
                        organism = synthetic construct
SEQUENCE: 41
agcgggggca gcagcggggg gtca                                                24

SEQ ID NO: 42           moltype = RNA   length = 20
FEATURE                 Location/Qualifiers
source                  1..20
                        mol_type = other RNA
                        organism = synthetic construct
SEQUENCE: 42
ctgcatttat gtcagacttg                                                     20

SEQ ID NO: 43           moltype = RNA   length = 20
FEATURE                 Location/Qualifiers
source                  1..20
                        mol_type = other RNA
                        organism = synthetic construct
SEQUENCE: 43
atatagctaa gatgtcacgg                                                     20

SEQ ID NO: 44           moltype = RNA   length = 20
FEATURE                 Location/Qualifiers
```

```
source                  1..20
                        mol_type = other RNA
                        organism = synthetic construct
SEQUENCE: 44
gaacacaaag catagactgc                                                    20

SEQ ID NO: 45           moltype = RNA  length = 21
FEATURE                 Location/Qualifiers
source                  1..21
                        mol_type = other RNA
                        organism = synthetic construct
SEQUENCE: 45
gcgtgagcgt ggccagcccc a                                                  21

SEQ ID NO: 46           moltype = AA  length = 1569
FEATURE                 Location/Qualifiers
source                  1..1569
                        mol_type = protein
                        organism = synthetic construct
SEQUENCE: 46
MTGSETDHIR WMRHALTLAQ RARDEGEVPV GAVLVLQGQV IGEGWNRAIG LHDPTAHAEM    60
MALRQGGIVL QNYRLLDTTL YVTFEPCVMC AGAMVHSRIG QLIYGVSNSK RGAAGSLMNV   120
LNYPGMNHKV SVAGGVLAQE CAGLLCDFYR MPRQVFNANK QATRQQSINQ SGGSSGGSSG   180
SETPGTSESA TPESSGGSSG GSDKKYSIGL AIGTNSVGWA VITDEYKVPS KKFKVLGNTD   240
RHSIKKNLIG ALLFDSGETA EATRLKRTAR RRYTRRKNRI CYLQEIFSNE MAKVDDSFFH   300
RLEESFLVEE DKKHERHPIF GNIVDEVAYH EKYPTIYHLR KKLVDSTDKA DLRLIYLALA   360
HMIKFRGHFL IEGDLNPDNS DVDKLFIQLV QTYNQLFEEN PINASGVDAK AILSARLSKS   420
RRLENLIAQL PGEKKNGLFG NLIALSLGLT PNFKSNFDLA EDAKLQLSKD TYDDDLDNLL   480
AQIGDQYADL FLAAKNLSDA ILLSDILRVN TEITKAPLSA SMIKRYDEHH QDLTLLKALV   540
RQQLPEKYKE IFFDQSKNGY AGYIDGGASQ EEFYKFIKPI LEKMDGTEEL LVKLNREDLL   600
RKQRTFDNGS IPHQIHLGEL HAILRRQEDF YPFLKDNREK IEKILTFRIP YYVGPLARGN   660
SRFAWMTRKS EETITPWNFE EVVDKGASAQ SFIERMTNPD KNLPNEKVLP KHSLLYEYFT   720
VYNELTKVKY VTEGMRKPAF LSGEQKKAIV DLLFKTNRKV TVKQLKEDYF KKIECFDSVE   780
ISGVEDRFNA SLGTYHDLLK IIKDKDFLDN EENEDILEDI VLTLTLFEDR EMIEERLKTY   840
AHLFDDKVMK QLKRRYTGW GRLSRKLING IRDKQSGKTI LDFLKSDGFA NRNFMQLIHD   900
DSLTFKEDIQ KAQVSGQGDS LHEHIANLAG SPAIKKGILQ TVKVVDELVK VMGRHKPENI   960
VIEMARENQT TQKGQKNSRE RMKRIEEGIK ELGSQILKEH PVENTQLQNE KLYLYYLQNG  1020
RDMYVDQELD INRLSDYDVD HIVPQSFLKD DSIDNKVLTR SDKNRGKSDN VPSEEVVKKM  1080
KNYWRQLLNA KLITQRKFDN LTKAERGGLS ELDKAGFIKR QLVETRQITK HVAQILDSRM  1140
NTKYDENDKL IREVKVITLK SKLVSDFRKD FQFYKVREIN NYHHAHDAYL NAVVGTALIK  1200
KYPKLESEFV YGDYKVYDVR KMIAKSEQEI GKATAKYFFY SNIMNFFKTE ITLANGEIRK  1260
RPLIETNGET GEIVWDKGRD FATVRKVLSM PQVNIVKKTE VQTGGFSKES ILPKRNSDKL  1320
IARKKDWDPK KYGGFDSPTV AYSVLVVAKV EKGKSKKLKS VKELLGITIM ERSSFEKNPI  1380
DPLEAKGYKE VKKDLIIKLP KYSLFELENG RKRMLASAGE LQKGNELALP SKYVNFLYLA  1440
SHYEKLKGSP EDNEQKQLFV EQHKHYLDEI IEQISEFSKR VILADANLDK VLSAYNKHRD  1500
KPIREQAENI IHLFTLTNLG APAAFKYFDT TIDRKRYTST KEVLDATLIH QSITGLYETR  1560
IDLSQLGGD                                                         1569

SEQ ID NO: 47           moltype = AA  length = 1583
FEATURE                 Location/Qualifiers
source                  1..1583
                        mol_type = protein
                        organism = synthetic construct
SEQUENCE: 47
PKKKRKVMTG SETDHIRWMR HALTLAQRAR DEGEVPVGAV LVLQGQVIGE GWNRAIGLHD    60
PTAHAEMMAL RQGGIVLQNY RLLDTTLYVT FEPCVMCAGA MVHSRIGQLI YGVSNSKRGA   120
AGSLMNVLNY PGMNHKVSVA GGVLAQECAG LLCDFYRMPR QVFNANKQAT RQQSINQSGG   180
SSGGSSGSET PGTSESATPE SSGGSSGGSD KKYSIGLAIG TNSVGWAVIT DEYKVPSKKF   240
KVLGNTDRHS IKKNLIGALL FDSGETAEAT RLKRTARRRY TRRKNRICYL QEIFSNEMAK   300
VDDSFFHRLE ESFLVEEDKK HERHPIFGNI VDEVAYHEKY PTIYHLRKKL VDSTDKADLR   360
LIYLALAHMI KFRGHFLIEG DLNPDNSDVD KLFIQLVQTY NQLFEENPIN ASGVDAKAIL   420
SARLSKSRRL ENLIAQLPGE KKNGLFGNLI ALSLGLTPNF KSNFDLAEDA KLQLSKDTYD   480
DDLDNLLAQI GDQYADLFLA AKNLSDAILL SDILRVNTEI TKAPLSASMI KRYDEHHQDL   540
TLLKALVRQQ LPEKYKEIFF DQSKNGYAGY IDGGASQEEF YKFIKPILEK MDGTEELLVK   600
LNREDLLRKQ RTFDNGSIPH QIHLGELHAI LRRQEDFYPF LKDNREKIEK ILTFRIPYYV   660
GPLARGNSRF AWMTRKSEET ITPWNFEEVV DKGASAQSFI ERMTNFDKNL PNEKVLPKHS   720
LLYEYFTVYN ELTKVKYVTE GMRKPAFLSG EQKKAIVDLL FKTNRKVTVK QLKEDYFKKI   780
ECFDSVEISG VEDRFNASLG TYHDLLKIIK DKDFLDNEEN EDILEDIVLT LTLFEDREMI   840
EERLKTYAHL FDDKVMKQLK RRYTGWGRL SRKLINGIRD KQSGKTILDF LKSDGFANRN   900
FMQLIHDDSL TFKEDIQKAQ VSGQGDSLHE HIANLAGSPA IKKGILQTVK VVDELVKVMG   960
RHKPENIVIE MARENQTTQK GQKNSRERMK RIEEGIKELG SQILKEHPVE NTQLQNEKLY  1020
LYYLQNGRDM YVDQELDINR LSDYDVDHIV PQSFLKDDSI DNKVLTRSDK NRGKSDNVPS  1080
EEVVKKMKNY WRQLLNAKLI TQRKFDNLTK AERGGLSELD KAGFIKRQLV ETRQITKHVA  1140
QILDSRMNTK YDENDKLIRE VKVITLKSKL VSDFRKDFQF YKVREINNYH HAHDAYLNAV  1200
VGTALIKKYP KLESEFVYGD YKVYDVRKMI AKSEQEIGKA TAKYFFYSNI MNFFKTEITL  1260
ANGEIRKRPL IETNGETGEI VWDKGRDFAT VRKVLSMPQV NIVKKTEVQT GGFSKESILP  1320
KRNSDKLIAR KKDWDPKKYG GFDSPTVAYS VLVVAKVEKG KSKKLKSVKE LLGITIMERS  1380
SFEKNPIDFL EAKGYKEVKK DLIIKLPKYS LFELENGRKR MLASAGELQK GNELALPSKY  1440
VNFLYLASHY EKLKGSPEDN EQKQLFVEQH KHYLDEIIEQ ISEFSKRVIL ADANLDKVLS  1500
```

```
SEQ ID NO: 48          moltype = AA   length = 1587
FEATURE                Location/Qualifiers
source                 1..1587
                       mol_type = protein
                       organism = synthetic construct
SEQUENCE: 48
PKKKRKVMTG SETDHIRWMR HALTLAQRAR DEGEVPVGAV LVLQGQVIGE GWNRAIGLHD   60
PTAHAEMMAL RQGGIVLQNY RLLDTTLYVT FEPCVMCAGA MVHSRIGQLI YGVSNSKRGA  120
AGSLMNVLNY PGMNHKVSVA GGVLAQECAG LLCDFYRMPR QVFNANKQAT RQQSINQSGG  180
SSGGSSGSET PGTSESATPE SSGGSSGGSD KKYSIGLAIG TNSVGWAVIT DEYKVPSKKF  240
KVLGNTDRHS IKKNLIGALL FDSGETAEAT RLKRTARRRY TRRKNRICYL QEIFSNEMAK  300
VDDSFFHRLE ESFLVEEDKK HERHPIFGNI VDEVAYHEKY PTIYHLRKKL VDSTDKADLR  360
LIYLALAHMI KFRGHFLIEG DLNPDNSDVD KLFIQLVQTY NQLFEENPIN ASGVDAKAIL  420
SARLSKSRRL ENLIAQLPGE KKNGLFGNLI ALSLGLTPNF KSNFDLAEDA KLQLSKDTYD  480
DDLDNLLAQI GDQYADLFLA AKNLSDAILL SDILRVNTEI TKAPLSASMI KRYDEHHQDL  540
TLLKALVRQQ LPEKYKEIFF DQSKNGYAGY IDGGASQEEF YKFIKPILEK MDGTEELLVK  600
LNREDLLRKQ RTFDNGSIPH QIHLGELHAI LRRQEDFYPF LKDNREKIEK ILTFRIPYYV  660
GPLARGNSRF AWMTRKSEET ITPWNFEEVV DKGASAQSFI ERMTNFDKNL PNEKVLPKHS  720
LLYEYFTVYN ELTKVKYVTE GMRKPAFLSG EQKKAIVDLL FKTNRKVTVK QLKEDYFKKI  780
ECFDSVEISG VEDRFNASLG TYHDLLKIIK DKDFLDNEEN EDILEDIVLT LTLFEDREMI  840
EERLKTYAHL FDDKVMKQLK RRRYTGWGRL SRKLINGIRD KQSGKTILDF LKSDGFANRN  900
FMQLIHDDSL TFKEDIQKAQ VSGQGDSLHE HIANLAGSPA IKKGILQTVK VVDELVKVMG  960
RHKPENIVIE MARENQTTQK GQKNSRERMK RIEEGIKELG SQILKEHPVE NTQLQNEKLY 1020
LYYLQNGRDM YVDQELDINR LSDYDVDAIV PQSFLKDDSI DNKVLTRSDK NRGKSDNVPS 1080
EEVVKKMKNY WRQLLNAKLI TQRKFDNLTK AERGGLSELD KAGFIKRQLV ETRQITKHVA 1140
QILDSRMNTK YDENDKLIRE VKVITLKSKL VSDFRKDFQF YKVREINNYH HAHDAYLNAV 1200
VGTALIKKYP KLESEFVYGD YKVYDVRKMI AKSEQEIGKA TAKYFFYSNI MNFFKTEITL 1260
ANGEIRKRPL IETNGETGEI VWDKGRDFAT VRKVLSMPQV NIVKKTEVQT GGFSKESILP 1320
KRNSDKLIAR KKDWDPKKYG GFDSPTVAYS VLVVAKVEKG KSKKLKSVKE LLGITIMERS 1380
SFEKNPIDFL EAKGYKEVKK DLIIKLPKYS LFELENGRKR MLASAGELQK GNELALPSKY 1440
VNFLYLASHY EKLKGSPEDN EQKQLFVEQH KHYLDEIIEQ ISEFSKRVIL ADANLDKVLS 1500
AYNKHRDKPI REQAENIIHL FTLTNLGAPA AFKYFDTTID RKRYTSTKEV LDATLIHQSI 1560
TGLYETRIDL SQLGGDSGGS PKKKRKV                                    1587

SEQ ID NO: 49          moltype = AA   length = 1568
FEATURE                Location/Qualifiers
source                 1..1568
                       mol_type = protein
                       organism = synthetic construct
SEQUENCE: 49
MSELYSDEYW MEQALERAKR ARQQNEIPVG AVVLNNQII GEGWNQAITL HNPTAHAEIM   60
ALEEAGLSQQ NYRLVGATLY VTFEPCMMCA GAIIHSRIER LVYGVSNVKR GAAGSFINLL  120
NYPGINHCVQ ISSGVLQEQC SSLLCEFYRR PRQVINQQKK SQESLLINSS GGSSGGSSGS  180
ETPGTSESAT PESSGGSSGG SDKKYSIGLA IGTNSVGWAV ITDEYKVPSK KFKVLGNTDR  240
HSIKKNLIGA LLFDSGETAE ATRLKRTARR RYTRRKNRIC YLQEIFSNEM AKVDDSFFHR  300
LEESFLVEED KKHERHPIFG NIVDEVAYHE KYPTIYHLRK KLVDSTDKAD LRLIYLALAH  360
MIKFRGHFLI EGDLNPDNSD VDKLFIQLVQ TYNQLFEENP INASGVDAKA ILSARLSKSR  420
RLENLIAQLP GEKKNGLFGN LIALSLGLTP NFKSNFDLAE DAKLQLSKDT YDDDLDNLLA  480
QIGDQYADLF LAAKNLSDAI LLSDILRVNT EITKAPLSAS MIKRYDEHHQ DLTLLKALVR  540
QQLPEKYKEI FFDQSKNGYA GYIDGGASQE EFYKFIKPIL EKMDGTEELL VKLNREDLLR  600
KQRTFDNGSI PHQIHLGELH AILRRQEDFY PFLKDNREKI EKILTFRIPY YVGPLARGNS  660
RFAWMTRKSE ETITPWNFEE VVDKGASAQS FIERMTNFDK NLPNEKVLPK HSLLYEYFTV  720
YNELTKVKYV TEGMRKPAFL SGEQKKAIVD LLFKTNRKVT VKQLKEDYFK KIECFDSVEI  780
SGVEDRFNAS LGTYHDLLKI IKDKDFLDNE ENEDILEDIV LTLTLFEDRE MIEERLKTYA  840
HLFDDKVMKQ LKRRRYTGWG RLSRKLINGI RDKQSGKTIL DFLKSDGFAN RNFMQLIHDD  900
SLTFKEDIQK AQVSGQGDSL HEHIANLAGS PAIKKGILQT VKVVDELVKV MGRHKPENIV  960
IEMARENQTT QKGQKNSRER MKRIEEGIKE LGSQILKEHP VENTQLQNEK LYLYYLQNGR 1020
DMYVDQELDI NRLSDYDVDH IVPQSFLKDD SIDNKVLTRS DKNRGKSDNV PSEEVVKKMK 1080
NYWRQLLNAK LITQRKFDNL TKAERGGLSE LDKAGFIKRQ LVETRQITKH VAQILDSRMN 1140
TKYDENDKLI REVKVITLKS KLVSDFRKDF QFYKVREINN YHHAHDAYLN AVVGTALIKK 1200
YPKLESEFVY GDYKVYDVRK MIAKSEQEIG KATAKYFFYS NIMNFFKTEI TLANGEIRKR 1260
PLIETNGETG EIVWDKGRDF ATVRKVLSMP QVNIVKKTEV QTGGFSKESI LPKRNSDKLI 1320
ARKKDWDPKK YGGFDSPTVA YSVLVVAKVE KGKSKKLKSV KELLGITIME RSSFEKNPID 1380
FLEAKGYKEV KKDLIIKLPK YSLFELENGR KRMLASAGEL QKGNELALPS KYVNFLYLAS 1440
HYEKLKGSPE DNEQKQLFVE QHKHYLDEII EQISEFSKRV ILADANLDKV LSAYNKHRDK 1500
PIREQAENII HLFTLTNLGA PAAFKYFDTT IDRKRYTSTK EVLDATLIHQ SITGLYETRI 1560
DLSQLGGD                                                        1568

SEQ ID NO: 50          moltype = AA   length = 1566
FEATURE                Location/Qualifiers
source                 1..1566
                       mol_type = protein
                       organism = synthetic construct
SEQUENCE: 50
PKKKRKVMSE LYSDEYWMEQ ALERAKRARQ QNEIPVGAVV LNNQIIGEG WNQAITLHNP    60
TAHAEIMALE EAGLSQQNYR LVGATLYVTF EPCMMCAGAI IHSRIERLVY GVSNVKRGAA  120
```

```
GSFINLLNYP GINHCVQISS GVLQEQCSSL LCEFYRRPRQ VINQQKKSQE SLLINSSGSE  180
TPGTSESATP ESDKKYSIGL AIGTNSVGWA VITDEYKVPS KKFKVLGNTD RHSIKKNLIG  240
ALLFDSGETA EATRLKRTAR RRYTRRKNRI CYLQEIFSNE MAKVDDSFFH RLEESFLVEE  300
DKKHERHPIF GNIVDEVAYH EKYPTIYHLR KKLVDSTDKA DLRLIYLALA HMIKFRGHFL  360
IEGDLNPDNS DVDKLFIQLV QTYNQLFEEN PINASGVDAK AILSARLSKS RRLENLIAQL  420
PGEKKNGLFG NLIALSLGLT PNFKSNFDLA EDAKLQLSKD TYDDDLDNLL AQIGDQYADL  480
FLAAKNLSDA ILLSDILRVN TEITKAPLSA SMIKRYDEHH QDLTLLKALV RQQLPEKYKE  540
IFFDQSKNGY AGYIDGGASQ EEFYKFIKPI LEKMDGTEEL LVKLNREDLL RKQRTFDNGS  600
IPHQIHLGEL HAILRRQEDF YPFLKDNREK IEKILTFRIP YYVGPLARGN SRFAWMTRKS  660
EETITPWNFE EVVDKGASAQ SFIERMTNFD KNLPNEKVLP KHSLLYEYFT VYNELTKVKY  720
VTEGMRKPAF LSGEQKKAIV DLLFKTNRKV TVKQLKEDYF KKIECFDSVE ISGVEDRFNA  780
SLGTYHDLLK IIKDKDFLDN EENEDILEDI VLTLTLFEDR EMIEERLKTY AHLFDDKVMK  840
QLKRRRYTGW GRLSRKLING IRDKQSGKTI LDFLKSDGFA NRNFMQLIHD DSLTFKEDIQ  900
KAQVSGQGDS LHEHIANLAG SPAIKKGILQ TVKVVDELVK VMGRHKPENI VIEMARENQT  960
TQKGQKNSRE RMKRIEEGIK ELGSQILKEH PVENTQLQNE KLYLYYLQNG RDMYVDQELD 1020
INRLSDYDVD HIVPQSFLKD DSIDNKVLTR SDKNRGKSDN VPSEEVVKKM KNYWRQLLNA 1080
KLITQRKFDN LTKAERGGLS ELDKAGFIKR QLVETRQITK HVAQILDSRM NTKYDENDKL 1140
IREVKVITLK SKLVSDFRKD FQFYKVREIN NYHHAHDAYL NAVVGTALIK KYPKLESEFV 1200
YGDYKVYDVR KMIAKSEQEI GKATAKYFFY SNIMNFFKTE ITLANGEIRK RPLIETNGET 1260
GEIVWDKGRD FATVRKVLSM PQVNIVKKTE VQTGGFSKES ILPKRNSDKL IARKKDWDPK 1320
KYGGFDSPTV AYSVLVVAKV EKGKSKKLKS VKELLGITIM ERSSFEKNPI DFLEAKGYKE 1380
VKKDLIIKLP KYSLFELENG RKRMLASAGE LQKGNELALP SKYVNFLYLA SHYEKLKGSP 1440
EDNEQKQLFV EQHKHYLDEI IEQISEFSKR VILADANLDK VLSAYNKHRD KPIREQAENI 1500
IHLFTLTNLG APAAFKYFDT TIDRKRYTST KEVLDATLIH QSITGLYETR IDLSQLGGDP 1560
KKKRKV                                                          1566

SEQ ID NO: 51          moltype = AA  length = 1586
FEATURE                Location/Qualifiers
source                 1..1586
                       mol_type = protein
                       organism = synthetic construct
SEQUENCE: 51
PKKKRKVMSE LYSDEYWMEQ ALERAKRARQ QNEIPVGAVV VLNNQIIGEG WNQAITLHNP   60
TAHAEIMALE EAGLSQQNYR LVGATLYVTF EPCMMCAGAI IHSRIERLVY GVSNVKRGAA  120
GSFINLLNYP GINHCVQISS GVLQEQCSSL LCEFYRRPRQ VINQQKKSQE SLLINSSGGS  180
SGGSSGGSETP GTSESATPES SGGSSGGSDK KYSIGLAIGT NSVGWAVITD EYKVPSKKFK  240
VLGNTDRHSI KKNLIGALLF DSGETAEATR LKRTARRRYT RRKNRICYLQ EIFSNEMAKV  300
DDSFFHRLEE SFLVEEDKKH ERHPIFGNIV DEVAYHEKYP TIYHLRKKLV DSTDKADLRL  360
IYLALAHMIK FRGHFLIEGD LNPDNSDVDK LFIQLVQTYN QLFEENPINA SGVDAKAILS  420
ARLSKSRRLE NLIAQLPGEK KNGLFGNLIA LSLGLTPNFK SNFDLAEDAK LQLSKDTYDD  480
DLDNLLAQIG DQYADLFLAA KNLSDAILLS DILRVNTEIT KAPLSASMIK RYDEHHQDLT  540
LLKALVRQQL PEKYKEIFFD QSKNGYAGYI DGGASQEEFY KFIKPILEKM DGTEELLVKL  600
NREDLLRKQR TFDNGSIPHQ IHLGELHAIL RRQEDFYPFL KDNREKIEKI LTFRIPYYVG  660
PLARGNSRFA WMTRKSEETI TPWNFEEVVD KGASAQSFIE RMTNFDKNLP NEKVLPKHSL  720
LYEYFTVYNE LTKVKYVTEG MRKPAFLSGE QKKAIVDLLF KTNRKVTVKQ LKEDYFKKIE  780
CFDSVEISGV EDRFNASLGT YHDLLKIIKD KDFLDNEENE DILEDIVLTL TLFEDREMIE  840
ERLKTYAHLF DDKVMKQLKR RRYTGWGRLS RKLINGIRDK QSGKTILDFL KSDGFANRNF  900
MQLIHDDSLT FKEDIQKAQV SGQGDSLHEH IANLAGSPAI KKGILQTVKV VDELVKVMGR  960
HKPENIVIEM ARENQTTQKG QKNSRERMKR IEEGIKELGS QILKEHPVEN TQLQNEKLYL 1020
YYLQNGRDMY VDQELDINRL SDYDVDAIVP QSFLKDDSID NKVLTRSDKN RGKSDNVPSE 1080
EVVKKMKNYW RQLLNAKLIT QRKFDNLTKA ERGGLSELDK AGFIKRQLVE TRQITKHVAQ 1140
ILDSRMNTKY DENDKLIREV KVITLKSKLV SDFRKDFQFY KVREINNYHH AHDAYLNAVV 1200
GTALIKKYPK LESEFVYGDY KVYDVRKMIA KSEQEIGKAT AKYFFYSNIM NFFKTEITLA 1260
NGEIRKRPLI ETNGETGEIV WDKGRDFATV RKVLSMPQVN IVKKTEVQTG GFSKESILPK 1320
RNSDKLIARK KDWDPKKYGG FDSPTVAYSV LVVAKVEKGK SKKLKSVKEL LGITIMERSS 1380
FEKNPIDFLE AKGYKEVKKD LIIKLPKYSL FELENGRKRM LASAGELQKG NELALPSKYV 1440
NFLYLASHYE KLKGSPEDNE QKQLFVEQHK HYLDEIIEQI SEFSKRVILA DANLDKVLSA 1500
YNKHRDKPIR EQAENIIHLF TLTNLGAPAA FKYFDTTIDR KRYTSTKEVL DATLIHQSIT 1560
GLYETRIDLS QLGGDSGGSP KKKRKV                                    1586

SEQ ID NO: 52          moltype = AA  length = 1569
FEATURE                Location/Qualifiers
source                 1..1569
                       mol_type = protein
                       organism = synthetic construct
SEQUENCE: 52
MSDTQIDEKW MRHALTLARR AREEGEVPVG AVLVLGDTVI GEGWNRAIGL HDPTAHAEIM   60
ALRQGGKVLE NYRLLDTTLY VTFEPCVMCA GAMVHGRVGR LVPGVRNSKR GAAGSLLNIL  120
NYAGMNHQVS VEQGVLAAEC AAMLCNFYRQ PRAVFNALRD RLRAELLKIN SGGSSGGSSG  180
SETPGTSESA TPESSGGSSG GSDKKYSIGL AIGTNSVGWA VITDEYKVPS KKFKVLGNTD  240
RHSIKKNLIG ALLFDSGETA EATRLKRTAR RRYTRRKNRI CYLQEIFSNE MAKVDDSFFH  300
RLEESFLVEE DKKHERHPIF GNIVDEVAYH EKYPTIYHLR KKLVDSTDKA DLRLIYLALA  360
HMIKFRGHFL IEGDLNPDNS DVDKLFIQLV QTYNQLFEEN PINASGVDAK AILSARLSKS  420
RRLENLIAQL PGEKKNGLFG NLIALSLGLT PNFKSNFDLA EDAKLQLSKD TYDDDLDNLL  480
AQIGDQYADL FLAAKNLSDA ILLSDILRVN TEITKAPLSA SMIKRYDEHH QDLTLLKALV  540
RQQLPEKYKE IFFDQSKNGY AGYIDGGASQ EEFYKFIKPI LEKMDGTEEL LVKLNREDLL  600
RKQRTFDNGS IPHQIHLGEL HAILRRQEDF YPFLKDNREK IEKILTFRIP YYVGPLARGN  660
SRFAWMTRKS EETITPWNFE EVVDKGASAQ SFIERMTNFD KNLPNEKVLP KHSLLYEYFT  720
VYNELTKVKY VTEGMRKPAF LSGEQKKAIV DLLFKTNRKV TVKQLKEDYF KKIECFDSVE  780
```

```
ISGVEDRFNA SLGTYHDLLK IIKDKDFLDN EENEDILEDI VLTLTLFEDR EMIEERLKTY    840
AHLFDDKVMK QLKRRRYTGW GRLSRKLING IRDKQSGKTI LDFLKSDGFA NRNFMQLIHD    900
DSLTFKEDIQ KAQVSGQGDS LHEHIANLAG SPAIKKGILQ TVKVVDELVK VMGRHKPENI    960
VIEMARENQT TQKGQKNSRE RMKRIEEGIK ELGSQILKEH PVENTQLQNE KLYLYYLQNG   1020
RDMYVDQELD INRLSDYDVD HIVPQSFLKD DSIDNKVLTR SDKNRGKSDN VPSEEVVKKM   1080
KNYWRQLLNA KLITQRKFDN LTKAERGGLS ELDKAGFIKR QLVETRQITK HVAQILDSRM   1140
NTKYDENDKL IREVKVITLK SKLVSDFRKD FQFYKVREIN NYHHAHDAYL NAVVGTALIK   1200
KYPKLESEFV YGDYKVYDVR KMIAKSEQEI GKATAKYFFY SNIMNFFKTE ITLANGEIRK   1260
RPLIETNGET GEIVWDKGRD FATVRKVLSM PQVNIVKKTE VQTGGFSKES ILPKRNSDKL   1320
IARKKDWDPK KYGGFDSPTV AYSVLVVAKV EKGKSKKLKS VKELLGITIM ERSSFEKNPI   1380
DFLEAKGYKE VKKDLIIKLP KYSLFELENG RKRMLASAGE LQKGNELALP SKYVNFLYLA   1440
SHYEKLKGSP EDNEQKQLFV EQHKHYLDEI IEQISEFSKR VILADANLDK VLSAYNKHRD   1500
KPIREQAENI IHLFTLTNLG APAAFKYFDT TIDRKRYTST KEVLDATLIH QSITGLYETR   1560
IDLSQLGGD                                                          1569

SEQ ID NO: 53          moltype = AA   length = 1567
FEATURE                Location/Qualifiers
source                 1..1567
                       mol_type = protein
                       organism = synthetic construct
SEQUENCE: 53
PKKKRKVMSD TQIDEKWMRH ALTLARRARE EGEVPVGAVL VLGDTVIGEG WNRAIGLHDP    60
TAHAEIMALR QGGKVLENYR LLDTTLYVTF EPCVMCAGAM VHGRVGRLVF GVRNSKRGAA   120
GSLLNILNYA GMNHQVSVEQ GVLAAECAAM LCNFYRQPRA VFNALRDRLR AELLKINSGS   180
ETPGTSESAT PESDKKYSIG LAIGTNSVGW AVITDEYKVP SKKFKVLGNT DRHSIKKNLI   240
GALLFDSGET AEATRLKRTA RRRYTRRKNR ICYLQEIFSN EMAKVDDSFF HRLEESFLVE   300
EDKKHERHPI FGNIVDEVAY HEKYPTIYHL RKKLVDSTDK ADLRLIYLAL AHMIKFRGHF   360
LIEGDLNPDN SDVDKLFIQL VQTYNQLFEE NPINASGVDA KAILSARLSK SRRLENLIAQ   420
LPGEKKNGLF GNLIALSLGL TPNFKSNFDL AEDAKLQLSK DTYDDDLDNL LAQIGDQYAD   480
LFLAAKNLSD AILLSDILRV NTEITKAPLS ASMIKRYDEH HQDLTLLKAL VRQQLPEKYK   540
EIFFDQSKNG YAGYIDGGAS QEEFYKFIKP ILEKMDGTEE LLVKLNREDL LRKQRTFDNG   600
SIPHQIHLGE LHAILRRQED FYPFLKDNRE KIEKILTFRI PYYVGPLARG NSRFAWMTRK   660
SEETITPWNF EEVVDKGASA QSFIERMTNF DKNLPNEKVL PKHSLLYEYF TVYNELTKVK   720
YVTEGMRKPA FLSGEQKKAI VDLLFKTNRK VTVKQLKEDY FKKIECFDSV EISGVEDRFN   780
ASLGTYHDLL KIIKDKDFLD NEENEDILED IVLTLTLFED REMIEERLKT YAHLFDDKVM   840
KQLKRRRYTG WGRLSRKLIN GIRDKQSGKT ILDFLKSDGF ANRNFMQLIH DDSLTFKEDI   900
QKAQVSGQGD SLHEHIANLA GSPAIKKGIL QTVKVVDELV KVMGRHKPEN IVIEMARENQ   960
TTQKGQKNSR ERMKRIEEGI KELGSQILKE HPVENTQLQN EKLYLYYLQN GRDMYVDQEL  1020
DINRLSDYDV DHIVPQSFLK DDSIDNKVLT RSDKNRGKSD NVPSEEVVKK MKNYWRQLLN  1080
AKLITQRKFD NLTKAERGGL SELDKAGFIK RQLVETRQIT KHVAQILDSR MNTKYDENDK  1140
LIREVKVITL KSKLVSDFRK DFQFYKVREI NNYHHAHDAY LNAVVGTALI KKYPKLESEF  1200
VYGDYKVYDV RKMIAKSEQE IGKATAKYFF YSNIMNFFKT EITLANGEIR KRPLIETNGE  1260
TGEIVWDKGR DFATVRKVLS MPQVNIVKKT EVQTGGFSKE SILPKRNSDK LIARKKDWDP  1320
KKYGGFDSPT VAYSVLVVAK VEKGKSKKLK SVKELLGITI MERSSFEKNP IDFLEAKGYK  1380
EVKKDLIIKL PKYSLFELEN GRKRMLASAG ELQKGNELAL PSKYVNFLYL ASHYEKLKGS  1440
PEDNEQKQLF VEQHKHYLDE IIEQISEFSK RVILADANLD KVLSAYNKHR DKPIREQAEN  1500
IIHLFTLTNL GAPAAFKYFD TTIDRKRYTS TKEVLDATLI HQSITGLYET RIDLSQLGGD  1560
PKKKRKV                                                           1567

SEQ ID NO: 54          moltype = AA   length = 1587
FEATURE                Location/Qualifiers
source                 1..1587
                       mol_type = protein
                       organism = synthetic construct
SEQUENCE: 54
PKKKRKVMSD TQIDEKWMRH ALTLARRARE EGEVPVGAVL VLGDTVIGEG WNRAIGLHDP    60
TAHAEIMALR QGGKVLENYR LLDTTLYVTF EPCVMCAGAM VHGRVGRLVF GVRNSKRGAA   120
GSLLNILNYA GMNHQVSVEQ GVLAAECAAM LCNFYRQPRA VFNALRDRLR AELLKINSGG   180
SSGGSGSET PGTSESATPE SSGGSSGGSD KKYSIGLAIG TNSVGWAVIT DEYKVPSKKF   240
KVLGNTDRHS IKKNLIGALL FDSGETAEAT RLKRTARRRY TRRKNRICYL QEIFSNEMAK   300
VDDSFFHRLE ESFLVEEDKK HERHPIFGNI VDEVAYHEKY PTIYHLRKKL VDSTDKADLR   360
LIYLALAHMI KFRGHFLIEG DLNPDNSDVD KLFIQLVQTY NQLFEENPIN ASGVDAKAIL   420
SARLSKSRRL ENLIAQLPGE KKNGLFGNLI ALSLGLTPNF KSNFDLAEDA KLQLSKDTYD   480
DDLDNLLAQI GDQYADLFLA AKNLSDAILL SDILRVNTEI TKAPLSASMI KRYDEHHQDL   540
TLLKALVRQQ LPEKYKEIFF DQSKNGYAGY IDGGASQEEF YKFIKPILEK MDGTEELLVK   600
LNREDLLRKQ RTFDNGSIPH QIHLGELHAI LRRQEDFYPF LKDNREKIEK ILTFRIPYYV   660
GPLARGNSRF AWMTRKSEET ITPWNFEEVV DKGASAQSFI ERMTNFDKNL PNEKVLPKHS   720
LLYEYFTVYN ELTKVKYVTE GMRKPAFLSG EQKKAIVDLL FKTNRKVTVK QLKEDYFKKI   780
ECFDSVEISG VEDRFNASLG TYHDLLKIIK DKDFLDNEEN EDILEDIVLT LTLFEDREMI   840
EERLKTYAHL FDDKVMKQLK RRRYTGWGRL SRKLINGIRD KQSGKTILDF LKSDGFANRN   900
FMQLIHDDSL TFKEDIQKAQ VSGQGDSLHE HIANLAGSPA IKKGILQTVK VVDELVKVMG   960
RHKPENIVIE MARENQTTQK GQKNSRERMK RIEEGIKELG SQILKEHPVE NTQLQNEKLY  1020
LYYLQNGRDM YVDQELDINR LSDYDVDAIV PQSFLKDDSI DNKVLTRSDK NRGKSDNVPS  1080
EEVVKKMKNY WRQLLNAKLI TQRKFDNLTK AERGGLSELD KAGFIKRQLV ETRQITKHVA  1140
QILDSRMNTK YDENDKLIRE VKVITLKSKL VSDFRKDFQF YKVREINNYH HAHDAYLNAV  1200
VGTALIKKYP KLESEFVYGD YKVYDVRKMI AKSEQEIGKA TAKYFFYSNI MNFFKTEITL  1260
ANGEIRKRPL IETNGETGEI VWDKGRDFAT VRKVLSMPQV NIVKKTEVQT GGFSKESILP  1320
KRNSDKLIAR KKDWDPKKYG GFDSPTVAYS VLVVAKVEKG KSKKLKSVKE LLGITIMERS  1380
SFEKNPIDFL EAKGYKEVKK DLIIKLPKYS LFELENGRKR MLASAGELQK GNELALPSKY  1440
```

```
VNFLYLASHY EKLKGSPEDN EQKQLFVEQH KHYLDEIIEQ ISEFSKRVIL ADANLDKVLS    1500
AYNKHRDKPI REQAENIIHL FTLTNLGAPA AFKYFDTTID RKRYTSTKEV LDATLIHQSI    1560
TGLYETRIDL SQLGGDSGGS PKKKRKV                                       1587

SEQ ID NO: 55              moltype = DNA  length = 95
FEATURE                    Location/Qualifiers
source                     1..95
                           mol_type = other DNA
                           organism = synthetic construct
SEQUENCE: 55
ctctactgtt tctccatacc cgttttttg gacgcgtaca ccccaagtct gacataaatg     60
cagtttaagg tttacaccta taaaagagag agccg                              95

SEQ ID NO: 56              moltype = DNA  length = 95
FEATURE                    Location/Qualifiers
source                     1..95
                           mol_type = other DNA
                           organism = synthetic construct
SEQUENCE: 56
gagatgacaa agaggtatgg gcaaaaaaac ctgcgcatgt ggggttcaga ctgtatttac    60
gtcaaattcc aaatgtggat attttctctc tcggc                              95

SEQ ID NO: 57              moltype = DNA  length = 92
FEATURE                    Location/Qualifiers
source                     1..92
                           mol_type = other DNA
                           organism = synthetic construct
SEQUENCE: 57
ctctactgtt tctccatacc cgttttttg gacgcgtaca ccccaagtct gacacaaacg     60
tttaaggttt acacctataa aagagagagc cg                                 92

SEQ ID NO: 58              moltype = DNA  length = 95
FEATURE                    Location/Qualifiers
source                     1..95
                           mol_type = other DNA
                           organism = synthetic construct
SEQUENCE: 58
ctctactgtt tctccatacc cgttttttg gacgcgtaca ccccaagtct gacacaaacg     60
cagtttaagg tttacaccta taaaagagag agccg                              95

SEQ ID NO: 59              moltype = DNA  length = 94
FEATURE                    Location/Qualifiers
source                     1..94
                           mol_type = other DNA
                           organism = synthetic construct
SEQUENCE: 59
ctctactgtt tctccatacc cgttttttg gacgcgtaca ccccaagtct gacataaatg     60
cagtttaagg tttacaccta taaaagagag agcc                               94

SEQ ID NO: 60              moltype = DNA  length = 94
FEATURE                    Location/Qualifiers
source                     1..94
                           mol_type = other DNA
                           organism = synthetic construct
SEQUENCE: 60
ctctactgtt tctccatacc cgttttttg gacgcgtaca ccccaagtct gacataacgc     60
agtttaaggt ttacacctat aaaagagaga gccg                               94

SEQ ID NO: 61              moltype = DNA  length = 44
FEATURE                    Location/Qualifiers
source                     1..44
                           mol_type = other DNA
                           organism = synthetic construct
SEQUENCE: 61
ggacgcgtac accccaagtc tgacataaat gcagtttaag gttt                    44

SEQ ID NO: 62              moltype = DNA  length = 44
FEATURE                    Location/Qualifiers
source                     1..44
                           mol_type = other DNA
                           organism = synthetic construct
SEQUENCE: 62
cctgcgcatg tggggttcag actgtattta cgtcaaattc caaa                    44

SEQ ID NO: 63              moltype = DNA  length = 56
FEATURE                    Location/Qualifiers
source                     1..56
                           mol_type = other DNA
                           organism = synthetic construct
```

-continued

```
SEQUENCE: 63
attaacctga tgttctgggg aatatagcta agatgtcacg gaggtctaga cgggga        56

SEQ ID NO: 64           moltype = DNA   length = 56
FEATURE                 Location/Qualifiers
source                  1..56
                        mol_type = other DNA
                        organism = synthetic construct
SEQUENCE: 64
taattggact acaagacccc ttatatcgat tctacagtgc ctccagatct gccccct       56

SEQ ID NO: 65           moltype = DNA   length = 57
FEATURE                 Location/Qualifiers
source                  1..57
                        mol_type = other DNA
                        organism = synthetic construct
SEQUENCE: 65
attaacctga tgttctgggg aatatagcta agatgtcacg gaggtctaga cggggag       57

SEQ ID NO: 66           moltype = DNA   length = 57
FEATURE                 Location/Qualifiers
source                  1..57
                        mol_type = other DNA
                        organism = synthetic construct
SEQUENCE: 66
attaacctga tgttctgggg aatatagcta agatgtcacg gaggtctaga cggggag       57

SEQ ID NO: 67           moltype = DNA   length = 56
FEATURE                 Location/Qualifiers
source                  1..56
                        mol_type = other DNA
                        organism = synthetic construct
SEQUENCE: 67
attaacctga tgttctgggg aatgtggcta agatgtcacg gaggtctaga cgggga        56

SEQ ID NO: 68           moltype = DNA   length = 98
FEATURE                 Location/Qualifiers
source                  1..98
                        mol_type = other DNA
                        organism = synthetic construct
SEQUENCE: 68
ctctctactg tttctccata cccgtttttt tggacgcgta caccccaagt ctgacataaa    60
tgcagtttaa ggtttacacc tataaaagag agagccgt                            98

SEQ ID NO: 69           moltype = DNA   length = 98
FEATURE                 Location/Qualifiers
source                  1..98
                        mol_type = other DNA
                        organism = synthetic construct
SEQUENCE: 69
gagagatgac aaagaggtat gggcaaaaaa acctgcgcat gtggggttca gactgtattt    60
acgtcaaatt ccaaatgtgg atattttctc tctcggca                            98

SEQ ID NO: 70           moltype = DNA   length = 96
FEATURE                 Location/Qualifiers
source                  1..96
                        mol_type = other DNA
                        organism = synthetic construct
SEQUENCE: 70
ctctactgtt tctccatacc cgttttttg gacgcgtaca ccccaagtct gacaccaaac     60
gcagtttaag gtttacacct ataaagaga gagccg                               96

SEQ ID NO: 71           moltype = DNA   length = 98
FEATURE                 Location/Qualifiers
source                  1..98
                        mol_type = other DNA
                        organism = synthetic construct
SEQUENCE: 71
ctctctactg tttctccata cccgtttttt tggacgcgta caccccaagt ctgacataaa    60
cgcagtttaa ggtttacacc tataaaagag agagccgt                            98

SEQ ID NO: 72           moltype = DNA   length = 98
FEATURE                 Location/Qualifiers
source                  1..98
                        mol_type = other DNA
                        organism = synthetic construct
SEQUENCE: 72
ctctctactg tttctccata cccgtttttt tggacgcgta caccccaagt ctgacacaaa    60
cgcagtttaa ggtttacacc tataaaagag agagccgt                            98
```

```
SEQ ID NO: 73          moltype = AA  length = 12
FEATURE                Location/Qualifiers
source                 1..12
                       mol_type = protein
                       organism = synthetic construct
SEQUENCE: 73
MQFKVYTYKR ES                                                         12

SEQ ID NO: 74          moltype = DNA  length = 98
FEATURE                Location/Qualifiers
source                 1..98
                       mol_type = other DNA
                       organism = synthetic construct
SEQUENCE: 74
ctctctactg tttctccata cccgtttttt tggacgcgta caccccaagt ctgacataaa     60
cacagtttaa ggtttacacc tataaaagag agagccgt                             98

SEQ ID NO: 75          moltype = DNA  length = 98
FEATURE                Location/Qualifiers
source                 1..98
                       mol_type = other DNA
                       organism = synthetic construct
SEQUENCE: 75
ctctctactg tttctccata cccgtttttt tggacgcgta caccccaagt ctgacacaaa     60
cacagtttaa ggtttacacc tataaaagag agagccgt                             98

SEQ ID NO: 76          moltype = AA  length = 13
FEATURE                Location/Qualifiers
source                 1..13
                       mol_type = protein
                       organism = synthetic construct
SEQUENCE: 76
MQFKVYTYKR ESR                                                        13

SEQ ID NO: 77          moltype = AA  length = 5
FEATURE                Location/Qualifiers
source                 1..5
                       mol_type = protein
                       organism = synthetic construct
SEQUENCE: 77
MQFKV                                                                  5

SEQ ID NO: 78          moltype = DNA  length = 44
FEATURE                Location/Qualifiers
source                 1..44
                       mol_type = other DNA
                       organism = synthetic construct
SEQUENCE: 78
ggacgcgtac accccaagtc tgacataaac gcagtttaag gttt                      44

SEQ ID NO: 79          moltype = AA  length = 8
FEATURE                Location/Qualifiers
source                 1..8
                       mol_type = protein
                       organism = synthetic construct
SEQUENCE: 79
INLMFWGI                                                               8

SEQ ID NO: 80          moltype = DNA  length = 20
FEATURE                Location/Qualifiers
source                 1..20
                       mol_type = other DNA
                       organism = synthetic construct
SEQUENCE: 80
gaacacaaag catagactgc                                                 20

SEQ ID NO: 81          moltype = DNA  length = 21
FEATURE                Location/Qualifiers
source                 1..21
                       mol_type = other DNA
                       organism = synthetic construct
SEQUENCE: 81
tggggctggc cacgctcacg c                                               21

SEQ ID NO: 82          moltype = AA  length = 8
FEATURE                Location/Qualifiers
source                 1..8
                       mol_type = protein
```

```
                    organism = synthetic construct
SEQUENCE: 82
SGGSSGGS                                                             8

SEQ ID NO: 83       moltype = DNA  length = 94
FEATURE             Location/Qualifiers
source              1..94
                    mol_type = other DNA
                    organism = synthetic construct
SEQUENCE: 83
gagatgacaa agaggtatgg gcaaaaaaac ctgcgcatgt ggggttcaga ctgtatttac   60
gtcaaattcc aaatgtggat attttctctc tcgg                              94
```

ENGINEERED ADENOSINE DEAMINASES AND BASE EDITORS THEREOF

CROSS-REFERENCE TO RELATED PATENT APPLICATIONS

This application claims priority to Chinese Application No. 202310776962.5, filed Jun. 28, 2023, the contents of which are incorporated herein by reference in their entirety in the present disclosure.

SEQUENCE LISTING

The instant application contains a Sequence Listing which has been submitted in ST.26 format via Electronic Filing and is hereby incorporated by reference in its entirety. Said XML copy, created on Aug. 7, 2024, is named 44GC-374581-US-Seq list.xml and is 97,842 bytes in size.

FIELD OF THE INVENTION

The present disclosure relates to engineered adenosine deaminases, base editors based on the adenosine deaminases and complexes comprising the base editors. The present disclosure also relates to polynucleotides encoding the engineered adenosine deaminases, codon-optimized polynucleotides, vectors comprising the polynucleotides and cells comprising the vectors. The present disclosure further relates to pharmaceutical compositions comprising the base editors, the complexes, the vectors or the cells, and methods of treatment and uses involving the base editors, the complexes, the vectors, the cells or the pharmaceutical compositions.

BACKGROUND

Base editors were developed in 2016 based on CRISPR-Cas9 system and enabled precise conversion of single base without creating double-stranded DNA breaks (DSBs), thus avoiding non-homologous end joining (NHEJ) or homology directed repair (HDR) accompanied by double-stranded DNA breaks in Crispr-based gene editing technologies. Adenine base editors (ABEs), such as those based on $E.\ coli$ TadA (ecTadA), precisely convert A to G in the edited strand and T to C in the complementary strand. Currently, ABE systems find wide uses in fields of basic biology and medicine, including (1) precise editing in non-dividing cells, (2) gene function screening, (3) creation and correction of a premature termination codon, (4) identification of functionally conserved amino acids, (5) creation of splicing variants, (6) acceleration of functional loss or gain-of-function research at single base sites, and (7) clinical or theoretical research in single base mutation induced genetic diseases.

Current ABEs are formed by an RNA guided Cas protein fused with an adenosine deaminase acting on single-stranded DNA (ssDNA). The adenosine deaminase, when the fusion protein targets the genomic DNA under the guidance of the guiding RNA (such as sgRNA), binds the ssDNA and converts adenine (A) to inosine (I). The inosine is read as guanine (G) during DNA replication, and it ultimately results in A·T to G·C base pair conversion. Current ABE7.10 and miniABEmax take a long time to complete reaction and function at low efficiency. ABE8e comprising a single deaminase domain (TadA-8e) was then evolved based on ABE7.10, which enables simultaneous deamination of several adenosines. However, adenosine deaminases and ABEs as efficient as TadA-8e and ABE8e are rare, limiting their commercial uses.

SUMMARY OF INVENTION

An aspect of the invention provides an adenosine deaminase comprising an amino acid sequence having about 70% to about 99.5% sequence identity to the sequence shown in SEQ ID NO: 1 and having an amino acid substitution at one, more or all of the following sites: W23, Y36, P48, H51, L84, A106, D108, V109, K110, T111, D119, G122, H123, S146, F149, R152, H156, K157, E168, and E169, in relative to the sequence shown in SEQ ID NO: 1.

Another aspect of the invention provides an adenosine deaminase comprising an amino acid sequence shown in any of SEQ ID NOs: 2 to 10, or an amino acid sequence having at least about 80% sequence identity to each thereof.

Another aspect of the invention provides an adenosine deaminase comprising an amino acid sequence having about 70% to about 99.5% sequence identity to the sequence shown in SEQ ID NO: 12 and having an amino acid substitution at one, more or all of the following sites: E22, T47, L83, A105, D107, F108, T110, D118, R121, S145, F148, R151, E154, K156, V167, and E168, in relative to the sequence shown in SEQ ID NO: 12.

Another aspect of the invention provides an adenosine deaminase comprising an amino acid sequence shown in any of SEQ ID NOs: 13 to 16, or an amino acid sequence having at least about 80% sequence identity to each thereof.

Another aspect of the invention provides an adenosine deaminase comprising an amino acid sequence having about 70% to about 99.5% sequence identity to the sequence shown in SEQ ID NO: 17 and having an amino acid substitution at one, more or all of the following sites: W22, Q35, P47, Y50, L83, A105, D107, E108, T110, D118, G121, H122, S145, F148, R151, E154, K155, and K156, in relative to the sequence shown in SEQ ID NO: 17.

Another aspect of the invention provides an adenosine deaminase comprising an amino acid sequence shown in any of SEQ ID NOs: 18 to 21, or an amino acid sequence having at least about 80% sequence identity to each thereof.

Another aspect of the invention provides a base editor comprising any of the adenosine deaminases provided herein; and a complex formed by the base editor and a guide RNA.

Other aspects of the invention provide a polynucleotide encoding any of the adenosine deaminases or the base editors provided herein: a vector comprising the polynucleotide: a cell comprising the vector; and a pharmaceutical composition comprising the base editor, the complex, the vector or the cell.

The present disclosure also provides a method of treatment of a disease by using any of the adenosine deaminases, any of the base editors, the polynucleotide encoding any of the adenosine deaminases or the base editors provided herein; the vector comprising the polynucleotide: the cell comprising the vector; and the pharmaceutical composition comprising the base editor, the complex, the vector or the cell.

The present disclosure also provides use of any of the adenosine deaminases, any of the base editors, the polynucleotide encoding any of the adenosine deaminases or the base editors provided herein: the vector comprising the polynucleotide; the cell comprising the vector; and the pharmaceutical composition comprising the base editor, the complex, the vector or the cell in the preparation of a medicament for treatment of a disease.

The present disclosure also provides any of the adenosine deaminases, any of the base editors, the polynucleotide encoding any of the adenosine deaminases or the base editors provided herein: the vector comprising the polynucleotide; the cell comprising the vector; and the pharmaceutical composition comprising the base editor, the complex, the vector or the cell for use in treatment of a disease.

BRIEF DESCRIPTION OF THE DRAWINGS

FIG. 1A-FIG. 1D show *E. coli* growth on solid medium, showing editing effect of adenosine base editors according to some embodiments on the initial codon of ccdB gene.

FIG. 2 shows *E. coli* growth on solid medium, showing editing effect of adenosine base editors according to some embodiments on the initial codon of ccdB gene.

FIG. 3A-FIG. 3C show sequencing results showing editing effect of adenosine base editors according to some embodiments on the initial codon of ccdB gene.

FIG. 4. shows sequencing results showing editing effect of adenosine base editors according to some embodiments on the initial codon of ccdB gene.

FIG. 5A-FIG. 5C show sequencing results showing editing effect of adenosine base editors according to some embodiments on the initial codon of ccdB gene.

DETAILED DESCRIPTION OF THE INVENTION

Definition

Figure 6:
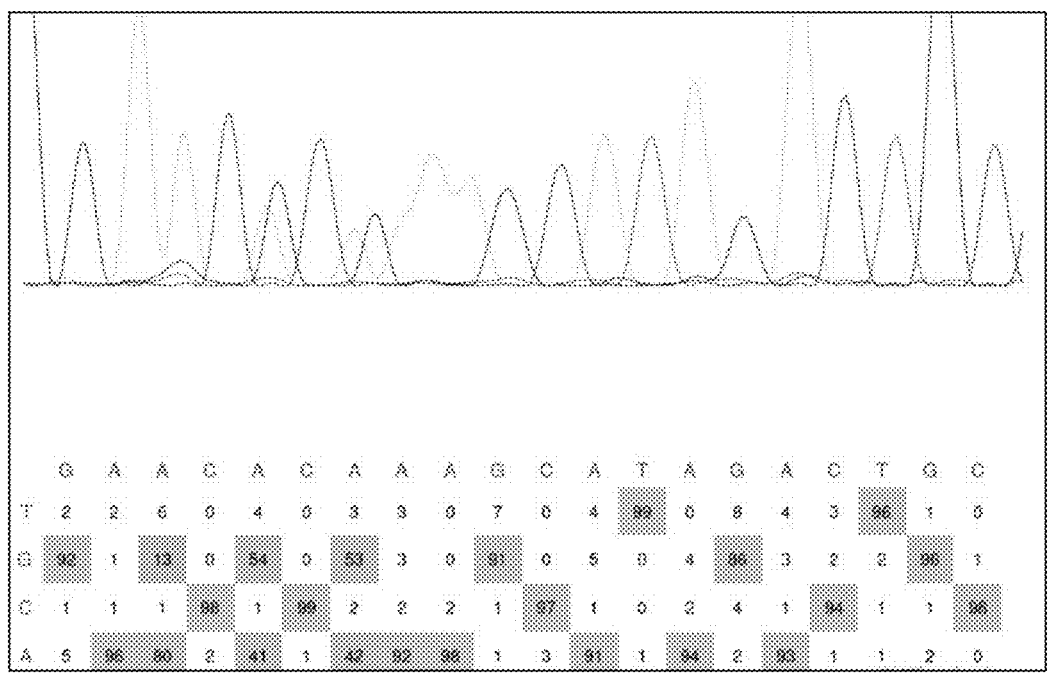
FIGS. 6-10 are sequencing results after HEK2 gene editing by various adenosine base editors in 293T cells. Sequences shown in the upper panel, are all SEQ ID NO: 80.

The term "base editor (BE)" as used herein, refers to an agent comprising a polypeptide that is capable of making a modification to a base (e.g., A, T, C, G, or U) within a nucleic acid sequence (e.g., DNA or RNA). In some embodiments, the base editor is capable of deaminating a base within a nucleic acid such as a base within a DNA molecule. In the case of an adenine base editor or an adenosine base editor, the base editor is capable of deaminating an adenine (A) in DNA. Such base editors may include a programmable DNA binding protein, such as a CRISPR-mediated Cas effector protein, fused to an adenosine deaminase. In some embodiments, the base editor comprises a nuclease-inactive Cas9 (dCas9) fused to a deaminase which binds a nucleic acid in a guide RNA-programmed manner but does not cleave the nucleic acid. For example, the dCas9 domain of the base editor may include a D10A and a H840A mutation. The DNA cleavage domain of *S. pyogenes* Cas9 includes two subdomains, the HNH nuclease subdomain and the RuvC I subdomain. The HNH subdomain cleaves the strand complementary to the gRNA (the "targeted strand", or the strand in which editing or deamination occurs), whereas the RuvC I subdomain cleaves the non-complementary strand containing the PAM sequence (the "non-edited strand"). The RuvC I mutant D10A generates a nick in the targeted strand, while the HNH mutant H840A generates a nick on the non-edited strand. In this disclosure, the term "base editor" is meant to include a base editor comprising an adenosine deaminase domain, for example, an adenine base editor (ABE) or a cytosine and adenine base editor (CABE).

The term "Cas9" or "Cas9 nuclease" or "Cas9 domain" refers to a CRISPR-associated protein 9, or variant thereof, and embraces any naturally occurring Cas9 from any organism, any naturally occurring Cas9 equivalent or fragment thereof, any Cas9 homolog, ortholog, or paralog from any organism, and any variant of a Cas9, naturally occurring or engineered. The term Cas9 is not meant to be particularly limiting and may be referred to as a "Cas9 or variant thereof." Exemplary Cas9 proteins are described herein.

As used herein, the term "dCas9" refers to a nuclease-inactive Cas9 or nuclease-dead Cas9, or a variant thereof, and embraces any naturally occurring dCas9 from any organism, any naturally occurring dCas9 equivalent or functional fragment thereof, any dCas9 homolog, ortholog, or paralog from any organism, and any variant of a dCas9, naturally occurring or engineered. The term dCas9 is not meant to be particularly limiting and may be referred to as a "dCas9 or variant thereof." Exemplary dCas9 proteins and methods for making dCas9 proteins are further described herein. Any suitable mutation which inactivates both Cas9 endonucleases, such as D10A and H840A mutations in the wild-type *S. pyogenes* Cas9 amino acid sequence, or D10A and N580A mutations in the wild-type *S. aureus* Cas9 amino acid sequence, may be used to form the dCas9.

As used herein, the term "nCas9" or "Cas9 nickase" refers to a Cas9 or a variant thereof, which cleaves or nicks only one of the strands of a target cut site thereby introducing a nick in a double strand DNA molecule rather than creating a double strand break. This can be achieved by introducing appropriate mutations in a wild-type Cas9 which inactivates one of the two endonuclease activities of the Cas9. Any suitable mutation which inactivates one Cas9 endonuclease activity but leaves the other intact is contemplated, such as one of D10A or H840A mutations in the wild-type *S. pyogenes* Cas9 amino acid sequence, or a D10A mutation in the wild-type *S. aureus* Cas9 amino acid sequence, may be used to form the nCas9.

The term "deaminase" or "deaminase domain" refers to a protein or enzyme that catalyzes a deamination reaction. In some embodiments, the deaminase is an adenosine deaminase, which catalyzes the hydrolytic deamination of the nucleobase adenine. In some embodiments, the adenosine deaminase catalyzes the hydrolytic deamination of adenine in deoxyribonucleic acid (DNA) to hypoxanthine. The deaminases provided herein may be from any organism, such as a bacterium. In some embodiments, the deaminase or deaminase domain is a variant of a naturally occurring deaminase from an organism. In some embodiments, the deaminase or deaminase domain does not occur in nature. For example, in some embodiments, the deaminase or deaminase domain is at least 50%, at least 55%, at least 60%, at least 65%, at least 70%, at least 75%, at least 80%, at least 85%, at least 90%, at least 95%, at least 96%, at least 97%, at least 98%, at least 99%, or at least 99.5% identical to a naturally occurring deaminase.

As used herein, the term "adenosine deaminase domain" refers to a domain within a base editor comprising one or more adenosine deaminase enzymes. For instance, an adenosine deaminase domain may comprise a single adenosine deaminase. In other embodiments, an adenosine deaminase domain may comprise a heterodimer of a first adenosine deaminase and a second deaminase, e.g., wherein the two deaminases are connected by a linker. Adenosine deaminases (e.g., engineered adenosine deaminases or evolved adenosine deaminases) provided herein may comprise enzymes that convert adenosine (A) to inosine (I) in DNA. Such adenosine deaminases may cause an A: T to G: C base pair conversion. In some embodiments, the deaminase is derived from a bacterium, for example, *Mangrovibacter* sp. (such as *Mangrovibacter* sp. MFB070), *Zophobihabitans entericus*, or *Erwinia* sp. (such as *Erwinia* sp. 198).

As used herein, the term "DNA binding protein" or "DNA binding protein domain" refers to any protein that localizes to and binds a specific target DNA nucleotide sequence (e.g., a gene locus of a genome). This term embraces RNA-programmable proteins, which associate (e.g., form a complex) with one or more nucleic acid molecules (i.e., which includes, for example, guide RNA in the case of Cas systems) that direct or otherwise program the protein to localize to a specific target nucleotide sequence (e.g., DNA sequence) that is complementary to the one or more nucleic acid molecules (or a portion or region thereof) associated with the protein. Exemplary RNA-programmable proteins are CRISPR-Cas9 proteins, as well as Cas9 equivalents, homologs, orthologs, or paralogs, whether naturally occurring or non-naturally occurring (e.g., engineered or modified), and may include a Cas9 equivalent from any type of CRISPR system (e.g., type II, V, VI), including Cpf1 (a type-V CRISPR-Cas systems), C2c1 (a type V CRISPR-Cas system), C2c2 (a type VI CRISPR-Cas system), C2c3 (a type V CRISPR-Cas system), dCas9, GeoCas9, CjCas9, Cas 12a, Cas 12b, Cas12c, Cas12d, Cas12f, Cas12g, Cas12h, Cas12i, Cas12m, Cas13d, Cas 14, Argonaute, and nCas9.

The term "effective amount," as used herein, refers to an amount of a biologically active agent that is sufficient to elicit a desired biological response. For example, in some embodiments, an effective amount of a composition may refer to the amount of the composition that is sufficient to edit a target site of a nucleotide sequence, e.g., a genome. In some embodiments, an effective amount of a composition provided herein, e.g., of a composition comprising a nuclease-inactive programmable DNA binding protein domain, a deaminase domain, a gRNA, may refer to the amount of the composition that is sufficient to induce editing of a target site specifically bound and edited by the base editor. In some embodiments, an effective amount of a composition provided herein may refer to the amount of the composition sufficient to induce editing having the following characteristics: >50% product purity, <5% indels, and an editing window of 2-8 nucleotides. As will be appreciated by the skilled artisan, the effective amount of an agent, e.g., a composition or a base editor-gRNA complex, may vary depending on various factors as, for example, on the desired biological response, e.g., on the specific allele, genome, or target site to be edited, on the cell or tissue being targeted, and/or on the base editor being used.

The term "fusion protein" as used herein refers to a hybrid polypeptide which comprises protein domains from at least two proteins. One protein may be located at the amino-terminal (N-terminal) portion of the fusion protein or at the carboxy-terminal (C-terminal) protein. Any of the proteins provided herein may he produced by any method known in the art. For example, the proteins provided herein may be produced via recombinant protein expression and purification, which is especially suited for fusion proteins comprising a peptide linker.

The term "linker,'" as used herein, refers to a chemical group or a molecule linking two molecules or domains, e.g., dCas9 and a deaminase. Typically, the linker is positioned between, or flanked by, two groups, molecules, or other domains and connected to each one via a covalent bond, thus connecting the two. In some embodiments, the linker is an amino acid or a plurality of amino acids (e.g., a peptide or protein). In some embodiments, the linker is an organic molecule, group, polymer, or chemical domain. Chemical groups include, but are not limited to, disulfide, hydrazone, and azide domains. In some embodiments, the linker is 5-100 amino acids in length, for example, 5, 6, 7, 8, 9, 10, 11, 12, 13, 14, 15, 16, 17, 18, 19, 20, 21, 22, 23, 24, 25, 26, 27, 28, 29, 30, 30-35, 35-40, 40-45, 45-50, 50-60, 60-70, 70-80, 80-90, 90-100, 100-150, or 150-200 amino acids in length. Longer or shorter linkers are also contemplated. In some embodiments, the linker is an XTEN linker. In some embodiments, the linker is a 32-amino acid linker consisting of glycine and serine. In other embodiments, the linker is a 30-, 31-, 33- or 34-amino acid linker consisting of glycine and serine.

The terms "non-naturally occurring" or "engineered" are used interchangeably and indicate the involvement of the hand of man. These terms, when referring to nucleic acid molecules or polypeptides (e.g., deaminases) mean that the nucleic acid molecule or the polypeptide is at least substantially free from at least one other component with which they are naturally associated in nature and/or as found in nature (e.g., an amino acid sequence not found in nature).

The term "programmable DNA binding protein" refers to any protein that may associate (e.g., form a complex) with one or more nucleic acid molecules which direct or otherwise program the protein to localize to a specific target nucleotide sequence (e.g., a gene locus of a genome) that is complementary to the one or more nucleic acid molecules (or a portion or region thereof) associated with the protein, thereby causing the protein to bind to the nucleotide sequence at the specific target site. This programmable DNA binding protein embraces CRISPR-Cas9 proteins and their functional variants.

A nuclear localization signal or sequence (NLS) is an amino acid sequence that tags, designates, or otherwise marks a protein for import into the cell nucleus by nuclear transport. Typically, this signal consists of one or more short sequences of positively charged lysines or arginines exposed on the protein surface. Different nuclear localized proteins may share the same NLS. An NLS has the opposite function of a nuclear export signal (NES), which targets proteins out of the nucleus. Thus, a single nuclear localization signal can direct the entity with which it is associated to the nucleus of a cell. Such sequences may be of any size and composition, for example more than 25, 25, 15, 12, 10, 8, 7, 6, 5, or 4 amino acids, but will preferably comprise at least a four to eight amino acid sequence known to function as a nuclear localization signal (NLS).

The term "subject," as used herein, refers to an individual organism, for example, an individual mammal. In some embodiments, the subject is a human.

As used herein, the term "variant" refers to a protein having characteristics that deviate from what occurs in nature that retains at least one functional i.e., binding, interaction, or enzymatic ability and/or therapeutic property thereof. A "variant" is at least about 70% identical, at least about 80% identical, at least about 90% identical, at least about 95% identical, at least about 96% identical, at least about 97% identical, at least about 98% identical, at least about 99% identical, at least about 99.5% identical, or at least about 99.9% identical to the wild-type protein. For instance, a variant of Cas9 may comprise a Cas9 that has one or more changes in amino acid residues as compared to a wild-type Cas9 amino acid sequence. As another example, a variant of a deaminase may comprise a deaminase that has one or more changes in amino acid residues as compared to a wild-type deaminase amino acid sequence, e.g., following ancestral sequence reconstruction of the deaminase. These changes include chemical modifications, including substitutions of different amino acid residues truncations, covalent additions (e.g., of a tag), and any other mutations. This term also embraces fragments of a wild-type protein. The level or degree of which the property is retained may be reduced or improved relative to the wild-type protein but is typically the same or similar in kind. Generally, variants are overall very similar, and in many regions, identical to the amino acid sequence of the protein described herein. The variant proteins may comprise, or alternatively consist of, an amino acid sequence which is at least 80%, 85%, 90%, 95%, 96%, 97%, 98%, 99%, or 100%, identical to, for example, the amino acid sequence of a wild-type protein, or any protein provided herein (e.g., the adenosine deaminase domain of an adenine base editor). Further, polypeptides encompassed by the invention are polypeptides encoded by polynucleotides which hybridize to the complement of a nucleic acid molecule under stringent hybridization conditions, e.g., hybridization to filter bound DNA in 6× Sodium chloride/Sodium citrate (SSC) at about 45 degrees Celsius, followed by one or more washes in 0.2×SSC, 0.1% SDS at about 50-65 degrees Celsius.

By a polypeptide having an amino acid sequence at least, for example, 95% "identical" to a query amino acid sequence, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, or substituted with another amino acid. These alterations of the reference sequence may occur at the amino- or carboxy-terminal positions of the reference amino acid sequence or anywhere between those terminal positions, interspersed either individually among residues in the reference sequence or in one or more contiguous groups within the reference sequence.

Whether any particular polypeptide is at least 80%, 85%, 90%, 95%, 96%, 97%, 98%, or 99% identical to, for instance, the amino acid sequence of a protein such as any of the deaminases provided herein, can be determined conventionally using known computer programs. A preferred method for determining the best overall match between a query sequence (a deaminase sequence of the present invention) and a subject sequence, also referred to as a global sequence alignment, can be determined using the FASTDB computer program based on the algorithm of Brutlag et at (Comp. App. Biosci. 6:237-245 (1990)). In a sequence alignment the query and subject sequences are either both nucleotide sequences or both amino acid sequences. The result of said global sequence alignment is expressed as percent identity. Preferred parameters used in a FASTDB amino acid alignment are: Matrix=PAM 0, k-tupie=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

As used herein, the term "wild type" is a term of the art understood by skilled persons and means the typical form of an organism, strain, gene, or characteristic as it occurs in nature as distinguished from mutant or variant forms.

Adenosine Deaminases

One aspect of the invention provides adenosine deaminases.

In some embodiments, provided is an adenosine deaminase, comprising an amino acid sequence having about 70% to about 99.5% sequence identity to the sequence shown in SEQ ID NO: 1 and having an amino acid substitution at one, more or all of the following sites: W23, Y36, P48, H51, L84, A106, D108, V109, K110, T111, D119, G122, H123, S146, F149, R152, H156, K157, E168, and E169, in relative to the sequence shown in SEQ ID NO: 1.

In some embodiments, provided is an adenosine deaminase comprising an amino acid sequence having about 70% to about 99.5% sequence identity to the sequence shown in SEQ ID NO: 1 and having an amino acid substitution at 1, 2, 3, 4, 5, 6, 7, 8, 9, 10, 11, 12, 13, 14, 15, 16, 17, 18, 19 or 20 of the following sites: W23, Y36, P48, H51, L84, A106, D108, V109, K110, T111, D119, G122, H123, S146, F149, R152, H156, K157, E168, and E169, in relative to the sequence shown in SEQ ID NO: 1.

In some embodiments, provided is an adenosine deaminase comprising an amino acid sequence having about 70% to about 99%, about 75% to about 99%, about 80% to about 99%, about 85% to about 99%, about 90% to about 99%, about 70% to about 95%, about 70% to about 90%, about 70% to about 89%, about 70% to about 88%, about 70% to about 87%, about 70% to about 86%, about 70% to about 85%, about 70% to about 84%, about 70% to about 83%, about 70% to about 82%, about 70% to about 81%, about 70% to about 80%, or about 70% to about 75% sequence identity to the sequence shown in SEQ ID NO: 1 and having an amino acid substitution at 1, 2, 3, 4, 5, 6, 7, 8, 9, 10, 11, 12, 13, 14, 15, 16, 17, 18, 19 or 20 of the following sites: W23, Y36, P48, H51, L84, A106, D108, V109, K110, T111, D119, G122, H123, S146, F149, R152, H156, K157, E168, and E169, in relative to the sequence shown in SEQ ID NO: 1.

In some embodiments, provided is an adenosine deaminase comprising an amino acid sequence having about 70% to about 99%, about 75% to about 99%, about 80% to about 99%, about 85% to about 99%, about 90% to about 99%, about 70% to about 95%, about 70% to about 90%, about 70% to about 89%, about 70% to about 88%, about 70% to about 87%, about 70% to about 86%, about 70% to about 85%, about 70% to about 84%, about 70% to about 83%, about 70% to about 82%, about 70% to about 81%, about 70% to about 80%, or about 70% to about 75% sequence identity to the sequence shown in SEQ ID NO: 1 and having one or more amino acid substitutions selected from the group consisting of: W23R, W23K or W23H; Y36L, Y36V, Y36I or Y36P; P48A; H51L, H51V, H51I or H51P; L84F, L84W or L84Y; A106V, A106I, A106L or A106P; D108N; V109S; K110R; T111R, T111K or T111H; D119N, D119R or D119Q; G122N; H123Y; S146C; F149Y or F149H; R152P; H156F, H156W or H156Y; K157N; E168I; and E169N.

In some embodiments, provided is an adenosine deaminase comprising an amino acid sequence having about 70% to about 90%, about 70% to about 89%, about 70% to about 88%, about 70% to about 87%, about 70% to about 86%, about 70% to about 85%, about 70% to about 84%, about 70% to about 83%, about 70% to about 82%, about 70% to about 81%, about 70% to about 80%, or about 70% to about 75% sequence identity to the sequence shown in SEQ ID NO: 1 and having all of the following amino acid substitutions: W23R, W23K or W23H; Y36L, Y36V, Y36I or Y36P; P48A; H51L, H51V, H51I or H51P; L84F, L84W or L84Y; A106V, A106I, A106L or A106P; D108N; V109S; T111R, T111K or T111H; D119N, D119R or D119Q; G122N; H123Y; S146C; F149Y or F149H; R152P; H156F, H156W or H156Y; K157N; E168I; and E169N.

In some embodiments, provided is an adenosine deaminase having an amino acid sequence of the sequence shown in SEQ ID NO: 1 and further includes one, more or all of the following substitutions: W23R; Y36L, Y36V, Y36I or Y36P; P48A; H51L, H51V, H51I or H51P; L84F, L84W or L84Y; A106V, A106I, A106L or A106P; D108N; V109S; K110R; T111R, T111K or T111H; D119N, D119R or D119Q; G122N; H123Y; S146C; F149Y or F149H; R152P; H156F, H156W or H156Y; K157N; E168I; and E169N.

In some embodiments, provided is an adenosine deaminase having an amino acid sequence of the sequence shown in SEQ ID NO: 1 and further includes one, more or all of the following substitutions: W23K; Y36L, Y36V, Y36I or Y36P; P48A; H51L, H51V, H51I or H51P; L84F, L84W or L84Y; A106V, A106I, A106L or A106P; D108N; V109S; K110R; T111R, T111K or T111H; D119N, D119R or D119Q; G122N; H123Y; S146C; F149Y or F149H; R152P; H156F, H156W or H156Y; K157N; E168I; and E169N.

In some embodiments, provided is an adenosine deaminase having an amino acid sequence of the sequence shown in SEQ ID NO: 1 and further includes one, more or all of the following substitutions: W23H; Y36L, Y36V, Y36I or Y36P; P48A; H51L, H51V, H51I or H51P; L84F, L84W or L84Y; A106V, A106I, A106L or A106P; D108N; V109S; K110R; T111R, T111K or T111H; D119N, D119R or D119Q; G122N; H123Y; S146C; F149Y or F149H; R152P; H156F, H156W or H156Y; K157N; E168I; and E169N.

In some embodiments, provided is an adenosine deaminase having an amino acid sequence of the sequence shown in SEQ ID NO: 1 and further includes one, more or all of the following substitutions: W23R, W23K or W23H; Y36L; P48A; H51L, H51V, H51I or H51P; L84F, L84W or L84Y; A106V, A106I, A106L or A106P; D108N; V109S; K110R; T111R, T111K or T111H; D119N, D119R or D119Q; G122N; H123Y; S146C; F149Y or F149H; R152P; H156F, H156W or H156Y; K157N; E168I; and E169N.

In some embodiments, provided is an adenosine deaminase having an amino acid sequence of the sequence shown in SEQ ID NO: 1 and further includes one, more or all of the following substitutions: W23R, W23K or W23H; Y36V; P48A; H51L, H51V, H51I or H51P; L84F, L84W or L84Y; A106V, A106I, A106L or A106P; D108N; V109S; K110R; T111R, T111K or T111H; D119N, D119R or D119Q; G122N; H123Y; S146C; F149Y or F149H; R152P; H156F, H156W or H156Y; K157N; E168I; and E169N.

In some embodiments, provided is an adenosine deaminase having an amino acid sequence of the sequence shown in SEQ ID NO: 1 and further includes one, more or all of the following substitutions: W23R, W23K or W23H; Y36I; P48A; H51L, H51V, H51I or H51P; L84F, L84W or L84Y; A106V, A106I, A106L or A106P; D108N; V109S; K110R; T111R, T111K or T111H; D119N, D119R or D119Q; G122N; H123Y; S146C; F149Y or F149H; R152P; H156F, H156W or H156Y; K157N; E168I; and E169N.

In some embodiments, provided is an adenosine deaminase having an amino acid sequence of the sequence shown in SEQ ID NO: 1 and further includes one, more or all of the following substitutions: W23R, W23K or W23H; Y36P; P48A; H51L, H51V, H51I or H51P; L84F, L84W or L84Y; A106V, A106I, A106L or A106P; D108N; V109S; K110R; T111R, T111K or T111H; D119N, D119R or D119Q; G122N; H123Y; S146C; F149Y or F149H; R152P; H156F, H156W or H156Y; K157N; E168I; and E169N.

In some embodiments, provided is an adenosine deaminase having an amino acid sequence of the sequence shown in SEQ ID NO: 1 and further includes one, more or all of the following substitutions: W23R, W23K or W23H; Y36L, Y36V, Y36I or Y36P; P48A; H51L; L84F, L84W or L84Y; A106V, A106I, A106L or A106P; D108N; V109S; K110R; T111R, T111K or T111H; D119N, D119R or D119Q; G122N; H123Y; S146C; F149Y or F149H; R152P; H156F, H156W or H156Y; K157N; E168I; and E169N.

In some embodiments, provided is an adenosine deaminase having an amino acid sequence of the sequence shown in SEQ ID NO: 1 and further includes one, more or all of the following substitutions: W23R, W23K or W23H; Y36L, Y36V, Y36I or Y36P; P48A; H51V; L84F, L84W or L84Y; A106V, A106I, A106L or A106P; D108N; V109S; K110R; T111R, T111K or T111H; D119N, D119R or D119Q; G122N; H123Y; S146C; F149Y or F149H; R152P; H156F, H156W or H156Y; K157N; E168I; and E169N.

In some embodiments, provided is an adenosine deaminase having an amino acid sequence of the sequence shown in SEQ ID NO: 1 and further includes one, more or all of the following substitutions: W23R, W23K or W23H; Y36L, Y36V, Y36I or Y36P; P48A; H51I; L84F, L84W or L84Y; A106V, A106I, A106L or A106P; D108N; V109S; K110R; T111R, T111K or T111H; D119N, D119R or D119Q; G122N; H123Y; S146C; F149Y or F149H; R152P; H156F, H156W or H156Y; K157N; E168I; and E169N.

In some embodiments, provided is an adenosine deaminase having an amino acid sequence of the sequence shown in SEQ ID NO: 1 and further includes one, more or all of the following substitutions: W23R, W23K or W23H; Y36L, Y36V, Y36I or Y36P; P48A; H51P; L84F, L84W or L84Y; A106V, A106I, A106L or A106P; D108N; V109S; K110R; T111R, T111K or T111H; D119N, D119R or D119Q; G122N; H123Y; S146C; F149Y or F149H; R152P; H156F, H156W or H156Y; K157N; E168I; and E169N.

In some embodiments, provided is an adenosine deaminase having an amino acid sequence of the sequence shown in SEQ ID NO: 1 and further includes one, more or all of the following substitutions: W23R, W23K or W23H; Y36L, Y36V, Y36I or Y36P; P48A; H51L, H51V, H51I or H51P; L84F; A106V, A106I, A106L or A106P; D108N; V109S;

K110R; T111R, T111K or T111H; D119N, D119R or D119Q; G122N; H123Y; S146C; F149Y or F149H; R152P; H156F, H156W or H156Y; K157N; E168I; and E169N.

In some embodiments, provided is an adenosine deaminase having an amino acid sequence of the sequence shown in SEQ ID NO: 1 and further includes one, more or all of the following substitutions: W23R, W23K or W23H; Y36L, Y36V, Y36I or Y36P; P48A; H51L, H51V, H51I or H51P; L84W; A106V, A106I, A106L or A106P; D108N; V109S; K110R; T111R, T111K or T111H; D119N, D119R or D119Q; G122N; H123Y; S146C; F149Y or F149H; R152P; H156F, H156W or H156Y; K157N; E168I; and E169N.

In some embodiments, provided is an adenosine deaminase having an amino acid sequence of the sequence shown in SEQ ID NO: 1 and further includes one, more or all of the following substitutions: W23R, W23K or W23H; Y36L, Y36V, Y36I or Y36P; P48A; H51L, H51V, H51I or H51P; L84Y; A106V, A106I, A106L or A106P; D108N; V109S; K110R; T111R, T111K or T111H; D119N, D119R or D119Q; G122N; H123Y; S146C; F149Y or F149H; R152P; H156F, H156W or H156Y; K157N; E168I; and E169N.

In some embodiments, provided is an adenosine deaminase having an amino acid sequence of the sequence shown in SEQ ID NO: 1 and further includes one, more or all of the following substitutions: W23R, W23K or W23H; Y36L, Y36V, Y36I or Y36P; P48A; H51L, H51V, H51I or H51P; L84F, L84W or L84Y; A106V; D108N; V109S; K110R; T111R, T111K or T111H; D119N, D119R or D119Q; G122N; H123Y; S146C; F149Y or F149H; R152P; H156F, H156W or H156Y; K157N; E168I; and E169N.

In some embodiments, provided is an adenosine deaminase having an amino acid sequence of the sequence shown in SEQ ID NO: 1 and further includes one, more or all of the following substitutions: W23R, W23K or W23H; Y36L, Y36V, Y36I or Y36P; P48A; H51L, H51V, H51I or H51P; L84F, L84W or L84Y; A106I; D108N; V109S; K110R; T111R, T111K or T111H; D119N, D119R or D119Q; G122N; H123Y; S146C; F149Y or F149H; R152P; H156F, H156W or H156Y; K157N; E168I; and E169N.

In some embodiments, provided is an adenosine deaminase having an amino acid sequence of the sequence shown in SEQ ID NO: 1 and further includes one, more or all of the following substitutions: W23R, W23K or W23H; Y36L, Y36V, Y36I or Y36P; P48A; H51L, H51V, H51I or H51P; L84F, L84W or L84Y; A106L; D108N; V109S; K110R; T111R, T111K or T111H; D119N, D119R or D119Q; G122N; H123Y; S146C; F149Y or F149H; R152P; H156F, H156W or H156Y; K157N; E168I; and E169N.

In some embodiments, provided is an adenosine deaminase having an amino acid sequence of the sequence shown in SEQ ID NO: 1 and further includes one, more or all of the following substitutions: W23R, W23K or W23H; Y36L, Y36V, Y36I or Y36P; P48A; H51L, H51V, H51I or H51P; L84F, L84W or L84Y; A106P; D108N; V109S; K110R; T111R, T111K or T111H; D119N, D119R or D119Q; G122N; H123Y; S146C; F149Y or F149H; R152P; H156F, H156W or H156Y; K157N; E168I; and E169N.

In some embodiments, provided is an adenosine deaminase having an amino acid sequence of the sequence shown in SEQ ID NO: 1 and further includes one, more or all of the following substitutions: W23R, W23K or W23H; Y36L, Y36V, Y36I or Y36P; P48A; H51L, H51V, H51I or H51P; L84F, L84W or L84Y; A106V, A106I, A106L or A106P; D108N; V109S; K110R; T111R, T111K or T111H; D119N, D119R or D119Q; G122N; H123Y; S146C; F149Y or F149H; R152P; H156F, H156W or H156Y; K157N; E168I; and E169N.

In some embodiments, provided is an adenosine deaminase having an amino acid sequence of the sequence shown in SEQ ID NO: 1 and further includes one, more or all of the following substitutions: W23R, W23K or W23H; Y36L, Y36V, Y36I or Y36P; P48A; H51L, H51V, H51I or H51P; L84F, L84W or L84Y; A106V, A106I, A106L or A106P; D108N; V109S; K110R; T111K; D119N, D119R or D119Q; G122N; H123Y; S146C; F149Y or F149H; R152P; H156F, H156W or H156Y; K157N; E168I; and E169N.

In some embodiments, provided is an adenosine deaminase having an amino acid sequence of the sequence shown in SEQ ID NO: 1 and further includes one, more or all of the following substitutions: W23R, W23K or W23H; Y36L, Y36V, Y36I or Y36P; P48A; H51L, H51V, H51I or H51P; L84F, L84W or L84Y; A106V, A106I, A106L or A106P; D108N; V109S; K110R; T111H; D119N, D119R or D119Q; G122N; H123Y; S146C; F149Y or F149H; R152P; H156F, H156W or H156Y; K157N; E168I; and E169N.

In some embodiments, provided is an adenosine deaminase having an amino acid sequence of the sequence shown in SEQ ID NO: 1 and further includes one, more or all of the following substitutions: W23R, W23K or W23H; Y36L, Y36V, Y36I or Y36P; P48A; H51L, H51V, H51I or H51P; L84F, L84W or L84Y; A106V, A106I, A106L or A106P; D108N; V109S; K110R; T111R, T111K or T111H; D119N; G122N; H123Y; S146C; F149Y or F149H; R152P; H156F, H156W or H156Y; K157N; E168I; and E169N.

In some embodiments, provided is an adenosine deaminase having an amino acid sequence of the sequence shown in SEQ ID NO: 1 and further includes one, more or all of the following substitutions: W23R, W23K or W23H; Y36L, Y36V, Y36I or Y36P; P48A; H51L, H51V, H51I or H51P; L84F, L84W or L84Y; A106V, A106I, A106L or A106P; D108N; V109S; K110R; T111R, T111K or T111H; D119R; G122N; H123Y; S146C; F149Y or F149H; R152P; H156F, H156W or H156Y; K157N; E168I; and E169N.

In some embodiments, provided is an adenosine deaminase having an amino acid sequence of the sequence shown in SEQ ID NO: 1 and further includes one, more or all of the following substitutions: W23R, W23K or W23H; Y36L, Y36V, Y36I or Y36P; P48A; H51L, H51V, H51I or H51P; L84F, L84W or L84Y; A106V, A106I, A106L or A106P; D108N; V109S; K110R; T111R, T111K or T111H; D119Q; G122N; H123Y; S146C; F149Y or F149H; R152P; H156F, H156W or H156Y; K157N; E168I; and E169N.

In some embodiments, provided is an adenosine deaminase having an amino acid sequence of the sequence shown in SEQ ID NO: 1 and further includes one, more or all of the following substitutions: W23R, W23K or W23H; Y36L, Y36V, Y36I or Y36P; P48A; H51L, H51V, H51I or H51P; L84F, L84W or L84Y; A106V, A106I, A106L or A106P; D108N; V109S; K110R; T111R, T111K or T111H; D119N, D119R or D119Q; G122N; H123Y; S146C; F149Y; R152P; H156F, H156W or H156Y; K157N; E168I; and E169N.

In some embodiments, provided is an adenosine deaminase having an amino acid sequence of the sequence shown in SEQ ID NO: 1 and further includes one, more or all of the following substitutions: W23R, W23K or W23H; Y36L, Y36V, Y36I or Y36P; P48A; H51L, H51V, H51I or H51P; L84F, L84W or L84Y; A106V, A106I, A106L or A106P; D108N; V109S; K110R; T111R, T111K or T111H; D119N, D119R or D119Q; G122N; H123Y; S146C; F149H; R152P; H156F, H156W or H156Y; K157N; E168I; and E169N.

In some embodiments, provided is an adenosine deaminase having an amino acid sequence of the sequence shown in SEQ ID NO: 1 and further includes one, more or all of the following substitutions: W23R, W23K or W23H; Y36L, Y36V, Y36I or Y36P; P48A; H51L, H51V, H51I or H51P; L84F, L84W or L84Y; A106V, A106I, A106L or A106P; D108N; V109S; K110R; T111R, T111K or T111H; D119N, D119R or D119Q; G122N; H123Y; S146C; F149Y or F149H; R152P; H156F; K157N; E168I; and E169N.

In some embodiments, provided is an adenosine deaminase having an amino acid sequence of the sequence shown in SEQ ID NO: 1 and further includes one, more or all of the following substitutions: W23R, W23K or W23H; Y36L, Y36V, Y36I or Y36P; P48A; H51L, H51V, H51I or H51P; L84F, L84W or L84Y; A106V, A106I, A106L or A106P; D108N; V109S; K110R; T111R, T111K or T111H; D119N, D119R or D119Q; G122N; H123Y; S146C; F149Y or F149H; R152P; H156W; K157N; E168I; and E169N.

In some embodiments, provided is an adenosine deaminase having an amino acid sequence of the sequence shown in SEQ ID NO: 1 and further includes one, more or all of the following substitutions: W23R, W23K or W23H; Y36L, Y36V, Y36I or Y36P; P48A; H51L, H51V, H51I or H51P; L84F, L84W or L84Y; A106V, A106I, A106L or A106P; D108N; V109S; K110R; T111R, T111K or T111H; D119N, D119R or D119Q; G122N; H123Y; S146C; F149Y or F149H; R152P; H156Y; K157N; E168I; and E169N.

In some embodiments, the adenosine deaminase provided herein does not contain F149Q substitution in relation to the amino acid sequence shown in SEQ ID NO: 1.

In some embodiments, provided is an adenosine deaminase comprising an amino acid sequence shown in any of SEQ ID NOs: 2 to 10, or an amino acid sequence having at least about 80%, about 85%, about 90%, about 91%, about 92%, about 93%, about 94%, about 95%, about 96%, about 97%, about 98% or about 99% sequence identity to the respective amino acid sequence shown in any of SEQ ID NOs: 2 to 10, with the proviso that the adenosine deaminase does not have the amino acid sequence shown in SEQ ID NO: 1.

In some embodiments, provided is an adenosine deaminase comprising an amino acid sequence shown in SEQ ID NO: 2 or an amino acid sequence having at least about 80%, about 85%, about 90%, about 91%, about 92%, about 93%, about 94%, about 95%, about 96%, about 97%, about 98% or about 99% sequence identity to the amino acid sequence shown in SEQ ID NO: 2, with the proviso that the adenosine deaminase does not have the amino acid sequence shown in SEQ ID NO: 1.

In some embodiments, provided is an adenosine deaminase comprising an amino acid sequence shown in SEQ ID NO: 3 or an amino acid sequence having at least about 80%, about 85%, about 90%, about 91%, about 92%, about 93%, about 94%, about 95%, about 96%, about 97%, about 98% or about 99% sequence identity to the amino acid sequence shown in SEQ ID NO: 3, with the proviso that the adenosine deaminase does not have the amino acid sequence shown in SEQ ID NO: 1.

In some embodiments, provided is an adenosine deaminase comprising an amino acid sequence shown in SEQ ID NO: 4 or an amino acid sequence having at least about 80%, about 85%, about 90%, about 91%, about 92%, about 93%, about 94%, about 95%, about 96%, about 97%, about 98% or about 99% sequence identity to the amino acid sequence shown in SEQ ID NO: 4, with the proviso that the adenosine deaminase does not have the amino acid sequence shown in SEQ ID NO: 1.

In some embodiments, provided is an adenosine deaminase comprising an amino acid sequence shown in SEQ ID NO: 5 or an amino acid sequence having at least about 80%, about 85%, about 90%, about 91%, about 92%, about 93%, about 94%, about 95%, about 96%, about 97%, about 98% or about 99% sequence identity to the amino acid sequence shown in SEQ ID NO: 5, with the proviso that the adenosine deaminase does not have the amino acid sequence shown in SEQ ID NO: 1.

In some embodiments, provided is an adenosine deaminase comprising an amino acid sequence shown in SEQ ID NO: 6 or an amino acid sequence having at least about 80%, about 85%, about 90%, about 91%, about 92%, about 93%, about 94%, about 95%, about 96%, about 97%, about 98% or about 99% sequence identity to the amino acid sequence shown in SEQ ID NO: 6, with the proviso that the adenosine deaminase does not have the amino acid sequence shown in SEQ ID NO: 1.

In some embodiments, provided is an adenosine deaminase comprising an amino acid sequence shown in SEQ ID NO: 7 or an amino acid sequence having at least about 80%, about 85%, about 90%, about 91%, about 92%, about 93%, about 94%, about 95%, about 96%, about 97%, about 98% or about 99% sequence identity to the amino acid sequence shown in SEQ ID NO: 7, with the proviso that the adenosine deaminase does not have the amino acid sequence shown in SEQ ID NO: 1.

In some embodiments, provided is an adenosine deaminase comprising an amino acid sequence shown in SEQ ID NO: 8 or an amino acid sequence having at least about 80%, about 85%, about 90%, about 91%, about 92%, about 93%, about 94%, about 95%, about 96%, about 97%, about 98% or about 99% sequence identity to the amino acid sequence shown in SEQ ID NO: 8, with the proviso that the adenosine deaminase does not have the amino acid sequence shown in SEQ ID NO: 1.

In some embodiments, provided is an adenosine deaminase comprising an amino acid sequence shown in SEQ ID NO: 9 or an amino acid sequence having at least about 80%, about 85%, about 90%, about 91%, about 92%, about 93%, about 94%, about 95%, about 96%, about 97%, about 98% or about 99% sequence identity to the amino acid sequence shown in SEQ ID NO: 9, with the proviso that the adenosine deaminase does not have the amino acid sequence shown in SEQ ID NO: 1.

In some embodiments, provided is an adenosine deaminase comprising an amino acid sequence shown in SEQ ID NO: 10 or an amino acid sequence having at least about 80%, about 85%, about 90%, about 91%, about 92%, about 93%, about 94%, about 95%, about 96%, about 97%, about 98% or about 99% sequence identity to the amino acid sequence shown in SEQ ID NO: 10, with the proviso that the adenosine deaminase does not have the amino acid sequence shown in SEQ ID NO: 1.

In some embodiments, provided is an adenosine deaminase consisting of, or substantially consisting of, an amino acid sequence shown in any of SEQ ID NOs: 2 to 10.

In some embodiments, provided is an adenosine deaminase consisting of, or substantially consisting of, an amino acid sequence shown in SEQ ID NO: 2. In some embodiments, provided is an adenosine deaminase consisting of, or substantially consisting of, an amino acid sequence shown in SEQ ID NO: 3. In some embodiments, provided is an adenosine deaminase consisting of, or substantially consisting of, an amino acid sequence shown in SEQ ID NO: 4. In some embodiments, provided is an adenosine deaminase consisting of, or substantially consisting of, an amino acid sequence shown in SEQ ID NO: 5. In some embodiments, provided is an adenosine deaminase consisting of, or substantially consisting of, an amino acid sequence shown in SEQ ID NO: 6. In some embodiments, provided is an adenosine deaminase consisting of, or substantially consisting of, an amino acid sequence shown in SEQ ID NO: 7. In some embodiments, provided is an adenosine deaminase consisting of, or substantially consisting of, an amino acid sequence shown in SEQ ID NO: 8. In some embodiments, provided is an adenosine deaminase consisting of, or substantially consisting of, an amino acid sequence shown in SEQ ID NO: 9. In some embodiments, provided is an adenosine deaminase consisting of, or substantially consisting of, an amino acid sequence shown in SEQ ID NO: 10.

In some embodiments, provided is an adenosine deaminase, comprising an amino acid sequence having about 70% to about 99.5% sequence identity to the sequence shown in SEQ ID NO: 12 and having an amino acid substitution at one, more or all of the following sites: E22, T47, L83, A105, D107, F108, T110, D118, R121, S145, F148, R151, E154, K156, V167, and E168, in relative to the sequence shown in SEQ ID NO: 12.

In some embodiments, provided is an adenosine deaminase comprising an amino acid sequence having about 70% to about 99.5% sequence identity to the sequence shown in SEQ ID NO: 12 and having an amino acid substitution at 1, 2, 3, 4, 5, 6, 7, 8, 9, 10, 11, 12, 13, 14, 15, or 16 of the following sites: E22, T47, L83, A105, D107, F108, T110, D118, R121, S145, F148, R151, E154, K156, V167, and E168, in relative to the sequence shown in SEQ ID NO: 12.

In some embodiments, provided is an adenosine deaminase comprising an amino acid sequence having about 70% to about 99%, about 75% to about 99%, about 80% to about 99%, about 85% to about 99%, about 90% to about 99%, about 70% to about 95%, about 70% to about 90%, about 70% to about 89%, about 70% to about 88%, about 70% to about 87%, about 70% to about 86%, about 70% to about 85%, about 70% to about 84%, about 70% to about 83%, about 70% to about 82%, about 70% to about 81%, about 70% to about 80%, or about 70% to about 75% sequence identity to the sequence shown in SEQ ID NO: 12 and having an amino acid substitution at 1, 2, 3, 4, 5, 6, 7, 8, 9, 10, 11, 12, 13, 14, 15, or 16 of the following sites: E22, T47, L83, A105, D107, F108, T110, D118, R121, S145, F148, R151, E154, K156, V167, and E168, in relative to the sequence shown in SEQ ID NO: 12.

In some embodiments, provided is an adenosine deaminase comprising an amino acid sequence having about 70% to about 99%, about 75% to about 99%, about 80% to about 99%, about 85% to about 99%, about 90% to about 99%, about 70% to about 95%, about 70% to about 90%, about 70% to about 89%, about 70% to about 88%, about 70% to about 87%, about 70% to about 86%, about 70% to about 85%, about 70% to about 84%, about 70% to about 83%, about 70% to about 82%, about 70% to about 81%, about 70% to about 80%, or about 70% to about 75% sequence identity to the sequence shown in SEQ ID NO: 12 and having one or more amino acid substitutions selected from the group consisting of: E22R, E22K or E22H; T47A; L83F, L83W or L83Y; A105V, A105I, A105L or A105P; D107N; F108V, F108I, F108L or F108P; T110R, T110K or T110H; D118N; R121N; S145C; F148Y; R151P; E154V, E154I, E154L or E154P; K156N; V167I; and E168N.

In some embodiments, provided is an adenosine deaminase comprising an amino acid sequence having about 70% to about 90%, about 70% to about 89%, about 70% to about 88%, about 70% to about 87%, about 70% to about 86%, about 70% to about 85%, about 70% to about 84%, about 70% to about 83%, about 70% to about 82%, about 70% to about 81%, about 70% to about 80%, or about 70% to about 75% sequence identity to the sequence shown in SEQ ID NO: 12 and having all of the following amino acid substitutions: E22R, E22K or E22H; T47A; L83F, L83W or L83Y; A105V, A105I, A105L or A105P; D107N; F108V, F108I, F108L or F108P; T110R, T110K or T110H; D118N; R121N; S145C; F148Y; R151P; E154V, E154I, E154L or E154P; K156N; V167I; and E168N.

In some embodiments, provided is an adenosine deaminase having an amino acid sequence of the sequence shown in SEQ ID NO: 12 and further includes one, more or all of the following substitutions: E22R; T47A; L83F, L83W or L83Y; A105V, A105I, A105L or A105P; D107N; F108V, F108I, F108L or F108P; T110R, T110K or T110H; D118N; R121N; S145C; F148Y; R151P; E154V, E154I, E154L or E154P; K156N; V167I; and E168N.

In some embodiments, provided is an adenosine deaminase having an amino acid sequence of the sequence shown in SEQ ID NO: 12 and further includes one, more or all of the following substitutions: E22K; T47A; L83F, L83W or L83Y; A105V, A105I, A105L or A105P; D107N; F108V, F108I, F108L or F108P; T110R, T110K or T110H; D118N; R121N; S145C; F148Y; R151P; E154V, E154I, E154L or E154P; K156N; V167I; and E168N.

In some embodiments, provided is an adenosine deaminase having an amino acid sequence of the sequence shown in SEQ ID NO: 12 and further includes one, more or all of the following substitutions: E22H; T47A; L83F, L83W or L83Y; A105V, A105I, A105L or A105P; D107N; F108V, F108I, F108L or F108P; T110R, T110K or T110H; D118N; R121N; S145C; F148Y; R151P; E154V, E154I, E154L or E154P; K156N; V167I; and E168N.

In some embodiments, provided is an adenosine deaminase having an amino acid sequence of the sequence shown in SEQ ID NO: 12 and further includes one, more or all of the following substitutions: E22R, E22K or E22H; T47A; L83F; A105V, A105I, A105L or A105P; D107N; F108V, F108I, F108L or F108P; T110R, T110K or T110H; D118N; R121N; S145C; F148Y; R151P; E154V, E154I, E154L or E154P; K156N; V167I; and E168N.

In some embodiments, provided is an adenosine deaminase having an amino acid sequence of the sequence shown in SEQ ID NO: 12 and further includes one, more or all of the following substitutions: E22R, E22K or E22H; T47A; L83W; A105V, A105I, A105L or A105P; D107N; F108V, F108I, F108L or F108P; T110R, T110K or T110H; D118N; R121N; S145C; F148Y; R151P; E154V, E154I, E154L or E154P; K156N; V167I; and E168N.

In some embodiments, provided is an adenosine deaminase having an amino acid sequence of the sequence shown in SEQ ID NO: 12 and further includes one, more or all of the following substitutions: E22R, E22K or E22H; T47A; L83Y; A105V, A105I, A105L or A105P; D107N; F108V, F108I, F108L or F108P; T110R, T110K or T110H; D118N; R121N; S145C; F148Y; R151P; E154V, E154I, E154L or E154P; K156N; V167I; and E168N.

In some embodiments, provided is an adenosine deaminase having an amino acid sequence of the sequence shown in SEQ ID NO: 12 and further includes one, more or all of the following substitutions: E22R, E22K or E22H; T47A; L83F, L83W or L83Y; A105V; D107N; F108V, F108I, F108L or F108P; T110R, T110K or T110H; D118N; R121N; S145C; F148Y; R151P; E154V, E154I, E154L or E154P; K156N; V167I; and E168N.

In some embodiments, provided is an adenosine deaminase having an amino acid sequence of the sequence shown in SEQ ID NO: 12 and further includes one, more or all of the following substitutions: E22R, E22K or E22H; T47A; L83F, L83W or L83Y; A105I; D107N; F108V, F108I, F108L or F108P; T110R, T110K or T110H; D118N; R121N; S145C; F148Y; R151P; E154V, E154I, E154L or E154P; K156N; V167I; and E168N.

In some embodiments, provided is an adenosine deaminase having an amino acid sequence of the sequence shown in SEQ ID NO: 12 and further includes one, more or all of the following substitutions: E22R, E22K or E22H; T47A; L83F, L83W or L83Y; A105L; D107N; F108V, F108I, F108L or F108P; T110R, T110K or T110H; D118N; R121N; S145C; F148Y; R151P; E154V, E154I, E154L or E154P; K156N; V167I; and E168N.

In some embodiments, provided is an adenosine deaminase having an amino acid sequence of the sequence shown in SEQ ID NO: 12 and further includes one, more or all of the following substitutions: E22R, E22K or E22H; T47A; L83F, L83W or L83Y; A105P; D107N; F108V, F108I, F108L or F108P; T110R, T110K or T110H; D118N; R121N; S145C; F148Y; R151P; E154V, E154I, E154L or E154P; K156N; V167I; and E168N.

In some embodiments, provided is an adenosine deaminase having an amino acid sequence of the sequence shown in SEQ ID NO: 12 and further includes one, more or all of the following substitutions: E22R, E22K or E22H; T47A; L83F, L83W or L83Y; A105V, A105I, A105L or A105P; D107N; F108V; T110R, T110K or T110H; D118N; R121N; S145C; F148Y; R151P; E154V, E154I, E154L or E154P; K156N; V167I; and E168N.

In some embodiments, provided is an adenosine deaminase having an amino acid sequence of the sequence shown in SEQ ID NO: 12 and further includes one, more or all of the following substitutions: E22R, E22K or E22H; T47A; L83F, L83W or L83Y; A105V, A105I, A105L or A105P; D107N; F108I; T110R, T110K or T110H; D118N; R121N; S145C; F148Y; R151P; E154V, E154I, E154L or E154P; K156N; V167I; and E168N.

In some embodiments, provided is an adenosine deaminase having an amino acid sequence of the sequence shown in SEQ ID NO: 12 and further includes one, more or all of the following substitutions: E22R, E22K or E22H; T47A; L83F, L83W or L83Y; A105V, A105I, A105L or A105P; D107N; F108L; T110R, T110K or T110H; D118N; R121N; S145C; F148Y; R151P; E154V, E154I, E154L or E154P; K156N; V167I; and E168N.

In some embodiments, provided is an adenosine deaminase having an amino acid sequence of the sequence shown in SEQ ID NO: 12 and further includes one, more or all of the following substitutions: E22R, E22K or E22H; T47A; L83F, L83W or L83Y; A105V, A105I, A105L or A105P; D107N; F108P; T110R, T110K or T110H; D118N; R121N; S145C; F148Y; R151P; E154V, E154I, E154L or E154P; K156N; V167I; and E168N.

In some embodiments, provided is an adenosine deaminase having an amino acid sequence of the sequence shown in SEQ ID NO: 12 and further includes one, more or all of the following substitutions: E22R, E22K or E22H; T47A; L83F, L83W or L83Y; A105V, A105I, A105L or A105P; D107N; F108V, F108I, F108L or F108P; T110R; D118N; R121N; S145C; F148Y; R151P; E154V, E154I, E154L or E154P; K156N; V167I; and E168N.

In some embodiments, provided is an adenosine deaminase having an amino acid sequence of the sequence shown in SEQ ID NO: 12 and further includes one, more or all of the following substitutions: E22R, E22K or E22H; T47A; L83F, L83W or L83Y; A105V, A105I, A105L or A105P; D107N; F108V, F108I, F108L or F108P; T110K; D118N; R121N; S145C; F148Y; R151P; E154V, E154I, E154L or E154P; K156N; V167I; and E168N.

In some embodiments, provided is an adenosine deaminase having an amino acid sequence of the sequence shown in SEQ ID NO: 12 and further includes one, more or all of the following substitutions: E22R, E22K or E22H; T47A; L83F, L83W or L83Y; A105V, A105I, A105L or A105P; D107N; F108V, F108I, F108L or F108P; T110H; D118N; R121N; S145C; F148Y; R151P; E154V, E154I, E154L or E154P; K156N; V167I; and E168N.

In some embodiments, provided is an adenosine deaminase having an amino acid sequence of the sequence shown in SEQ ID NO: 12 and further includes one, more or all of the following substitutions: E22R, E22K or E22H; T47A; L83F, L83W or L83Y; A105V, A105I, A105L or A105P; D107N; F108V, F108I, F108L or F108P; T110R, T110K or T110H; D118N; R121N; S145C; F148Y; R151P; E154V; K156N; V167I; and E168N.

In some embodiments, provided is an adenosine deaminase having an amino acid sequence of the sequence shown in SEQ ID NO: 12 and further includes one, more or all of the following substitutions: E22R, E22K or E22H; T47A; L83F, L83W or L83Y; A105V, A105I, A105L or A105P; D107N; F108V, F108I, F108L or F108P; T110R, T110K or T110H; D118N; R121N; S145C; F148Y; R151P; E154I; K156N; V167I; and E168N.

In some embodiments, provided is an adenosine deaminase having an amino acid sequence of the sequence shown in SEQ ID NO: 12 and further includes one, more or all of the following substitutions: E22R, E22K or E22H; T47A; L83F, L83W or L83Y; A105V, A105I, A105L or A105P; D107N; F108V, F108I, F108L or F108P; T110R, T110K or T110H; D118N; R121N; S145C; F148Y; R151P; E154L; K156N; V167I; and E168N.

In some embodiments, provided is an adenosine deaminase having an amino acid sequence of the sequence shown in SEQ ID NO: 12 and further includes one, more or all of the following substitutions: E22R, E22K or E22H; T47A; L83F, L83W or L83Y; A105V, A105I, A105L or A105P; D107N; F108V, F108I, F108L or F108P; T110R, T110K or T110H; D118N; R121N; S145C; F148Y; R151P; E154P; K156N; V167I; and E168N.

In some embodiments, provided is an adenosine deaminase comprising an amino acid sequence shown in any of SEQ ID NOs: 13 to 16, or an amino acid sequence having at least about 80%, about 85%, about 90%, about 91%, about 92%, about 93%, about 94%, about 95%, about 96%, about 97%, about 98% or about 99% sequence identity to the respective amino acid sequence shown in any of SEQ ID NOs: 13 to 16, with the proviso that the adenosine deaminase does not have the amino acid sequence shown in SEQ ID NO: 12.

In some embodiments, provided is an adenosine deaminase comprising an amino acid sequence shown in SEQ ID NO: 13, or an amino acid sequence having at least about 80%, about 85%, about 90%, about 91%, about 92%, about 93%, about 94%, about 95%, about 96%, about 97%, about 98% or about 99% sequence identity to the amino acid sequence shown in SEQ ID NO: 13, with the proviso that the adenosine deaminase does not have the amino acid sequence shown in SEQ ID NO: 12.

In some embodiments, provided is an adenosine deaminase comprising an amino acid sequence shown in SEQ ID NO: 14, or an amino acid sequence having at least about 80%, about 85%, about 90%, about 91%, about 92%, about 93%, about 94%, about 95%, about 96%, about 97%, about 98% or about 99% sequence identity to the amino acid sequence shown in SEQ ID NO: 14, with the proviso that the adenosine deaminase does not have the amino acid sequence shown in SEQ ID NO: 12.

In some embodiments, provided is an adenosine deaminase comprising an amino acid sequence shown in SEQ ID NO: 15, or an amino acid sequence having at least about 80%, about 85%, about 90%, about 91%, about 92%, about 93%, about 94%, about 95%, about 96%, about 97%, about 98% or about 99% sequence identity to the amino acid sequence shown in SEQ ID NO: 15 with the proviso that the adenosine deaminase does not have the amino acid sequence shown in SEQ ID NO: 12.

In some embodiments, provided is an adenosine deaminase comprising an amino acid sequence shown in SEQ ID NO: 16, or an amino acid sequence having at least about 80%, about 85%, about 90%, about 91%, about 92%, about 93%, about 94%, about 95%, about 96%, about 97%, about 98% or about 99% sequence identity to the amino acid sequence shown in SEQ ID NO: 16, with the proviso that the adenosine deaminase does not have the amino acid sequence shown in SEQ ID NO: 12.

In some embodiments, provided is an adenosine deaminase consisting of, or substantially consisting of, an amino acid sequence shown in any of SEQ ID NOs: 13 to 16.

In some embodiments, provided is an adenosine deaminase consisting of, or substantially consisting of, an amino acid sequence shown in SEQ ID NO: 13. In some embodiments, provided is an adenosine deaminase consisting of, or substantially consisting of, an amino acid sequence shown in SEQ ID NO: 14. In some embodiments, provided is an adenosine deaminase consisting of, or substantially consisting of, an amino acid sequence shown in SEQ ID NO: 15. In some embodiments, provided is an adenosine deaminase consisting of, or substantially consisting of, an amino acid sequence shown in SEQ ID NO: 16.

In some embodiments, provided is an adenosine deaminase, comprising an amino acid sequence having about 70% to about 99.5% sequence identity to the sequence shown in SEQ ID NO: 17 and having an amino acid substitution at one, more or all of the following sites: W22, Q35, P47, Y50, L83, A105, D107, E108, T110, D118, G121, H122, S145, F148, R151, E154, K155 and K156, in relative to the sequence shown in SEQ ID NO: 17.

In some embodiments, provided is an adenosine deaminase comprising an amino acid sequence having about 70% to about 99.5% sequence identity to the sequence shown in SEQ ID NO: 17 and having an amino acid substitution at 1, 2, 3, 4, 5, 6, 7, 8, 9, 10, 11, 12, 13, 14, 15, 16, 17 or 18 of the following sites: W22, Q35, P47, Y50, L83, A105, D107, E108, T110, D118, G121, H122, S145, F148, R151, E154, K155 and K156, in relative to the sequence shown in SEQ ID NO: 17.

In some embodiments, provided is an adenosine deaminase comprising an amino acid sequence having about 70% to about 99%, about 75% to about 99%, about 80% to about 99%, about 85% to about 99%, about 90% to about 99%, about 70% to about 95%, about 70% to about 90%, about 70% to about 89%, about 70% to about 88%, about 70% to about 87%, about 70% to about 86%, about 70% to about 85%, about 70% to about 84%, about 70% to about 83%, about 70% to about 82%, about 70% to about 81%, about 70% to about 80%, or about 70% to about 75% sequence identity to the sequence shown in SEQ ID NO: 17 and having an amino acid substitution at 1, 2, 3, 4, 5, 6, 7, 8, 9, 10, 11, 12, 13, 14, 15, 16, 17 or 18 of the following sites: W22, Q35, P47, Y50, L83, A105, D107, E108, T110, D118, G121, H122, S145, F148, R151, E154, K155 and K156, in relative to the sequence shown in SEQ ID NO: 17.

In some embodiments, provided is an adenosine deaminase comprising an amino acid sequence having about 70% to about 99%, about 75% to about 99%, about 80% to about 99%, about 85% to about 99%, about 90% to about 99%, about 70% to about 95%, about 70% to about 90%, about 70% to about 89%, about 70% to about 88%, about 70% to about 87%, about 70% to about 86%, about 70% to about 85%, about 70% to about 84%, about 70% to about 83%, about 70% to about 82%, about 70% to about 81%, about 70% to about 80%, or about 70% to about 75% sequence identity to the sequence shown in SEQ ID NO: 17 and having one or more amino acid substitutions selected from the group consisting of: W22R, W22K or W22H; Q35L, Q35V, Q35I or Q35P; P47A; Y50L, Y50V, Y50I or Y50P; L83F, L83W or L83Y; A105V, A105I, A105L or A105P; D107N; E108S; T110R, T110K or T110H; D118N; G121N; H122Y; S145C; F148Y; R151P; E154V, E154I, E154L or E154P; K155F, K155W or K155Y; and K156N.

In some embodiments, provided is an adenosine deaminase comprising an amino acid sequence having about 70% to about 99%, about 75% to about 99%, about 80% to about 99%, about 85% to about 99%, about 90% to about 99%, about 70% to about 95%, about 70% to about 90%, about 70% to about 89%, about 70% to about 88%, about 70% to about 87%, about 70% to about 86%, about 70% to about 85%, about 70% to about 84%, about 70% to about 83%, about 70% to about 82%, about 70% to about 81%, about 70% to about 80%, or about 70% to about 75% sequence identity to the sequence shown in SEQ ID NO: 17 and having all of the following amino acid substitutions: W22R, W22K or W22H; Q35L, Q35V, Q35I or Q35P; P47A; Y50L, Y50V, Y50I or Y50P; L83F, L83W or L83Y; A105V, A105I, A105L or A105P; D107N; E108S; T110R, T110K or T110H; D118N; G121N; H122Y; S145C; F148Y; R151P; E154V, E154I, E154L or E154P; K155F, K155W or K155Y; and K156N.

In some embodiments, provided is an adenosine deaminase having an amino acid sequence of the sequence shown in SEQ ID NO: 17 and further includes one, more or all of the following substitutions: W22R; Q35L, Q35V, Q35I or Q35P; P47A; Y50L, Y50V, Y50I or Y50P; L83F, L83W or L83Y; A105V, A105I, A105L or A105P; D107N; E108S; T110R, T110K or T110H; D118N; G121N; H122Y; S145C; F148Y; R151P; E154V, E154I, E154L or E154P; K155F, K155W or K155Y; and K156N.

In some embodiments, provided is an adenosine deaminase having an amino acid sequence of the sequence shown in SEQ ID NO: 17 and further includes one, more or all of the following substitutions: W22K; Q35L, Q35V, Q35I or Q35P; P47A; Y50L, Y50V, Y50I or Y50P; L83F, L83W or L83Y; A105V, A105I, A105L or A105P; D107N; E108S; T110R, T110K or T110H; D118N; G121N; H122Y; S145C; F148Y; R151P; E154V, E154I, E154L or E154P; K155F, K155W or K155Y; and K156N.

In some embodiments, provided is an adenosine deaminase having an amino acid sequence of the sequence shown in SEQ ID NO: 17 and further includes one, more or all of the following substitutions: W22H; Q35L, Q35V, Q35I or Q35P; P47A; Y50L, Y50V, Y50I or Y50P; L83F, L83W or L83Y; A105V, A105I, A105L or A105P; D107N; E108S; T110R, T110K or T110H; D118N; G121N; H122Y; S145C; F148Y; R151P; E154V, E154I, E154L or E154P; K155F, K155W or K155Y; and K156N.

In some embodiments, provided is an adenosine deaminase having an amino acid sequence of the sequence shown in SEQ ID NO: 17 and further includes one, more or all of the following substitutions: W22R, W22K or W22H; Q35L; P47A; Y50L, Y50V, Y50I or Y50P; L83F, L83W or L83Y; A105V, A105I, A105L or A105P; D107N; E108S; T110R, T110K or T110H; D118N; G121N; H122Y; S145C; F148Y; R151P; E154V, E154I, E154L or E154P; K155F, K155W or K155Y; and K156N.

In some embodiments, provided is an adenosine deaminase having an amino acid sequence of the sequence shown in SEQ ID NO: 17 and further includes one, more or all of the following substitutions: W22R, W22K or W22H; Q35V; P47A; Y50L, Y50V, Y50I or Y50P; L83F, L83W or L83Y; A105V, A105I, A105L or A105P; D107N; E108S; T110R, T110K or T110H; D118N; G121N; H122Y; S145C; F148Y; R151P; E154V, E154I, E154L or E154P; K155F, K155W or K155Y; and K156N.

In some embodiments, provided is an adenosine deaminase having an amino acid sequence of the sequence shown in SEQ ID NO: 17 and further includes one, more or all of the following substitutions: W22R, W22K or W22H; Q35I; P47A; Y50L, Y50V, Y50I or Y50P; L83F, L83W or L83Y; A105V, A105I, A105L or A105P; D107N; E108S; T110R, T110K or T110H; D118N; G121N; H122Y; S145C; F148Y; R151P; E154V, E154I, E154L or E154P; K155F, K155W or K155Y; and K156N.

In some embodiments, provided is an adenosine deaminase having an amino acid sequence of the sequence shown in SEQ ID NO: 17 and further includes one, more or all of the following substitutions: W22R, W22K or W22H; Q35P; P47A; Y50L, Y50V, Y50I or Y50P; L83F, L83W or L83Y; A105V, A105I, A105L or A105P; D107N; E108S; T110R, T110K or T110H; D118N; G121N; H122Y; S145C; F148Y; R151P; E154V, E154I, E154L or E154P; K155F, K155W or K155Y; and K156N.

In some embodiments, provided is an adenosine deaminase having an amino acid sequence of the sequence shown in SEQ ID NO: 17 and further includes one, more or all of the following substitutions: W22R, W22K or W22H; Q35L, Q35V, Q35I or Q35P; P47A; Y50L; L83F, L83W or L83Y; A105V, A105I, A105L or A105P; D107N; E108S; T110R, T110K or T110H; D118N; G121N; H122Y; S145C; F148Y; R151P; E154V, E154I, E154L or E154P; K155F, K155W or K155Y; and K156N.

In some embodiments, provided is an adenosine deaminase having an amino acid sequence of the sequence shown in SEQ ID NO: 17 and further includes one, more or all of the following substitutions: W22R, W22K or W22H; Q35L, Q35V, Q35I or Q35P; P47A; Y50V; L83F, L83W or L83Y; A105V, A105I, A105L or A105P; D107N; E108S; T110R, T110K or T110H; D118N; G121N; H122Y; S145C; F148Y; R151P; E154V, E154I, E154L or E154P; K155F, K155W or K155Y; and K156N.

In some embodiments, provided is an adenosine deaminase having an amino acid sequence of the sequence shown in SEQ ID NO: 17 and further includes one, more or all of the following substitutions: W22R, W22K or W22H; Q35L, Q35V, Q35I or Q35P; P47A; Y50I; L83F, L83W or L83Y; A105V, A105I, A105L or A105P; D107N; E108S; T110R, T110K or T110H; D118N; G121N; H122Y; S145C; F148Y; R151P; E154V, E154I, E154L or E154P; K155F, K155W or K155Y; and K156N.

In some embodiments, provided is an adenosine deaminase having an amino acid sequence of the sequence shown in SEQ ID NO: 17 and further includes one, more or all of the following substitutions: W22R, W22K or W22H; Q35L, Q35V, Q35I or Q35P; P47A; Y50P; L83F, L83W or L83Y; A105V, A105I, A105L or A105P; D107N; E108S; T110R, T110K or T110H; D118N; G121N; H122Y; S145C; F148Y; R151P; E154V, E154I, E154L or E154P; K155F, K155W or K155Y; and K156N.

In some embodiments, provided is an adenosine deaminase having an amino acid sequence of the sequence shown in SEQ ID NO: 17 and further includes one, more or all of the following substitutions: W22R, W22K or W22H; Q35L, Q35V, Q35I or Q35P; P47A; Y50L, Y50V, Y50I or Y50P; L83F; A105V, A105I, A105L or A105P; D107N; E108S; T110R, T110K or T110H; D118N; G121N; H122Y; S145C; F148Y; R151P; E154V, E154I, E154L or E154P; K155F, K155W or K155Y; and K156N.

In some embodiments, provided is an adenosine deaminase having an amino acid sequence of the sequence shown in SEQ ID NO: 17 and further includes one, more or all of the following substitutions: W22R, W22K or W22H; Q35L, Q35V, Q35I or Q35P; P47A; Y50L, Y50V, Y50I or Y50P; L83W; A105V, A105I, A105L or A105P; D107N; E108S; T110R, T110K or T110H; D118N; G121N; H122Y; S145C; F148Y; R151P; E154V, E154I, E154L or E154P; K155F, K155W or K155Y; and K156N.

In some embodiments, provided is an adenosine deaminase having an amino acid sequence of the sequence shown in SEQ ID NO: 17 and further includes one, more or all of the following substitutions: W22R, W22K or W22H; Q35L, Q35V, Q35I or Q35P; P47A; Y50L, Y50V, Y50I or Y50P; L83Y; A105V, A105I, A105L or A105P; D107N; E108S; T110R, T110K or T110H; D118N; G121N; H122Y; S145C; F148Y; R151P; E154V, E154I, E154L or E154P; K155F, K155W or K155Y; and K156N.

In some embodiments, provided is an adenosine deaminase having an amino acid sequence of the sequence shown in SEQ ID NO: 17 and further includes one, more or all of the following substitutions: W22R, W22K or W22H; Q35L, Q35V, Q35I or Q35P; P47A; Y50L, Y50V, Y50I or Y50P; L83F, L83W or L83Y; A105V; D107N; E108S; T110R, T110K or T110H; D118N; G121N; H122Y; S145C; F148Y; R151P; E154V, E154I, E154L or E154P; K155F, K155W or K155Y; and K156N.

In some embodiments, provided is an adenosine deaminase having an amino acid sequence of the sequence shown in SEQ ID NO: 17 and further includes one, more or all of the following substitutions: W22R, W22K or W22H; Q35L, Q35V, Q35I or Q35P; P47A; Y50L, Y50V, Y50I or Y50P; L83F, L83W or L83Y; A105I; D107N; E108S; T110R, T110K or T110H; D118N; G121N; H122Y; S145C; F148Y; R151P; E154V, E154I, E154L or E154P; K155F, K155W or K155Y; and K156N.

In some embodiments, provided is an adenosine deaminase having an amino acid sequence of the sequence shown in SEQ ID NO: 17 and further includes one, more or all of the following substitutions: W22R, W22K or W22H; Q35L, Q35V, Q35I or Q35P; P47A; Y50L, Y50V, Y50I or Y50P; L83F, L83W or L83Y; A105L; D107N; E108S; T110R, T110K or T110H; D118N; G121N; H122Y; S145C; F148Y; R151P; E154V, E154I, E154L or E154P; K155F, K155W or K155Y; and K156N.

In some embodiments, provided is an adenosine deaminase having an amino acid sequence of the sequence shown in SEQ ID NO: 17 and further includes one, more or all of the following substitutions: W22R, W22K or W22H; Q35L, Q35V, Q35I or Q35P; P47A; Y50L, Y50V, Y50I or Y50P; L83F, L83W or L83Y; A105P; D107N; E108S; T110R, T110K or T110H; D118N; G121N; H122Y; S145C; F148Y; R151P; E154V, E154I, E154L or E154P; K155F, K155W or K155Y; and K156N.

In some embodiments, provided is an adenosine deaminase having an amino acid sequence of the sequence shown in SEQ ID NO: 17 and further includes one, more or all of the following substitutions: W22R, W22K or W22H; Q35L, Q35V, Q35I or Q35P; P47A; Y50L, Y50V, Y50I or Y50P; L83F, L83W or L83Y; A105V, A105I, A105L or A105P; D107N; E108S; T110R; D118N; G121N; H122Y; S145C; F148Y; R151P; E154V, E154I, E154L or E154P; K155F, K155W or K155Y; and K156N.

In some embodiments, provided is an adenosine deaminase having an amino acid sequence of the sequence shown in SEQ ID NO: 17 and further includes one, more or all of the following substitutions: W22R, W22K or W22H; Q35L, Q35V, Q35I or Q35P; P47A; Y50L, Y50V, Y50I or Y50P; L83F, L83W or L83Y; A105V, A105I, A105L or A105P; D107N; E108S; T110K; D118N; G121N; H122Y; S145C; F148Y; R151P; E154V, E154I, E154L or E154P; K155F, K155W or K155Y; and K156N.

In some embodiments, provided is an adenosine deaminase having an amino acid sequence of the sequence shown in SEQ ID NO: 17 and further includes one, more or all of the following substitutions: W22R, W22K or W22H; Q35L, Q35V, Q35I or Q35P; P47A; Y50L, Y50V, Y50I or Y50P; L83F, L83W or L83Y; A105V, A105I, A105L or A105P; D107N; E108S; T110H; D118N; G121N; H122Y; S145C; F148Y; R151P; E154V, E154I, E154L or E154P; K155F, K155W or K155Y; and K156N.

In some embodiments, provided is an adenosine deaminase having an amino acid sequence of the sequence shown in SEQ ID NO: 17 and further includes one, more or all of the following substitutions: W22R, W22K or W22H; Q35L, Q35V, Q35I or Q35P; P47A; Y50L, Y50V, Y50I or Y50P; L83F, L83W or L83Y; A105V, A105I, A105L or A105P; D107N; E108S; T110R, T110K or T110H; D118N; G121N; H122Y; S145C; F148Y; R151P; E154V; K155F, K155W or K155Y; and K156N.

In some embodiments, provided is an adenosine deaminase having an amino acid sequence of the sequence shown in SEQ ID NO: 17 and further includes one, more or all of the following substitutions: W22R, W22K or W22H; Q35L, Q35V, Q35I or Q35P; P47A; Y50L, Y50V, Y50I or Y50P; L83F, L83W or L83Y; A105V, A105I, A105L or A105P; D107N; E108S; T110R, T110K or T110H; D118N; G121N; H122Y; S145C; F148Y; R151P; E154I; K155F, K155W or K155Y; and K156N.

In some embodiments, provided is an adenosine deaminase having an amino acid sequence of the sequence shown in SEQ ID NO: 17 and further includes one, more or all of the following substitutions: W22R, W22K or W22H; Q35L, Q35V, Q35I or Q35P; P47A; Y50L, Y50V, Y50I or Y50P; L83F, L83W or L83Y; A105V, A105I, A105L or A105P; D107N; E108S; T110R, T110K or T110H; D118N; G121N; H122Y; S145C; F148Y; R151P; E154L; K155F, K155W or K155Y; and K156N.

In some embodiments, provided is an adenosine deaminase having an amino acid sequence of the sequence shown in SEQ ID NO: 17 and further includes one, more or all of the following substitutions: W22R, W22K or W22H; Q35L, Q35V, Q35I or Q35P; P47A; Y50L, Y50V, Y50I or Y50P; L83F, L83W or L83Y; A105V, A105I, A105L or A105P; D107N; E108S; T110R, T110K or T110H; D118N; G121N; H122Y; S145C; F148Y; R151P; E154P; K155F, K155W or K155Y; and K156N.

In some embodiments, provided is an adenosine deaminase having an amino acid sequence of the sequence shown in SEQ ID NO: 17 and further includes one, more or all of the following substitutions: W22R, W22K or W22H; Q35L, Q35V, Q35I or Q35P; P47A; Y50L, Y50V, Y50I or Y50P; L83F, L83W or L83Y; A105V, A105I, A105L or A105P; D107N; E108S; T110R, T110K or T110H; D118N; G121N; H122Y; S145C; F148Y; R151P; E154V, E154I, E154L or E154P; K155F; and K156N.

In some embodiments, provided is an adenosine deaminase having an amino acid sequence of the sequence shown in SEQ ID NO: 17 and further includes one, more or all of the following substitutions: W22R, W22K or W22H; Q35L, Q35V, Q35I or Q35P; P47A; Y50L, Y50V, Y50I or Y50P; L83F, L83W or L83Y; A105V, A105I, A105L or A105P; D107N; E108S; T110R, T110K or T110H; D118N; G121N; H122Y; S145C; F148Y; R151P; E154V, E154I, E154L or E154P; K155W; and K156N.

In some embodiments, provided is an adenosine deaminase having an amino acid sequence of the sequence shown in SEQ ID NO: 17 and further includes one, more or all of the following substitutions: W22R, W22K or W22H; Q35L, Q35V, Q35I or Q35P; P47A; Y50L, Y50V, Y50I or Y50P; L83F, L83W or L83Y; A105V, A105I, A105L or A105P; D107N; E108S; T110R, T110K or T110H; D118N; G121N; H122Y; S145C; F148Y; R151P; E154V, E154I, E154L or E154P; K155Y; and K156N.

In some embodiments, provided is an adenosine deaminase comprising an amino acid sequence shown in any of SEQ ID NOs: 18 to 21, or an amino acid sequence having at least about 80%, about 85%, about 90%, about 91%, about 92%, about 93%, about 94%, about 95%, about 96%, about 97%, about 98% or about 99% sequence identity to the respective amino acid sequence shown in any of SEQ ID NOs: 18 to 21, with the proviso that the adenosine deaminase does not have the amino acid sequence shown in SEQ ID NO: 17.

In some embodiments, provided is an adenosine deaminase comprising an amino acid sequence shown in SEQ ID NO: 18, or an amino acid sequence having at least about 80%, about 85%, about 90%, about 91%, about 92%, about 93%, about 94%, about 95%, about 96%, about 97%, about 98% or about 99% sequence identity to the amino acid sequence shown in SEQ ID NO: 18, with the proviso that the adenosine deaminase does not have the amino acid sequence shown in SEQ ID NO: 17.

In some embodiments, provided is an adenosine deaminase comprising an amino acid sequence shown in SEQ ID NO: 19, or an amino acid sequence having at least about 80%, about 85%, about 90%, about 91%, about 92%, about 93%, about 94%, about 95%, about 96%, about 97%, about 98% or about 99% sequence identity to the amino acid sequence shown in SEQ ID NO: 19, with the proviso that the adenosine deaminase does not have the amino acid sequence shown in SEQ ID NO: 17.

In some embodiments, provided is an adenosine deaminase comprising an amino acid sequence shown in SEQ ID NO: 20, or an amino acid sequence having at least about 80%, about 85%, about 90%, about 91%, about 92%, about 93%, about 94%, about 95%, about 96%, about 97%, about 98% or about 99% sequence identity to the amino acid sequence shown in SEQ ID NO: 20, with the proviso that the adenosine deaminase does not have the amino acid sequence shown in SEQ ID NO: 17.

In some embodiments, provided is an adenosine deaminase comprising an amino acid sequence shown in SEQ ID NO: 21, or an amino acid sequence having at least about 80%, about 85%, about 90%, about 91%, about 92%, about 93%, about 94%, about 95%, about 96%, about 97%, about 98% or about 99% sequence identity to the amino acid sequence shown in SEQ ID NO: 21, with the proviso that the adenosine deaminase does not have the amino acid sequence shown in SEQ ID NO: 17.

In some embodiments, provided is an adenosine deaminase consisting of, or substantially consisting of, an amino acid sequence shown in any of SEQ ID NOs: 18 to 21.

In some embodiments, provided is an adenosine deaminase consisting of, or substantially consisting of, an amino acid sequence shown in SEQ ID NO: 18. In some embodiments, provided is an adenosine deaminase consisting of, or substantially consisting of, an amino acid sequence shown in SEQ ID NO: 19. In some embodiments, provided is an adenosine deaminase consisting of, or substantially consisting of, an amino acid sequence shown in SEQ ID NO: 20. In some embodiments, provided is an adenosine deaminase consisting of, or substantially consisting of, an amino acid sequence shown in SEQ ID NO: 21.

As will be appreciated by a skilled person in the art, any of the deaminases provided herein could exist independently or as a deaminase domain when it covalently binds to other part, forming a molecule comprising the deaminase domain, such as a base editor. The term "adenosine deaminase" as used herein is meant to include the form of an adenosine deaminase domain. An adenosine deaminase domain could be covalently coupled to other part at its N- or C-terminus or any position therebetween. For example, an adenosine deaminase may be covalently coupled to the C terminus of a nuclear localization sequence at N terminus, e.g., through a peptide linkage formed by the —NH$_2$ of the amino acid residue at the most N terminus of the adenosine deaminase and the —COOH of the amino acid residue at the most C terminus of the nuclear localization sequence, while the C terminus of the adenosine deaminase keeps free, i.e., containing free-COOH. For another example, an adenosine deaminase may be covalently coupled to the N terminus of a nuclear localization sequence at C terminus, e.g., through a peptide linkage formed by —NH$_2$ and —COOH group, while the N terminus of the adenosine deaminase keeps free, i.e., containing free —NH$_2$. For yet another example, an adenosine deaminase may be covalently coupled to the C terminus of a nuclear localization sequence at N terminus and to the N terminus of an DNA binding protein at C terminus. Therefore, any of the adenosine deaminases provided herein could be included in a greater protein molecule as an adenosine deaminase domain while retaining the adenosine deaminase activity and acts together with other parts of the greater protein molecule to function, such as, as a base editor, which will be discussed in greater detail in the following.

Base Editors

Another aspect of the disclosure provides a base editor.

In some embodiments, provided is a base editor comprising any of the adenosine deaminase provided herein. In some embodiments, the base editor is an adenine base editor. In some embodiments, the base editor is an adenine and cytidine base editor comprising an adenosine deaminase and a cytidine deaminase to effect simultaneous editing of an adenosine and a cytosine. The base editor of the present invention functions in a form of a fusion protein in a cell.

Thus, in some embodiments, provided is a base editor comprising an adenosine deaminase domain formed by any of the adenosine deaminase provided by the present invention.

In some embodiments, provided is a base editor comprising an adenosine deaminase domain comprising an amino acid sequence shown in any of SEQ ID NOS: 2 to 10, 13 to 16, and 18 to 21, or an amino acid sequence having at least about 80% sequence identity to the amino acid sequence shown in in any of SEQ ID NOs: 2 to 10, 13 to 16, and 18 to 21, with the proviso that the adenosine deaminase domain does not have the amino acid sequence shown in SEQ ID NO: 1, 12 or 17.

In some embodiments, provided is a base editor comprising an adenosine deaminase domain comprising an amino acid sequence shown in any of SEQ ID NOs: 2 to 10, 13 to 16, and 18 to 21, or an amino acid sequence having at least about 80%, about 85%, about 90%, about 91%, about 92%, about 93%, about 94%, about 95%, about 96%, about 97%, about 98% or about 99% sequence identity to the amino acid sequence shown in any of SEQ ID NOs: 2 to 10, 13 to 16, and 18 to 21, with the proviso that the adenosine deaminase domain does not have the amino acid sequence shown in SEQ ID NO: 1, 12 or 17.

In some embodiments, provided is a base editor comprising an adenosine deaminase domain comprising an amino acid sequence shown SEQ ID NO: 2, or an amino acid sequence having at least about 80%, about 85%, about 90%, about 91%, about 92%, about 93%, about 94%, about 95%, about 96%, about 97%, about 98% or about 99% sequence identity to the amino acid sequence shown in SEQ ID NO: 2, with the proviso that the adenosine deaminase domain does not have the amino acid sequence shown in SEQ ID NO: 1.

In some embodiments, provided is a base editor comprising an adenosine deaminase domain comprising an amino acid sequence shown SEQ ID NO: 3, or an amino acid sequence having at least about 80%, about 85%, about 90%, about 91%, about 92%, about 93%, about 94%, about 95%, about 96%, about 97%, about 98% or about 99% sequence identity to the amino acid sequence shown in SEQ ID NO: 3, with the proviso that the adenosine deaminase domain does not have the amino acid sequence shown in SEQ ID NO: 1.

In some embodiments, provided is a base editor comprising an adenosine deaminase domain comprising an amino acid sequence shown SEQ ID NO: 4, or an amino acid sequence having at least about 80%, about 85%, about 90%, about 91%, about 92%, about 93%, about 94%, about 95%, about 96%, about 97%, about 98% or about 99% sequence identity to the amino acid sequence shown in SEQ ID NO: 4, with the proviso that the adenosine deaminase domain does not have the amino acid sequence shown in SEQ ID NO: 1.

In some embodiments, provided is a base editor comprising an adenosine deaminase domain comprising an amino acid sequence shown SEQ ID NO: 5, or an amino acid sequence having at least about 80%, about 85%, about 90%, about 91%, about 92%, about 93%, about 94%, about 95%, about 96%, about 97%, about 98% or about 99% sequence identity to the amino acid sequence shown in SEQ ID NO: 5, with the proviso that the adenosine deaminase domain does not have the amino acid sequence shown in SEQ ID NO: 1.

In some embodiments, provided is a base editor comprising an adenosine deaminase domain comprising an amino acid sequence shown SEQ ID NO: 6, or an amino acid sequence having at least about 80%, about 85%, about 90%, about 91%, about 92%, about 93%, about 94%, about 95%, about 96%, about 97%, about 98% or about 99% sequence identity to the amino acid sequence shown in SEQ ID NO: 6, with the proviso that the adenosine deaminase domain does not have the amino acid sequence shown in SEQ ID NO: 1.

In some embodiments, provided is a base editor comprising an adenosine deaminase domain comprising an amino acid sequence shown SEQ ID NO: 7, or an amino acid sequence having at least about 80%, about 85%, about 90%, about 91%, about 92%, about 93%, about 94%, about 95%, about 96%, about 97%, about 98% or about 99% sequence identity to the amino acid sequence shown in SEQ ID NO: 7, with the proviso that the adenosine deaminase domain does not have the amino acid sequence shown in SEQ ID NO: 1.

In some embodiments, provided is a base editor comprising an adenosine deaminase domain comprising an amino acid sequence shown SEQ ID NO: 8, or an amino acid sequence having at least about 80%, about 85%, about 90%, about 91%, about 92%, about 93%, about 94%, about 95%, about 96%, about 97%, about 98% or about 99% sequence identity to the amino acid sequence shown in SEQ ID NO: 8, with the proviso that the adenosine deaminase domain does not have the amino acid sequence shown in SEQ ID NO: 1.

In some embodiments, provided is a base editor comprising an adenosine deaminase domain comprising an amino acid sequence shown SEQ ID NO: 9, or an amino acid sequence having at least about 80%, about 85%, about 90%, about 91%, about 92%, about 93%, about 94%, about 95%, about 96%, about 97%, about 98% or about 99% sequence identity to the amino acid sequence shown in SEQ ID NO: 9, with the proviso that the adenosine deaminase domain does not have the amino acid sequence shown in SEQ ID NO: 1.

In some embodiments, provided is a base editor comprising an adenosine deaminase domain comprising an amino acid sequence shown SEQ ID NO: 10, or an amino acid sequence having at least about 80%, about 85%, about 90%, about 91%, about 92%, about 93%, about 94%, about 95%, about 96%, about 97%, about 98% or about 99% sequence identity to the amino acid sequence shown in SEQ ID NO: 10, with the proviso that the adenosine deaminase domain does not have the amino acid sequence shown in SEQ ID NO: 1.

In some embodiments, provided is a base editor comprising an adenosine deaminase domain comprising an amino acid sequence shown SEQ ID NO: 13, or an amino acid sequence having at least about 80%, about 85%, about 90%, about 91%, about 92%, about 93%, about 94%, about 95%, about 96%, about 97%, about 98% or about 99% sequence identity to the amino acid sequence shown in SEQ ID NO: 13, with the proviso that the adenosine deaminase domain does not have the amino acid sequence shown in SEQ ID NO: 12.

In some embodiments, provided is a base editor comprising an adenosine deaminase domain comprising an amino acid sequence shown SEQ ID NO: 14, or an amino acid sequence having at least about 80%, about 85%, about 90%, about 91%, about 92%, about 93%, about 94%, about 95%, about 96%, about 97%, about 98% or about 99% sequence identity to the amino acid sequence shown in SEQ ID NO: 14, with the proviso that the adenosine deaminase domain does not have the amino acid sequence shown in SEQ ID NO: 12.

In some embodiments, provided is a base editor comprising an adenosine deaminase domain comprising an amino acid sequence shown SEQ ID NO: 15, or an amino acid sequence having at least about 80%, about 85%, about 90%, about 91%, about 92%, about 93%, about 94%, about 95%, about 96%, about 97%, about 98% or about 99% sequence identity to the amino acid sequence shown in SEQ ID NO: 15, with the proviso that the adenosine deaminase domain does not have the amino acid sequence shown in SEQ ID NO: 12.

In some embodiments, provided is a base editor comprising an adenosine deaminase domain comprising an amino acid sequence shown SEQ ID NO: 16, or an amino acid sequence having at least about 80%, about 85%, about 90%, about 91%, about 92%, about 93%, about 94%, about 95%, about 96%, about 97%, about 98% or about 99% sequence identity to the amino acid sequence shown in SEQ ID NO: 16, with the proviso that the adenosine deaminase domain does not have the amino acid sequence shown in SEQ ID NO: 12.

In some embodiments, provided is a base editor comprising an adenosine deaminase domain comprising an amino acid sequence shown SEQ ID NO: 18, or an amino acid sequence having at least about 80%, about 85%, about 90%, about 91%, about 92%, about 93%, about 94%, about 95%, about 96%, about 97%, about 98% or about 99% sequence identity to the amino acid sequence shown in SEQ ID NO: 18, with the proviso that the adenosine deaminase domain does not have the amino acid sequence shown in SEQ ID NO: 17.

In some embodiments, provided is a base editor comprising an adenosine deaminase domain comprising an amino acid sequence shown SEQ ID NO: 19, or an amino acid sequence having at least about 80%, about 85%, about 90%, about 91%, about 92%, about 93%, about 94%, about 95%, about 96%, about 97%, about 98% or about 99% sequence identity to the amino acid sequence shown in SEQ ID NO: 19, with the proviso that the adenosine deaminase domain does not have the amino acid sequence shown in SEQ ID NO: 17.

In some embodiments, provided is a base editor comprising an adenosine deaminase domain comprising an amino acid sequence shown SEQ ID NO: 20, or an amino acid sequence having at least about 80%, about 85%, about 90%, about 91%, about 92%, about 93%, about 94%, about 95%, about 96%, about 97%, about 98% or about 99% sequence identity to the amino acid sequence shown in SEQ ID NO: 20, with the proviso that the adenosine deaminase domain does not have the amino acid sequence shown in SEQ ID NO: 17.

In some embodiments, provided is a base editor comprising an adenosine deaminase domain comprising an amino acid sequence shown SEQ ID NO: 21, or an amino acid sequence having at least about 80%, about 85%, about 90%, about 91%, about 92%, about 93%, about 94%, about 95%, about 96%, about 97%, about 98% or about 99% sequence identity to the amino acid sequence shown in SEQ ID NO: 21, with the proviso that the adenosine deaminase domain does not have the amino acid sequence shown in SEQ ID NO: 17.

In some embodiments, provided is a base editor comprising an adenosine deaminase domain, wherein the adenosine deaminase domain is a heterodimer comprising a first deaminase domain and a second deaminase domain, wherein the first deaminase domain comprises an amino acid sequence shown in any of SEQ ID NOs: 2 to 10, 13 to 16, and 18 to 21, or an amino acid sequence having at least about 80%, about 85%, about 90%, about 91%, about 92%, about 93%, about 94%, about 95%, about 96%, about 97%, about 98% or about 99% sequence identity to the amino acid sequence shown in any of SEQ ID NOs: 2 to 10, 13 to 16, and 18 to 21, with the proviso that the first adenosine deaminase domain does not have the amino acid sequence shown in any of SEQ ID NO: 1, 12 or 17, and wherein the second deaminase domain comprises an amino acid sequence shown in any of SEQ ID NOs: 1, 12 and 17, or an amino acid sequence having at least about 80%, about 85%, about 90%, about 91%, about 92%, about 93%, about 94%, about 95%, about 96%, about 97%, about 98% or about 99% sequence identity to the amino acid sequence shown in any of SEQ ID NOS: 1, 12 and 17.

In some embodiments, provided is a base editor comprising an adenosine deaminase domain, wherein the adenosine deaminase domain is a heterodimer comprising a first deaminase domain and a second deaminase domain, wherein the first deaminase domain comprises an amino acid sequence shown in any of SEQ ID NOs: 2 to 10, or an amino acid sequence having at least about 80%, about 85%, about 90%, about 91%, about 92%, about 93%, about 94%, about 95%, about 96%, about 97%, about 98% or about 99% sequence identity to the amino acid sequence shown in any of SEQ ID NOs: 2 to 10, with the proviso that the first adenosine deaminase domain does not have the amino acid sequence shown in SEQ ID NO: 1, and wherein the second deaminase domain comprises an amino acid sequence shown in SEQ ID NO: 1, or an amino acid sequence having at least about 80%, about 85%, about 90%, about 91%, about 92%, about 93%, about 94%, about 95%, about 96%, about 97%, about 98% or about 99% sequence identity to the amino acid sequence shown in SEQ ID NO: 1.

In some embodiments, provided is a base editor comprising an adenosine deaminase domain, wherein the adenosine deaminase domain is a heterodimer comprising a first deaminase domain and a second deaminase domain, wherein the first deaminase domain comprises an amino acid sequence shown in any of SEQ ID NOs: 13 to 16, or an amino acid sequence having at least about 80%, about 85%, about 90%, about 91%, about 92%, about 93%, about 94%, about 95%, about 96%, about 97%, about 98% or about 99% sequence identity to the amino acid sequence shown in any of SEQ ID NOs: 13 to 16, with the proviso that the first adenosine deaminase domain does not have the amino acid sequence shown in SEQ ID NO: 12, and wherein the second deaminase domain comprises an amino acid sequence shown in SEQ ID NO: 12, or an amino acid sequence having at least about 80%, about 85%, about 90%, about 91%, about 92%, about 93%, about 94%, about 95%, about 96%, about 97%, about 98% or about 99% sequence identity to the amino acid sequence shown in SEQ ID NO: 12.

In some embodiments, provided is a base editor comprising an adenosine deaminase domain, wherein the adenosine deaminase domain is a heterodimer comprising a first deaminase domain and a second deaminase domain, wherein the first deaminase domain comprises an amino acid sequence shown in any of SEQ ID NOs: 18 to 21, or an amino acid sequence having at least about 80%, about 85%, about 90%, about 91%, about 92%, about 93%, about 94%, about 95%, about 96%, about 97%, about 98% or about 99% sequence identity to the amino acid sequence shown in any of SEQ ID NOs: 18 to 21, with the proviso that the first adenosine deaminase domain does not have the amino acid sequence shown in SEQ ID NO: 17, and wherein the second deaminase domain comprises an amino acid sequence shown in SEQ ID NO: 17, or an amino acid sequence having at least about 80%, about 85%, about 90%, about 91%, about 92%, about 93%, about 94%, about 95%, about 96%, about 97%, about 98% or about 99% sequence identity to the amino acid sequence shown in SEQ ID NO: 17.

In any of the base editor embodiments, the base editor may comprise a programmable DNA binding domain. In such embodiments, the programmable DNA binding domain may be a CRISPR associated nuclease. Illustrative CRISPR associated nucleases include Cas9 nucleases and variants thereof. In various embodiments, the programmable DNA binding domain has a nickase activity (e.g., nCas9), i.e., only cleave one strand of the target DNA sequence. In other embodiments, the programmable DNA binding domain has an inactive nuclease, e.g., are "dead" proteins (e.g., dCas9). The base editors provided herein may also comprise Cas9 equivalents, including Cas12a, Cas12b, Cas12f, Cas12i and Cas12m proteins. The programmable DNA binding domain (e.g., SpCas9, SaCas9, SaCas9 variants or SpCas9 variants) may also contain various modifications that alter/enhance their PAM specificities. The disclosure contemplates any Cas9, Cas9 variant, or Cas9 equivalent which has at least 70%, at least 75%, at least 80%, at least 85%, at least 90%, at least 91%, at least 92%, at least 93%, at least 94%, at least 95%, at least 96%, at least 97%, at least 98%, at least 99%, or at least 99.9% sequence identity to a reference Cas9 sequence, such as a reference dCas9 or nCas9 sequence set forth in SEQ ID NO: 22 or 23.

In some embodiments, the programmable DNA binding domain may comprise more than one programmable DNA binding protein. Accordingly, in some embodiments, any of the disclosed base editors may contain a first programmable DNA binding domain and a second programmable DNA binding domain. In some embodiments, the programmable DNA binding domain (or the first and second programmable DNA binding domain, respectively) comprises a first Cas homolog or variant and a second Cas homolog or variant (e.g., a first Cas variant comprising a Cas9-NG and a second Cas variant comprising a Cas9-CP1041, e.g., "SpCas9-NG-CP1041"). In some embodiments, the first Cas variant comprises a Cas9-NG, and the second Cas variant comprises a SpCas9-VRQR.

In some embodiments, the base editors provided herein further comprise one or more nuclear localization sequence (NLS). In certain embodiments, any of the base editors comprise a single NLS. In certain embodiments, any of the base editors comprise two NLSs. In some embodiments, one or more of the NLSs are monopartite NLS or bipartite NLSs. In certain embodiments, the disclosed base editors comprise two bipartite NLSs.

In some embodiments, the nuclear localization sequence comprises a nucleotide sequence or an amino acid sequence shown in any of SEQ ID NOs: 32 to 36. In some embodiment, the nuclear localization sequence comprises a nucleotide sequence shown in SEQ ID NO: 32. In some embodiment, the nuclear localization sequence comprises an amino acid sequence shown in SEQ ID NO: 33. In some embodiment, the nuclear localization sequence comprises an amino acid sequence shown in SEQ ID NO: 34. In some embodiment, the nuclear localization sequence comprises an amino acid sequence shown in SEQ ID NO: 35. In some embodiment, the nuclear localization sequence comprises an amino acid sequence shown in SEQ ID NO: 36.

In some embodiments, the base editors provided herein further comprise a cytidine deaminase to form a base editor capable of editing cytidine and adenosine simultaneously (CABE). Exemplary cytidine deaminases include AID, APOBEC3A, APOEC1, PmCDA1, LjCDA1 or orthologs thereof.

In certain embodiments, linkers may be used to link any of the peptides or peptide domains or domains of the base editor (e.g., a programmable DNA binding domain covalently linked to an adenosine deaminase domain which is covalently linked to an NLS domain). The base editors described herein may comprise linkers of 32 amino acids in length. In some embodiments, the linker connects Cas9 and a deaminase. In some embodiments, the linker connects dCas9 and a deaminase. In some embodiments, the linker is positioned between, or flanked by, two groups, molecules, or other domains and connected to each one via a covalent bond or non-covalent interaction, thus connecting the two. In some embodiments, the linker is a polynucleotide. In some embodiments, the linker is a DNA linking sequence. Exemplary linkers comprise an amino acid or nucleotide sequence shown in any of SEQ ID NOs: 11, 26, 27, 37 to 41. In some embodiments, the base editors can comprise a plurality of linkers, with each linker being same or different from each other.

The present disclosure further provides guide RNAs for use in accordance with the disclosed methods of editing. The disclosure provides guide RNAs that are designed to recognize target sequences. Such gRNAs may be designed to have guide sequences (or "spacers") having complementarity to a protospacer within the target sequence. Guide RNAs are also provided for use with one or more of the disclosed adenine base editors, e.g., in the disclosed methods of editing a nucleic acid molecule. Such gRNAs may be designed to have guide sequences having complementarity to a protospacer within a target sequence to be edited, and to have backbone sequences that interact specifically with the programmable DNA binding domains of any of the disclosed base editors, such as Cas9 nickase domains of the disclosed base editors.

In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, each gRNA comprises a guide sequence of at least 10 contiguous nucleotides (e.g., 10, 11, 12, 13, 14, 15, 16, 17, 18, 19, 20, 21, 22, 23, 24, 25, 26, 27, 28, 29, or 30 contiguous nucleotides) that is complementary to a target sequence. The DNA sequence encoding the guide RNA can be linear or circular. In some embodiments, nuclease Cas9 or Cas9 domain is used with one or more gRNA.

In some embodiments, exemplary base editors comprise an architecture of: $NH_2$-[adenosine deaminase domain]-[programmable DNA binding domain]-COOH; or $NH_2$-[programmable DNA binding domain]-[adenosine deaminase domain]-COOH, in which ]-[ represents an optional linker as defined in the above (same hereinafter).

In some embodiments, a base editor comprising a first and second adenosine deaminase comprises an architecture selected from the group consisting of:
 $NH_2$-[first adenosine deaminase domain]-[second adenosine deaminase domain]-[programmable DNA binding domain]-COOH;
 $NH_2$-[first adenosine deaminase domain]-[programmable DNA binding domain]-[second adenosine deaminase domain]-COOH;
 $NH_2$-[programmable DNA binding domain]-[first adenosine deaminase domain]-[second adenosine deaminase domain]-COOH;
 $NH_2$-[second adenosine deaminase domain]-[first adenosine deaminase domain]-[programmable DNA binding domain]-COOH;
 $NH_2$-[second adenosine deaminase domain]-[programmable DNA binding domain]-[first adenosine deaminase domain]-COOH; and
 $NH_2$-[programmable DNA binding domain]-[second adenosine deaminase domain]-[first adenosine deaminase domain]-COOH.

In some embodiments, a base editor comprising an NLS comprises an architecture selected from the group consisting of:
 $NH_2$-[adenosine deaminase domain]-[programmable DNA binding domain]-[NLS]-COOH;
 $NH_2$-[programmable DNA binding domain]-[adenosine deaminase domain]-[NLS]-COOH;
 $NH_2$-[NLS]-[adenosine deaminase domain]-[programmable DNA binding domain]-COOH;
 $NH_2$-[NLS]-[programmable DNA binding domain]-[adenosine deaminase domain]-COOH;
 $NH_2$-[NLS]-[adenosine deaminase domain]-[programmable DNA binding domain]-[NLS]-COOH; and
 $NH_2$-[NLS]-[programmable DNA binding domain]-[adenosine deaminase domain]-[NLS]-COOH.

In certain embodiments, the base editors provided herein comprises an architecture selected from the group consisting of:
 $NH_2$-[NLS]-[MaTadA1.0]-[programmable DNA binding domain]-[NLS]-COOH;
 $NH_2$-[NLS]-[programmable DNA binding domain]-[MaTadA1.0]-[NLS]-COOH;
 $NH_2$-[NLS]-[MaTadA1.0-1]-[programmable DNA binding domain]-[NLS]-COOH;
 $NH_2$-[NLS]-[programmable DNA binding domain]-[MaTadA1.0-1]-[NLS]-COOH;
 $NH_2$-[NLS]-[MaTadA1.0-2]-[programmable DNA binding domain]-[NLS]-COOH;
 $NH_2$-[NLS]-[programmable DNA binding domain]-[MaTadA1.0-2]-[NLS]-COOH;
 $NH_2$-[NLS]-[MaTadA1.0-3]-[programmable DNA binding domain]-[NLS]-COOH;
 $NH_2$-[NLS]-[programmable DNA binding domain]-[MaTadA1.0-3]-[NLS]-COOH;
 $NH_2$-[NLS]-[MaTadA1.1]-[programmable DNA binding domain]-[NLS]-COOH;
 $NH_2$-[NLS]-[programmable DNA binding domain]-[MaTadA1.1]-[NLS]-COOH;
 $NH_2$-[NLS]-[MaTadA1.2]-[programmable DNA binding domain]-[NLS]-COOH;
 $NH_2$-[NLS]-[programmable DNA binding domain]-[MaTadA1.2]-[NLS]-COOH;
 $NH_2$-[NLS]-[MaTadA1.3]-[programmable DNA binding domain]-[NLS]-COOH;
 $NH_2$-[NLS]-[programmable DNA binding domain]-[MaTadA1.3]-[NLS]-COOH;
 $NH_2$-[NLS]-[MaTadA1.4]-[programmable DNA binding domain]-[NLS]-COOH;
 $NH_2$-[NLS]-[programmable DNA binding domain]-[MaTadA1.4]-[NLS]-COOH;
 $NH_2$-[NLS]-[MaTadA1.5]-[programmable DNA binding domain]-[NLS]-COOH; and
 $NH_2$-[NLS]-[programmable DNA binding domain]-[MaTadA1.5]-[NLS]-COOH.

In certain embodiments, the base editors provided herein comprises an architecture selected from the group consisting of:
 $NH_2$-[NLS]-[ZoTadA1.0]-[programmable DNA binding domain]-[NLS]-COOH;
 $NH_2$-[NLS]-[programmable DNA binding domain]-[ZoTada1.0]-[NLS]-COOH;
 $NH_2$-[NLS]-[ZoTadA1.0-1]-[programmable DNA binding domain]-[NLS]-COOH;
 $NH_2$-[NLS]-[programmable DNA binding domain]-[ZoTadA1.0-1]-[NLS]-COOH;
 $NH_2$-[NLS]-[ZoTadA1.0-2]-[programmable DNA binding domain]-[NLS]-COOH;

NH₂-[NLS]-[programmable DNA binding domain]-[ZoTadA1.0-2]-[NLS]-COOH;

NH₂-[NLS]-[ZoTadA1.0-3]-[programmable DNA binding domain]-[NLS]-COOH; and

NH₂-[NLS]-[programmable DNA binding domain]-[ZoTadA1.0-3]-[NLS]-COOH.

In certain embodiments, the base editors provided herein comprises an architecture selected from the group consisting of:

NH₂-[NLS]-[ErTadA1.0]-[programmable DNA binding domain]-[NLS]-COOH;

NH₂-[NLS]-[programmable DNA binding domain]-[ErTada1.0]-[NLS]-COOH;

NH₂-[NLS]-[ErTadA1.0-1]-[programmable DNA binding domain]-[NLS]-COOH;

NH₂-[NLS]-[programmable DNA binding domain]-[ErTadA1.0-1]-[NLS]-COOH;

NH₂-[NLS]-[ErTadA1.0-2]-[programmable DNA binding domain]-[NLS]-COOH;

NH₂-[NLS]-[programmable DNA binding domain]-[ErTadA1.0-2]-[NLS]-COOH;

NH₂-[NLS]-[ErTadA1.0-3]-[programmable DNA binding domain]-[NLS]-COOH; and

NH₂-[NLS]-[programmable DNA binding domain]-[ErTadA1.0-3]-[NLS]-COOH.

In certain embodiments, the base editors provided herein comprises an architecture selected from the group consisting of:

NH₂-[NLS]-[MaTadA-WT]-[MaTadA1.0]-[programmable DNA binding domain]-[NLS]-COOH;

NH₂-[NLS]-[MaTadA1.0]-[MaTadA-WT]-[programmable DNA binding domain]-[NLS]-COOH;

NH₂-[NLS]-[programmable DNA binding domain]-[MaTadA1.0]-[MaTadA-WT]-[NLS]-COOH;

NH₂-[NLS]-[programmable DNA binding domain]-[MaTadA-WT]-[MaTadA1.0]-[NLS]-COOH;

NH₂-[NLS]-[MaTadA1.0]-[programmable DNA binding domain]-[MaTadA-WT]-[NLS]-COOH;

NH₂-[NLS]-[MaTadA-WT]-[MaTadA1.1]-[programmable DNA binding domain]-[NLS]-COOH;

NH₂-[NLS]-[MaTadA1.1]-[MaTadA-WT]-[programmable DNA binding domain]-[NLS]-COOH;

NH₂-[NLS]-[programmable DNA binding domain]-[MaTadA1.1]-[MaTadA-WT]-[NLS]-COOH;

NH₂-[NLS]-[programmable DNA binding domain]-[MaTadA-WT]-[MaTadA1.1]-[NLS]-COOH;

NH₂-[NLS]-[MaTadA1.1]-[programmable DNA binding domain]-[MaTadA-WT]-[NLS]-COOH;

NH₂-[NLS]-[ZoTadA-WT]-[ZoTadA1.0]-[programmable DNA binding domain]-[NLS]-COOH;

NH₂-[NLS]-[ZoTadA1.0]-[ZoTadA-WT]-[programmable DNA binding domain]-[NLS]-COOH;

NH₂-[NLS]-[programmable DNA binding domain]-[ZoTadA1.0]-[ZoTadA-WT]-[NLS]-COOH;

NH₂-[NLS]-[programmable DNA binding domain]-[ZoTadA-WT]-[ZoTadA1.0]-[NLS]-COOH;

NH₂-[NLS]-[ZoTadA1.0-1]-[programmable DNA binding domain]-[ZoTadA-WT]-[NLS]-COOH;

NH₂-[NLS]-[ErTadA-WT]-[ErTadA1.0]-[programmable DNA binding domain]-[NLS]-COOH;

NH₂-[NLS]-[ErTadA1.0]-[ErTadA-WT]-[programmable DNA binding domain]-[NLS]-COOH;

NH₂-[NLS]-[programmable DNA binding domain]-[ErTadA1.0]-[ErTadA-WT]-[NLS]-COOH;

NH₂-[NLS]-[programmable DNA binding domain]-[ErTadA-WT]-[ErTadA1.0]-[NLS]-COOH; and NH₂-[NLS]-[ErTadA1.0-1]-[programmable DNA binding domain]-[ErTadA-WT]-[NLS]-COOH.

In certain embodiments, the base editors provided herein comprises an architecture selected from the group consisting of:

NH₂-[NLS]-[MaTadA1.0]-[dCas9/nCas9]-[NLS]-COOH;

NH₂-[NLS]-[dCas9/nCas9]-[MaTadA1.0]-[NLS]-COOH;

NH₂-[NLS]-[MaTadA1.0-1]-[dCas9/nCas9]-[NLS]-COOH;

NH₂-[NLS]-[dCas9/nCas9]-[MaTadA1.0-1]-[NLS]-COOH;

NH₂-[NLS]-[MaTadA1.0-2]-[dCas9/nCas9]-[NLS]-COOH;

NH₂-[NLS]-[dCas9/nCas9]-[MaTadA1.0-2]-[NLS]-COOH;

NH₂-[NLS]-[MaTadA1.0-3]-[dCas9/nCas9]-[NLS]-COOH;

NH₂-[NLS]-[dCas9/nCas9]-[MaTadA1.0-3]-[NLS]-COOH;

NH₂-[NLS]-[MaTadA1.1]-[dCas9/nCas9]-[NLS]-COOH;

NH₂-[NLS]-[dCas9/nCas9]-[MaTadA1.1]-[NLS]-COOH;

NH₂-[NLS]-[MaTadA1.2]-[dCas9/nCas9]-[NLS]-COOH;

NH₂-[NLS]-[dCas9/nCas9]-[MaTadA1.2]-[NLS]-COOH;

NH₂-[NLS]-[MaTadA1.3]-[dCas9/nCas9]-[NLS]-COOH;

NH₂-[NLS]-[dCas9/nCas9]-[MaTadA1.3]-[NLS]-COOH;

NH₂-[NLS]-[MaTadA1.4]-[dCas9/nCas9]-[NLS]-COOH;

NH₂-[NLS]-[dCas9/nCas9]-[MaTadA1.4]-[NLS]-COOH;

NH₂-[NLS]-[MaTadA1.5]-[dCas9/nCas9]-[NLS]-COOH; and

NH₂-[NLS]-[dCas9/nCas9]-[MaTadA1.5]-[NLS]-COOH.

In certain embodiments, the base editors provided herein comprises an architecture selected from the group consisting of:

NH₂-[NLS]-[ZoTadA1.0]-[dCas9/nCas9]-[NLS]-COOH;

NH₂-[NLS]-[dCas9/nCas9]-[ZoTadA1.0]-[NLS]-COOH;

NH₂-[NLS]-[ZoTadA1.0-1]-[dCas9/nCas9]-[NLS]-COOH;

NH₂-[NLS]-[dCas9/nCas9]-[ZoTadA1.0-1]-[NLS]-COOH;

NH₂-[NLS]-[ZoTadA1.0-2]-[dCas9/nCas9]-[NLS]-COOH;

NH₂-[NLS]-[dCas9/nCas9]-[ZoTadA1.0-2]-[NLS]-COOH;

NH₂-[NLS]-[ZoTadA1.0-3]-[dCas9/nCas9]-[NLS]-COOH; and

NH₂-[NLS]-[dCas9/nCas9]-[ZoTadA1.0-3]-[NLS]-COOH.

In certain embodiments, the base editors provided herein comprises an architecture selected from the group consisting of:

NH₂-[NLS]-[ErTadA1.0]-[dCas9/nCas9]-[NLS]-COOH;

NH₂-[NLS]-[dCas9/nCas9]-[ErTadA1.0]-[NLS]-COOH;

NH₂-[NLS]-[ErTadA1.0-1]-[dCas9/nCas9]-[NLS]-COOH;

NH₂-[NLS]-[dCas9/nCas9]-[ErTadA1.0-1]-[NLS]-COOH;

NH$_2$-[NLS]-[ErTadA1.0-2]-[dCas9/nCas9]-[NLS]-COOH;
NH$_2$-[NLS]-[dCas9/nCas9]-[ErTadA1.0-2]-[NLS]-COOH;
NH$_2$-[NLS]-[ErTadA1.0-3]-[dCas9/nCas9]-[NLS]-COOH; and
NH$_2$-[NLS]-[dCas9/nCas9]-[ErTadA1.0-3]-[NLS]-COOH.

In certain embodiments, the base editor provided herein comprises, or substantially consists of, an amino acid sequence shown in any of SEQ ID NOs: 46 to 54, or an amino acid sequence having at least about 80%, about 85%, about 90%, about 91%, about 92%, about 93%, about 94%, about 95%, about 96%, about 97%, about 98% or about 99% sequence identity to the amino acid sequence shown in any of SEQ ID NOs: 46 to 54.

In some embodiments, the base editor provided herein comprises, or substantially consists of, an amino acid sequence shown in SEQ ID NO: 46 or an amino acid sequence having at least about 80%, about 85%, about 90%, about 91%, about 92%, about 93%, about 94%, about 95%, about 96%, about 97%, about 98% or about 99% sequence identity to the amino acid sequence shown in SEQ ID NO: 46.

In some embodiments, the base editor provided herein comprises, or substantially consists of, an amino acid sequence shown in SEQ ID NO: 47 or an amino acid sequence having at least about 80%, about 85%, about 90%, about 91%, about 92%, about 93%, about 94%, about 95%, about 96%, about 97%, about 98% or about 99% sequence identity to the amino acid sequence shown in SEQ ID NO: 47.

In some embodiments, the base editor provided herein comprises, or substantially consists of, an amino acid sequence shown in SEQ ID NO: 48 or an amino acid sequence having at least about 80%, about 85%, about 90%, about 91%, about 92%, about 93%, about 94%, about 95%, about 96%, about 97%, about 98% or about 99% sequence identity to the amino acid sequence shown in SEQ ID NO: 48.

In some embodiments, the base editor provided herein comprises, or substantially consists of, an amino acid sequence shown in SEQ ID NO: 49 or an amino acid sequence having at least about 80%, about 85%, about 90%, about 91%, about 92%, about 93%, about 94%, about 95%, about 96%, about 97%, about 98% or about 99% sequence identity to the amino acid sequence shown in SEQ ID NO: 49.

In some embodiments, the base editor provided herein comprises, or substantially consists of, an amino acid sequence shown in SEQ ID NO: 50 or an amino acid sequence having at least about 80%, about 85%, about 90%, about 91%, about 92%, about 93%, about 94%, about 95%, about 96%, about 97%, about 98% or about 99% sequence identity to the amino acid sequence shown in SEQ ID NO: 50.

In some embodiments, the base editor provided herein comprises, or substantially consists of, an amino acid sequence shown in SEQ ID NO: 51 or an amino acid sequence having at least about 80%, about 85%, about 90%, about 91%, about 92%, about 93%, about 94%, about 95%, about 96%, about 97%, about 98% or about 99% sequence identity to the amino acid sequence shown in SEQ ID NO: 51.

In some embodiments, the base editor provided herein comprises, or substantially consists of, an amino acid sequence shown in SEQ ID NO: 52 or an amino acid sequence having at least about 80%, about 85%, about 90%, about 91%, about 92%, about 93%, about 94%, about 95%, about 96%, about 97%, about 98% or about 99% sequence identity to the amino acid sequence shown in SEQ ID NO: 52.

In some embodiments, the base editor provided herein comprises, or substantially consists of, an amino acid sequence shown in SEQ ID NO: 53 or an amino acid sequence having at least about 80%, about 85%, about 90%, about 91%, about 92%, about 93%, about 94%, about 95%, about 96%, about 97%, about 98% or about 99% sequence identity to the amino acid sequence shown in SEQ ID NO: 53.

In some embodiments, the base editor provided herein comprises, or substantially consists of, an amino acid sequence shown in SEQ ID NO: 54 or an amino acid sequence having at least about 80%, about 85%, about 90%, about 91%, about 92%, about 93%, about 94%, about 95%, about 96%, about 97%, about 98% or about 99% sequence identity to the amino acid sequence shown in SEQ ID NO: 54.

Polynucleotides, Vectors and Cells

Another aspect of the disclosure provides polynucleotides encoding any of the adenosine deaminases or base editors comprising the adenosine deaminases described herein.

In some embodiments, the polynucleotides encoding the adenosine deaminases are DNA or RNA sequences. In some embodiments, the polynucleotides may be codon-optimized for expression in a eukaryotic cell (e.g., a human cell).

Exemplary polynucleotides encoding the adenosine deaminases disclosed herein comprises a nucleic acid sequence shown in any of SEQ ID NOs: 24, 25, and 28 to 31.

Another aspect of the disclosure provides a vector comprising any of the polynucleotides set forth above, especially the polynucleotides encoding any of the base editors provided herein. Vectors may be designed to clone and/or express the base editors of the disclosure. Vectors may also be designed to transfect the base editors of the disclosure into one or more cells, e.g., a target diseased eukaryotic cell for treatment with the base editors and methods disclosed herein. Vectors may be designed for expression of base editor transcripts (e.g., nucleic acid transcripts, proteins, or enzymes) in prokaryotic or eukaryotic cells. For example, base editor transcripts may be expressed in bacterial cells such as *Escherichia coli*, insect cells (using baculovirus expression vectors), yeast cells, plant cells, or mammalian cells. Alternatively, expression vectors encoding one or more base editors described herein may be transcribed and translated in vitro, for example using T7 promoter regulatory sequences and T7 polymerase.

Vectors may be introduced and propagated in a prokaryotic cell. In some embodiments, a prokaryote is used to amplify copies of a vector to be introduced into a eukaryotic cell or as an intermediate vector in the production of a vector to be introduced into a eukaryotic cell (e.g., amplifying a plasmid as part of a viral vector packaging system). In some embodiments, a prokaryote is used to amplify copies of a vector and express one or more nucleic acids, such as to provide a source of one or more proteins for delivery to a host cell or host organism. Expression of proteins in prokaryotes is most often carried out in *Escherichia coli* with vectors containing constitutive or inducible promoters.

In some embodiments, a vector is capable of driving expression of one or more sequences in mammalian cells using a mammalian expression vector. Examples of mammalian expression vectors include pCDM8 and pMT2PC.

When used in mammalian cells, the expression vector's control functions are typically provided by one or more regulatory elements. For example, commonly used promoters are derived from polyoma, adenovirus 2, cytomegalovirus, simian virus 40, and others disclosed herein and known in the art.

Some embodiments of this disclosure provide cells comprising any of the base editors or complexes provided herein. In some embodiments, the cells comprise nucleotide constructs that encodes any of the base editors provided herein. In some embodiments, the cells comprise any of the nucleotides or vectors provided herein. In some embodiments, the cell is a stem cell. In some embodiments, the cell is a human stem cell, such as a human stem and progenitor cell (HSPC). In some embodiments, the cell is a mobilized (e.g., plerixafor-mobilized) peripheral blood HSPC.

In some embodiments, a host cell is transiently or non-transiently transfected with one or more vectors described herein. In some embodiments, a cell is transfected as it naturally occurs in a subject. In some embodiments, a cell that is transfected is taken from a subject. In some embodiments, the cell is derived from cells taken from a subject, such as a cell line. A wide variety of cell lines for tissue culture are known in the art. In some embodiments, the cell has been removed from a subject and contacted ex vivo with any of the disclosed base editors, complexes, vectors, or polynucleotides.

Pharmaceutical Compositions, Treatment Methods and Uses

The present disclosure provides methods for the treatment of a subject diagnosed with a disease associated with or caused by a point mutation that may be corrected by a DNA editing base editor provided herein. For example, in some embodiments, a method is provided that comprises administering to a subject having such a disease, e.g., a cancer associated with a point mutation as described above, an effective amount of an adenosine deaminase base editor that corrects the point mutation or introduces a deactivating mutation into a disease-associated gene. In some embodiments, the disease is a proliferative disease. In some embodiments, the disease is a genetic disease. In some embodiments, the disease is a neoplastic disease. In some embodiments, the disease is a metabolic disease. In some embodiments, the disease is a lysosomal storage disease. Other diseases that may be treated by correcting a point mutation or introducing a deactivating mutation into a disease-associated gene will be known to those of skill in the art, and the disclosure is not limited in this respect.

In some embodiments, the deamination of the mutant A results in the codon encoding the wild-type amino acid. In some embodiments, the contacting is in vivo in a subject. In some embodiments, the subject has or has been diagnosed with a disease or disorder. In some embodiments, the disease or disorder is a hemoglobinopathy. In some embodiments, the disease or disorder is sickle cell disease. In some embodiments, the disease or disorder is thalassemia. In some embodiments, the disease or disorder is Glycogen storage disease type 1A, which is associated with a R83C mutation in the Glucose-6-phosphatase-alpha (G6PC) enzyme, and Stargardt macular dystrophy, which is associated with a G1961E mutation in the ATP-binding cassette, sub-family A, member 4 (ABCA4) protein. In some embodiments, the disease or disorder is phenylketonuria, von Willebrand disease (vWD), a neoplastic disease associated with a mutant PTEN or BRCA1, or Li-Fraumeni syndrome.

Some embodiments provide methods for using the base editors provided herein. In some embodiments, the base editors are used to introduce a point mutation into a nucleic acid by deaminating a target nucleobase, e.g., an A residue. In some embodiments, the deamination of the target nucleobase results in the correction of a genetic defect, e.g., in the correction of a point mutation that leads to a loss of function in a gene product. In some embodiments, the methods provided herein are used to introduce a deactivating point mutation into a gene or allele that encodes a gene product that is associated with a disease or disorder. For example, in some embodiments, methods are provided herein that employ a DNA editing base editor to introduce a deactivating point mutation into an oncogene (e.g., in the treatment of a proliferative disease). A deactivating mutation may, in some embodiments, generate a premature stop codon in a coding sequence, which results in the expression of a truncated gene product, e.g., a truncated protein lacking the function of the full-length protein.

In some embodiments, the purpose of the methods provided herein is to restore the function of a dysfunctional gene via genome editing. The nucleobase editing proteins provided herein can be validated for gene editing based human therapeutics in vitro, e.g., by correcting a disease-associated mutation in human cell culture. It will be understood by the skilled artisan that the base editors provided herein may be used to correct any single point G to A or C to T mutation.

Other aspects of the present disclosure relate to pharmaceutical compositions comprising any of the adenosine deaminases, base editors, or the base editor-gRNA complexes described herein. Still other aspects of the present disclosure relate to pharmaceutical compositions comprising any of the polynucleotides or vectors that comprise a nucleic acid segment that encodes the adenosine deaminases, base editors, or the base editor-gRNA complexes described herein.

In some embodiments, any of the base editors, gRNAs, and/or complexes described herein are provided as part of a pharmaceutical composition. In some embodiments, the pharmaceutical composition comprises any of the base editors provided herein. In some embodiments, the pharmaceutical composition comprises any of the complexes provided herein. In some embodiments pharmaceutical composition comprises a gRNA, a base editor, and a pharmaceutically acceptable excipient. Pharmaceutical compositions may optionally comprise one or more additional therapeutically active substances.

In some embodiments, compositions provided herein are formulated for delivery to a subject, for example, to a human subject, in order to effect a targeted genomic modification within the subject. In some embodiments, cells are obtained from the subject and contacted with any of the pharmaceutical compositions provided herein. In some embodiments, cells removed from a subject and contacted ex vivo with a pharmaceutical composition are re-introduced into the subject, optionally after the desired genomic modification has been effected or detected in the cells.

Formulations of the pharmaceutical compositions described herein may be prepared by any method known or hereafter developed in the art of pharmacology. In general, such preparatory methods include the step of bringing the active ingredient(s) into association with an excipient and/or one or more other accessory ingredients, and then, if necessary and/or desirable, shaping and/or packaging the product into a desired single- or multi-dose unit.

In some embodiments, the pharmaceutical composition is formulated for delivery to a subject, e.g., for gene editing. Suitable routes of administrating the pharmaceutical composition described herein include, without limitation, topical, subcutaneous, transdermal, intradermal, intralesional, intraarticular, intraperitoneal, intravesical, transmucosal, gingival, intradental, intracochlear, transtympanic, intraorgan, epidural, intrathecal, intramuscular, intravenous, intravascular, intraosseus, periocular, intratumoral, intracerebral, and intracerebroventricular administration.

In various embodiments, the base editor constructs (including, the split-constructs) may be engineered for delivery in one or more rAAV vectors. An rAAV as related to any of the methods and compositions provided herein may be of any serotype including any derivative or pseudo type (e.g., 1, 2, 3, 4, 5, 6, 7, 8, 9, 10, II, 12, 13, 2/1, 2/5, 2/8, 2/9, 3/1, 3/5, 3/8, or 3/9). An rAAV may comprise a genetic load (i.e., a recombinant nucleic acid vector that expresses a gene of interest, such as a whole or split base editor that is carried by the rAAV into a cell) that is to he delivered to a cell. An rAAV may be chimeric. As used herein, the serotype of an rAAV refers to the serotype of the capsid proteins of the recombinant virus. Non-limiting examples of derivatives and pseudo types include rAAV2/1, rAAV2/5, rAAV2/8, rAAV2/9, AAV2-AAV3 hybrid, AAVrh.10, AAVrh.74, AAVhu.14, AAV3a/3b, AAVrh32.33, AAV-HSC15, AAV-HSC17, AAVhu.37, AAVrh.8, CHt-P6, AAV2.5, AAV6.2, AAV218, AAV-HSC15/17, AAVM41, AAV9.45, AAV6 (Y445F/Y731F), AAV2.5T, AAV-HAE1/2, AAV32/83, AAVShH10, AAV2 (Y→F), AAV 8 (Y733F), AAV2.15, AAV2.4, AAVM41 and AAVr3.45.

In various embodiments, the disclosed editing methods result in an on-target DNA base editing efficiency of at least about 35%, 40%, 50%, 60%, 70%, 80%, 85%, 90%, 95%, 98%, or 99% at the target nucleobase pair. The step of contacting may result in a DNA base editing efficiency of at least about 60%, 61%, 62%, 63%, 64%, 65%, 66%, 67%, 68%, 69%, 70%, 71%, 72%, 73%, 74%, or 75%. In particular, the step of contacting results in on-target base editing efficiencies of greater than 75%. In certain embodiments, base editing efficiencies of 99% may be realized.

In some embodiments, the disclosed editing methods further result in an actual or average off-target DNA editing frequency of about 2.0% or less, 1.75% or less, 1.5% or less, 1.2% or less, 1% or less, 0.9% or less, 0.8% or less, 0.75% or less, 0.7% or less, 0.65% or less, or 0.6% or less. In some embodiments, the disclosed editing methods result in an actual or average off-target DNA editing frequency of 0.5%, less than 0.5%, less than 0.4%, less than 0.35%, less than 0.3%, less than 0.25%, less than 0.2%, or less than 0.1%.

In some embodiments, the intended edited base pair is 1, 2, 3, 4, 5, 6, 7, 8, 9, 10, 11, 12, 13, 14, 15, 16, 17, 18, 19, or 20 nucleotides upstream of the PAM site. In some embodiments, the intended edited base pair is downstream of a PAM site. In some embodiments, the intended edited base pair is 1, 2, 3, 4, 5, 6, 7, 8, 9, 10, 11, 12, 13, 14, 15, 16, 17, 18, 19, or 20 nucleotides downstream stream of the PAM site. In some embodiments, the method does not require a canonical (e g., NGG) PAM site.

In some embodiments, the target region comprises a target window, wherein the target window comprises the target nucleobase pair. In some embodiments, the target window comprises 1-10 nucleotides. In some embodiments, the target window is 1-9, 1-8, 1-7, 1-6, 1-5, 1-4, 1-3, 1-2, or 1 nucleotide in length. In some embodiments, the target window is 1, 2, 3, 4, 5, 6, 7, 8, 9, 10, 11, 12, 13, 14, 15, 16, 17, 18, 19, or 20 nucleotides in length. In some embodiments, the intended edited base pair is within the target window. In some embodiments, the target window comprises the intended edited base pair. In some embodiments, the method is performed using any of the base editors provided herein. In some embodiments, a target window is a deamination window.

In some examples, the adenosine deaminase of the adenine base editors has high editing efficiencies on adenosine A at position 3, 4, 5, 6, 7, 8 or 9 within the target window, and even more higher editing efficiencies on adenosine A at position 3, 4, 5, or 6 within the target window. In some examples, MaTadA1.0, ZoTadA1.0, or ErTadA1.0 has an editing window at positions 3-9 (narrower window indicating higher specificity), preferably positions 4-8. MaTadA1.0 was found having the highest editing efficiency in eukaryotic cells.

A further aspect of the invention provides the uses of the adenosine deaminases, base editors, polynucleotides, vectors, complexes, cells, or pharmaceutical compositions described herein in the manufacture of a medicament for treatment of a nucleobase A mutation mediated disease. A further aspect of the invention provides the adenosine deaminases, base editors, polynucleotides, vectors, complexes, cells, or pharmaceutical compositions described herein for use in treatment of a nucleobase A mutation mediated disease. The nucleobase A mutation mediated disease can be any of the disease set forth above in the present disclosure.

Sequence Listings

| SEQ ID NO: | Description | Sequences |
|---|---|---|
| 1 | MaTadA-WT (AA) | MTGSETDHIRWMRHALTLAQRAWDEGEVPVGAVLVYQGQVIGEG WNRPIGHHDPTAHAEMMALRQGGIVLQNYRLLDTTLYVTLEPCVMC AGAMVHSRIGQLIYGASDVKTGAAGSLMDVLGHPGMNHKVSVAGG VLAQECAGLLSDFFRMRRQVHKANKQATRQQSEEQ |
| 2 | MaTadA1.0 (AA) | MTGSETDHIRWMRHALTLAQRARDEGEVPVGAVLVLQGQVIGEGW NRAIGLHDPTAHAEMMALRQGGIVLQNYRLLDTTLYVTFEPCVMCA GAMVHSRIGQLIYGVSNSKRGAAGSLMNVLNYPGMNHKVSVAGGV LAQECAGLLCDFYRMPRQVFNANKQATRQQSINQ |
| 3 | MaTadA1.0-1 (AA) | MTGSETDHIRWMRHALTLAQRAKDEGEVPVGAVLVVQGQVIGEGW NRAIGVHDPTAHAEMMALRQGGIVLQNYRLLDTTLYVTWEPCVMCA GAMVHSRIGQLIYGISNSKKGAAGSLMNVLNYPGMNHKVSVAGGVL AQECAGLLCDFYRMPRQVWNANKQATRQQSINQ |

-continued

Sequence Listings

| SEQ ID NO: | Description | Sequences |
|---|---|---|
| 4 | MaTadA1.0-2(AA) | MTGSETDHIRWMRHALTLAQRAHDEGEVPVGAVLVIQGQVIGEGW NRAIGIHDPTAHAEMMALRQGGIVLQNYRLLDTTLYVTYEPCVMCAG AMVHSRIGQLIYGLSNSKHGAAGSLMNVLNYPGMNHKVSVAGGVLA QECAGLLCDFYRMPRQVYNANKQATRQQSINQ |
| 5 | MaTadA1.0-3 (AA) | MTGSETDHIRWMRHALTLAQRARDEGEVPVGAVLVPQGQVIGEGW NRAIGPHDPTAHAEMMALRQGGIVLQNYRLLDTTLYVTFEPCVMCA GAMVHSRIGQLIYGPSNSKRGAAGSLMNVLNYPGMNHKVSVAGGV LAQECAGLLCDFYRMPRQVFNANKQATRQQSINQ |
| 6 | MaTadA1.1 (AA) | MTGSETDHIRWMRHALTLAQRARDEGEVPVGAVLVLQGQVIGEGW NRAIGLHDPTAHAEMMALRQGGIVLQNYRLLDTTLYVTFEPCVMCA GAMVHSRIGQLIYGVSNSKRGAAGSLMQVLNYPGMNHKVSVAGGV LAQECAGLLCDFYRMPRQVFNANKQATRQQSINQ |
| 7 | MaTadA1.2(AA) | MTGSETDHIRWMRHALTLAQRARDEGEVPVGAVLVLQGQVIGEGW NRAIGLHDPTAHAEMMALRQGGIVLQNYRLLDTTLYVTFEPCVMCA GAMVHSRIGQLIYGVSNSKRGAAGSLMRVLNYPGMNHKVSVAGGVL AQECAGLLCDFYRMPRQVFNANKQATRQQSINQ |
| 8 | MaTadA1.3(AA) | MTGSETDHIRWMRHALTLAQRARDEGEVPVGAVLVLQGQVIGEGW NRAIGLHDPTAHAEMMALRQGGIVLQNYRLLDTTLYVTFEPCVMCA GAMVHSRIGQLIYGVSNSKKGAAGSLMNVLNYPGMNHKVSVAGGV LAQECAGLLCDFYRMPRQVFNANKQATRQQSINQ |
| 9 | MaTadA1.4(AA) | MTGSETDHIRWMRHALTLAQRARDEGEVPVGAVLVLQGQVIGEGW NRAIGLHDPTAHAEMMALRQGGIVLQNYRLLDTTLYVTFEPCVMCA GAMVHSRIGQLIYGVSNSRKGAAGSLMNVLNYPGMNHKVSVAGGV LAQECAGLLCDFYRMPRQVFNANKQATRQQSINQ |
| 10 | MaTadA1.5(AA) | MTGSETDHIRWMRHALTLAQRARDEGEVPVGAVLVLQGQVIGEGW NRAIGLHDPTAHAEMMALRQGGIVLQNYRLLDTTLYVTFEPCVMCA GAMVHSRIGQLIYGVSNSKRGAAGSLMNVLNYPGMNHKVSVAGGV LAQECAGLLCDFHRMPRQVFNANKQATRQQSINQ |
| 11 | Linker (AA) | SGGSSGGS |
| 12 | ZoTadA-WT (AA) | MSELYSDEYWMEQALERAKRAEQQNEIPVGAVVVLNNQIIGEGWN QTITLHNPTAHAEIMALEEAGLSQQNYRLVGATLYVTLEPCMCAGA IIHSRIERLVYGASDFKTGAAGSFIDLLRYPGINHCVQISSGVLQEQCSSL LSEFFRRRRQEIKQQKKSQESLLVES |
| 13 | ZoTadA1.0 (AA) | MSELYSDEYWMEQALERAKRARQQNEIPVGAVVVLNNQIIGEGWN QAITLHNPTAHAEIMALEEAGLSQQNYRLVGATLYVTFEPCMMCAGA IIHSRIERLVYGVSNVKRGAAGSFINLLNYPGINHCVQISSGVLQEQCSS LLCEFYRRPRQVINQQKKSQESLLINS |
| 14 | ZoTadA1.0-1 (AA) | MSELYSDEYWMEQALERAKRAKQQNEIPVGAVVVLNNQIIGEGWN QAITLHNPTAHAEIMALEEAGLSQQNYRLVGATLYVTWEPCMMCAG AIIHSRIERLVYGISNIKKGAAGSFINLLNYPGINHCVQISSGVLQEQCSSL LCEFYRRPRQIINQQKKSQESLLINS |
| 15 | ZoTadA1.0-2 (AA) | MSELYSDEYWMEQALERAKRAHQQNEIPVGAVVVLNNQIIGEGWN QAITLHNPTAHAEIMALEEAGLSQQNYRLVGATLYVTYEPCMMCAGA IIHSRIERLVYGLSNLKHGAAGSFINLLNYPGINHCVQISSGVLQEQCSSL LCEFYRRPRQLINQQKKSQESLLINS |
| 16 | ZoTadA1.0-3 (AA) | MSELYSDEYWMEQALERAKRARQQNEIPVGAVVVLNNQIIGEGWN QAITLHNPTAHAEIMALEEAGLSQQNYRLVGATLYVTFEPCMMCAGA IIHSRIERLVYGPSNPKRGAAGSFINLLNYPGINHCVQISSGVLQEQCSSL LCEFYRRPRQPINQQKKSQESLLINS |
| 17 | ErTadA-WT (AA) | MSDTQIDEKWMRHALTLARRAWEEGEVPVGAVLVQGDTVIGEGWN RPIGYHDPTAHAEIMALRQGGKVLENYRLLDTTLYVTLEPCVMCAGA MVHGRVGRLVFGARDEKTGAAGSLLDILGHAGMNHQVSVEQGVLA AECAAMLSNFFRQRRAEKKALRDRLRAELLKGE |
| 18 | ErTadA1.0 (AA) | MSDTQIDEKWMRHALTLARRAREEGEVPVGAVLVLGDTVIGEGWNR AIGLHDPTAHAEIMALRQGGKVLENYRLLDTTLYVTFEPCVMCAGAM VHGRVGRLVFGVRNSKRGAAGSLLNILNYAGMNHQVSVEQGVLAAE CAAMLCNFYRQPRAVFNALRDRLRAELLKIN |

| SEQ ID NO: | Description | Sequences |
|---|---|---|
| 19 | ErTadA1.0-1 (AA) | MSDTQIDEKWMRHALTLARRAKEEGEVPVGAVLVVGDTVIGEGWNR<br>AIGVHDPTAHAEIMALRQGGKVLENYRLLDTTLYVTWEPCVMCAGA<br>MVHGRVGRLVFGIRNSKKGAAGSLLNILNYAGMNHQVSVEQGVLAA<br>ECAAMLCNFYRQPRAIWNALRDRLRAELLKIN |
| 20 | ErTadA1.0-2 (AA) | MSDTQIDEKWMRHALTLARRAHEEGEVPVGAVLVIGDTVIGEGWNR<br>AIGIHDPTAHAEIMALRQGGKVLENYRLLDTTLYVTYEPCVMCAGAM<br>VHGRVGRLVFGLRNSKHGAAGSLLNILNYAGMNHQVSVEQGVLAAE<br>CAAMLCNFYRQPRALYNALRDRLRAELLKIN |
| 21 | ErTadA1.0-3 (AA) | MSDTQIDEKWMRHALTLARRAREEGEVPVGAVLVPGDTVIGEGWNR<br>AIGPHDPTAHAEIMALRQGGKVLENYRLLDTTLYVTFEPCVMCAGAM<br>VHGRVGRLVFGPRNSKRGAAGSLLNILNYAGMNHQVSVEQGVLAAE<br>CAAMLCNFYRQPRAPFNALRDRLRAELLKIN |
| 22 | dCas9(D10A & H840A) (AA) | MDKKYSIGLAIGTNSVGWAVITDEYKVPSKKFKVLGNTDRHSIKKNLIG<br>ALLFDSGETAEATRLKRTARRRYTRRKNRICYLQEIFSNEMAKVDDSFF<br>HRLEESFLVEEDKKHERHPIFGNIVDEVAYHEKYPTIYHLRKKLVDSTDK<br>ADLRLIYLALAHMIKFRGHFLIEGDLNPDNSDVDKLFIQLVQTYNQLFE<br>ENPINASGVDAKAILSARLSKSRRLENLIAQLPGEKKNGLFGNLIALSLG<br>LTPNFKSNFDLAEDAKLQLSKDTYDDDLDNLLAQIGDQYADLFLAAKN<br>LSDAILLSDILRVNTEITKAPLSASMIKRYDEHHQDLTLLKALVRQQLPEK<br>YKEIFFDQSKNGYAGYIDGGASQEEFYKFIKPILEKMDGTEELLVKLNRE<br>DLLRKQRTFDNGSIPHQIHLGELHAILRRQEDFYPFLKDNREKIEKILTFR<br>IPYYVGPLARGNSRFAWMTRKSEETITPWNFEEVVDKGASAQSFIER<br>MTNFDKNLPNEKVLPKHSLLYEYFTVYNELTKVKYVTEGMRKPAFLSG<br>EQKKAIVDLLFKTNRKVTVKQLKEDYFKKIECFDSVEISGVEDRFNASLG<br>TYHDLLKIIKDKDFLDNEENEDILEDIVLTLTLFEDREMIEERLKTYAHLFD<br>DKVMKQLKRRRYTGWGRLSRKLINGIRDKQSGKTILDFLKSDGFANRN<br>FMQLIHDDSLTFKEDIQKAQVSGQGDSLHEHIANLAGSPAIKKGILQTV<br>KVVDELVKVMGRHKPENIVIEMARENQTTQKGQKNSRERMKRIEEGI<br>KELGSQILKEHPVENTQLQNEKLYLYYLQNGRDMYVDQELDINRLSDY<br>DVDAIVPQSFLKDDSIDNKVLTRSDKNRGKSDNVPSEEVVKKMKNYW<br>RQLLNAKLITQRKFDNLTKAERGGLSELDKAGFIKRQLVETRQITKHVA<br>QILDSRMNTKYDENDKLIREVKVITLKSKLVSDFRKDFQFYKVREINNY<br>HHAHDAYLNAVVGTALIKKYPKLESEFVYGDYKVYDVRKMIAKSEQEIG<br>KATAKYFFYSNIMNFFKTEITLANGEIRKRPLIETNGETGEIVWDKGRDF<br>ATVRKVLSMPQVNIVKKTEVQTGGFSKESILPKRNSDKLIARKKDWDP<br>KKYGGFDSPTVAYSVLVVAKVEKGKSKKLKSVKELLGITIMERSSFEKNPI<br>DFLEAKGYKEVKKDLIIKLPKYSLFELENGRKRMLASAGELQKGNELALP<br>SKYVNFLYLASHYEKLKGSPEDNEQKQLFVEQHKHYLDEIIEQISEFSKR<br>VILADANLDKVLSAYNKHRDKPIREQAENIIHLFTLTNLGAPAAFKYFDT<br>TIDRKRYTSTKEVLDATLIHQSITGLYETRIDLSQLGGD* |
| 23 | nCas9(D10A) (AA) | MDKKYSIGLAIGTNSVGWAVITDEYKVPSKKFKVLGNTDRHSIKKNLIG<br>ALLFDSGETAEATRLKRTARRRYTRRKNRICYLQEIFSNEMAKVDDSFF<br>HRLEESFLVEEDKKHERHPIFGNIVDEVAYHEKYPTIYHLRKKLVDSTDK<br>ADLRLIYLALAHMIKFRGHFLIEGDLNPDNSDVDKLFIQLVQTYNQLFE<br>ENPINASGVDAKAILSARLSKSRRLENLIAQLPGEKKNGLFGNLIALSLG<br>LTPNFKSNFDLAEDAKLQLSKDTYDDDLDNLLAQIGDQYADLFLAAKN<br>LSDAILLSDILRVNTEITKAPLSASMIKRYDEHHQDLTLLKALVRQQLPEK<br>YKEIFFDQSKNGYAGYIDGGASQEEFYKFIKPILEKMDGTEELLVKLNRE<br>DLLRKQRTFDNGSIPHQIHLGELHAILRRQEDFYPFLKDNREKIEKILTFR<br>IPYYVGPLARGNSRFAWMTRKSEETITPWNFEEVVDKGASAQSFIER<br>MTNFDKNLPNEKVLPKHSLLYEYFTVYNELTKVKYVTEGMRKPAFLSG<br>EQKKAIVDLLFKTNRKVTVKQLKEDYFKKIECFDSVEISGVEDRFNASLG<br>TYHDLLKIIKDKDFLDNEENEDILEDIVLTLTLFEDREMIEERLKTYAHLFD<br>DKVMKQLKRRRYTGWGRLSRKLINGIRDKQSGKTILDFLKSDGFANRN<br>FMQLIHDDSLTFKEDIQKAQVSGQGDSLHEHIANLAGSPAIKKGILQTV<br>KVVDELVKVMGRHKPENIVIEMARENQTTQKGQKNSRERMKRIEEGI<br>KELGSQILKEHPVENTQLQNEKLYLYYLQNGRDMYVDQELDINRLSDY<br>DVDHIVPQSFLKDDSIDNKVLTRSDKNRGKSDNVPSEEVVKKMKNYW<br>RQLLNAKLITQRKFDNLTKAERGGLSELDKAGFIKRQLVETRQITKHVA<br>QILDSRMNTKYDENDKLIREVKVITLKSKLVSDFRKDFQFYKVREINNY<br>HHAHDAYLNAVVGTALIKKYPKLESEFVYGDYKVYDVRKMIAKSEQEIG<br>KATAKYFFYSNIMNFFKTEITLANGEIRKRPLIETNGETGEIVWDKGRDF<br>ATVRKVLSMPQVNIVKKTEVQTGGFSKESILPKRNSDKLIARKKDWDP<br>KKYGGFDSPTVAYSVLVVAKVEKGKSKKLKSVKELLGITIMERSSFEKNPI<br>DFLEAKGYKEVKKDLIIKLPKYSLFELENGRKRMLASAGELQKGNELALP<br>SKYVNFLYLASHYEKLKGSPEDNEQKQLFVEQHKHYLDEIIEQISEFSKR<br>VILADANLDKVLSAYNKHRDKPIREQAENIIHLFTLTNLGAPAAFKYFDT<br>TIDRKRYTSTKEVLDATLIHQSITGLYETRIDLSQLGGD* |

Sequence Listings

| SEQ ID NO: | Description | Sequences |
|---|---|---|
| 24 | MaTadA1.0 (DNA, prokaryotic) | ATGACCGGTTCCGAAACTGACCACATCCGTTGGATGCGCCACGCAC<br>TGACCCTGGCACAGCGTGCTCGTGATGAAGGTGAAGTACCGGTAG<br>GTGCCGTTCTGGTTCTGCAAGGTCAGGTTATCGGCGAGGGTTGGAA<br>TCGTGCCATTGGTCTGCACGATCCGACTGCTCATGCTGAGATGATGG<br>CCCTGCGTCAGGGCGGCATTGTTCTGCAGAACTATCGTCTGCTGGA<br>CACCCACCCTGTACGTAACTTTCGAACCGTGCGTCATGTGCGCTGGTG<br>CGATGGTTCACTCTCGTATCGGCCAGCTGATTTACGGTGTCTCTAACA<br>GCAAACGTGGTGCCGCGGGTAGCCTGATGAACGTTCTGAATTACCC<br>GGGCATGAACCACAAGGTTTCTGTTGCTGGTGGTGTTCTGGCTCAG<br>GAATGCGCGGGCCTGCTGTGCGATTTTTACCGTATGCCGCGTCAGG<br>TCTTCAACGCGAACAAACAGGCGACCCGTCAACAATCCATCAACCA<br>G |
| 25 | MaTadA1.0 (DNA, eukaryotic) | ATGACAGGCAGTGAAACCGACCATATTAGATGGATGAGACATGCCC<br>TCACACTGGCCCAGAGAGCTAGAGATGAAGGTGAGGTTCCCGTGG<br>GAGCCGTGCTGGTGCTGCAGGGCCAGGTTATCGGCGAAGGCTGGA<br>ACAGGGCCATTGGCCTCCACGATCCCACCGCTCATGCAGAGATGAT<br>GGCCCTCAGACAAGGCGGAATTGTCCTGCAGAACTACAGGCTCCTG<br>GACACAACACTCTATGTGACCTTTGAACCCTGTGTTATGTGCGCTGG<br>CGCAATGGTTCATTCACGCATTGGACAGCTCATCTATGGCGTGAGCA<br>ATAGTAAACGCGGCGCTGCCGGGAGCCTGATGAACGTCCTGAATTA<br>TCCCGGTATGAATCATAAAGTCTCCGTCGCCGGAGGCGTGCTGGCA<br>CAAGAGTGTGCAGGGCTGCTGTGTGACTTTTACCGGATGCCTAGGC<br>AAGTTTTCAACGCTAACAAGCAGGCTACCCGCCAGCAGAGCATCAA<br>TCAG |
| 26 | Linker (AA) | SGGSSGGSSGSETPGTSESATPESSGGSSGGS |
| 27 | Linker (AA) | SGGS |
| 28 | ZoTadA1.0 (DNA, prokaryotic) | ATGAGCGAACTGTATAGCGACGAATACTGGATGGAACAAGCACTGG<br>AACGTGCTAAACGTGCCCGTCAGCAGAACGAAATCCCAGTTGGTGC<br>TGTTGTGGTCCTGAACAACCAGATCATCGGTGAAGGCTGGAACCAG<br>GCAATTACCCTGCATAACCCTACCGCACACGCAGAAATCATGGCGCT<br>GGAAGAAGCCGGCCTGTCTCAGCAAATTACCGTCTGGTTGGCGCG<br>ACTCTGTACGTGACTTTCGAACCGTGTATGATGTGCGCTGGCGCTAT<br>TATTCACTCCCGCATCGAACGTCTGGTGTACGCGTGTCTAACGTTA<br>AACGCGGCGCGGCTGGTTCCTTCATTAATCTGCTGAACTACCCGGG<br>CATCAACCACTGCGTTCAGATTAGCTCCGGCGTGCTGCAAGAACAG<br>TGTTCTTCCCTGCTGTGTGAATTCTACCGTCGTCCTCGTCAGGTTATC<br>AACCAGCAGAAAAAGAGCCAGGAGTCCCTGCTGATTAACTCC |
| 29 | ZoTadA1.0 (DNA, eukaryotic) | ATGTCTGAGCTGTATTCTGACGAGTATTGGATGGAGCAAGCCCTGG<br>AAAGAGCTAAACGGGCTCGCCAGCAGAATGAGATTCCCGTCGGCG<br>CCGTGGTGGTGCTGAATAATCAGATCATAGGTGAGGGTTGGAATCA<br>GGCCATTACTCTGCACAACCCAACCGCCCACGCCGAGATTATGGCCC<br>TGGAAGAAGCAGGGCTGTCACAACAGAACTACCGCCTGGTCGGCG<br>CTACTCTGTACGTCACATTTGAGCCCTGTATGATGTGCTGGCGCCA<br>TTATCCACTCCCGCATCGAAAGACTGGTGTATGGTGTGTCCAATGTG<br>AAACGCGGCGCAGCCGGATCTTTCATCAACCTGCTCAATTATCCAGG<br>GATTAACCACTGCGTCCAAATTTCTAGTGGCGTCCTGCAGGAACAAT<br>GCTCATCCCTCCTGTGCGAGTTTTATAGAAGGCCACGCCAGGTGATT<br>AATCAGCAAAAGAAGTCCCAAGAGAGTCTGCTGATCAACAGT |
| 30 | ErTadA1.0 (DNA, prokaryotic) | ATGTCCGATACCCAGATCGATGAAAAGTGGATGCGCCATGCCCTGAC<br>CCTGGCCCGCCGTGCTCGTGAAGAAGGCGAAGTACCGGTTGGTGC<br>TGTACTGGTCCTGGGCGATACCGTTATCGGTGAAGGTTGGAACCGT<br>GCGATTGGTCTGCACGACCCGACCGCTCACGCGGAGATTATGGCAC<br>TGCGTCAAGGCGGCAAGGTTCTGGAAAACTACCGCTGCTGGACA<br>CCACCCTGTATGTTACCTTCGAGCCGTGTGTAATGTGTGCGGGTGCG<br>ATGGTTCATGGTCGTGTCGGTCGTCTGGTTTTCGGTGTGCGTAACTC<br>TAAACGTGGTGCTGCGGGTAGCCTGCTGAATATCCTGAACTACGCG<br>GGTATGAACCATCAGGTCTCTGTTGAGCAGGGTGTACTGGCGGCTG<br>AATGCGCTGCCATGCTGTGTAACTTCTACCGTCAGCCTCGTGCTGTTT<br>TCAACGCTCTGCGTGATCGTCTGCGTGCGGAGCTGCTGAAAATCAA<br>C |
| 31 | ErTadA1.0 (DNA, eukaryotic) | ATGAGTGATACACAGATCGACGAGAAATGGATGAGACACGCCCTCA<br>CACTGGCCAGGAGGGCAAGGGAGGAGGGCGAAGTCCCTGTCGGA<br>GCTGTGCTGGTCCTCGGCGATACCGTGATTGGTGAGGGCTGGAATA<br>GAGCTATTGGCCTGCATGATCCTACAGCACACGCTGAAATCATGGCA<br>CTCCGGCAAGGCGGCAAGGTTCTGGAGAACTATCGCCTGCTGGAC<br>ACAACCCTGTACGTCACCTTTGAACCATGCGTCATGTGTGCCGGAGC<br>AATGGTGCACGGCAGAGTGGGACGGCTGGTCTTCGGCGTGCGGAA |

Sequence Listings

| SEQ ID NO: | Description | Sequences |
|---|---|---|
|  |  | CAGCAAACGCGGTGCTGCAGGTTCCCTCCTGAACATACTGAATTAC GCAGGAATGAACCATCAGGTGAGCGTTGAGCAGGGAGTCCTGGCT GCAGAATGCGCCGCTATGCTCTGCAACTTTTACAGGCAGCCAAGGG CCGTGTTCAACGCCCTCCGCGACAGACTGAGGGCCGAACTCCTGAA AATCAAT |
| 32 | SV40 NLS (DNA) | CCCAAGAAGAAGAGGAAAGTC |
| 33 | SV40 NLS (AA) | PKKKRKV |
| 34 | NLS (AA) | MDSLLMNRRKFLYQFKNVRWAKGRRETYLC |
| 35 | NLS (AA) | KRTADGSEFESPKKKRKV |
| 36 | NLS (AA) | KRTADGSEFEPKKKRKV |
| 37 | Linker (AA) | GGGS |
| 38 | Linker (AA) | SGGGS |
| 39 | Linker (AA) | SGSETPGTSESATPES |
| 40 | Linker (DNA) | TCCGGAGGATCTAGCGGAGGCTCC |
| 41 | Linker (DNA) | AGCGGGGGCAGCAGCGGGGGGTCA |
| 42 | ccdB1 initiation codon sgRNA (5'-3') | CTGCATTTATGTCAGACTTG |
| 43 | ccdB1 stop codon sgRNA (5'-3') | ATATAGCTAAGATGTCACGG |
| 44 | Hek-2 sgRNA (5'-3') | GAACACAAAGCATAGACTGC |
| 45 | p992L sgRNA (5'-3') | GCGTGAGCGTGGCCAGCCCCA |
| 46 | MaTadA1.0-Cas9(D10A) (AA) | MTGSETDHIRWMRHALTLAQRARDEGEVPVGAVLVLQGQVIGEGW NRAIGLHDPTAHAEMMALRQGGIVLQNYRLLDTTLYVTFEPCVMCA GAMVHSRIGQLIYGVSNSKRGAAGSLMNVLNYPGMNHKVSVAGGV LAQECAGLLCDFYRMPRQVFNANKQATRQQSINQSGGSSGGSSGSE TPGTSESATPESSGGSSGGSDKKYSIGLAIGTNSVGWAVITDEYKVPSK KFKVLGNTDRHSIKKNLIGALLFDSGETAEATRLKRTARRRYTRRKNRIC YLQEIFSNEMAKVDDSFFHRLEESFLVEEDKKHERHPIFGNIVDEVAYH EKYPTIYHLRKKLVDSTDKADLRLIYLALAHMIKFRGHFLIEGDLNPDNS DVDKLFIQLVQTYNQLFEENPINASGVDAKAILSARLSKSRRLENLIAQL PGEKKNGLFGNLIALSLGLTPNFKSNFDLAEDAKLQLSKDTYDDDLDNL LAQIGDQYADLFLAAKNLSDAILLSDILRVNTEITKAPLSASMIKRYDEH HQDLTLLKALVRQQLPEKYKEIFFDQSKNGYAGYIDGGASQEEFYKFIK PILEKMDGTEELLVKLNREDLLRKQRTFDNGSIPHQIHLGELHAILRRQE DFYPFLKDNREKIEKILTFRIPYYVGPLARGNSRFAWMTRKSEETITPW NFEEVVDKGASAQSFIERMTNFDKNLPNEKVLPKHSLLYEYFTVYNELT KVKYVTEGMRKPAFLSGEQKKAIVDLLFKTNRKVTVKQLKEDYFKKIEC FDSVEISGVEDRFNASLGTYHDLLKIIKDKDFLDNEENEDILEDIVLTLTLF EDREMIEERLKTYAHLFDDKVMKQLKRRRYTGWGRLSRKLINGIRDKQ SGKTILDFLKSDGFANRNFMQLIHDDSLTFKEDIQKAQVSGQGDSLHE HIANLAGSPAIKKGILQTVKVVDELVKVMGRHKPENIVIEMARENQTT QKGQKNSRERMKRIEEGIKELGSQILKEHPVENTQLQNEKLYLYYLQN GRDMYVDQELDINRLSDYDVDHIVPQSFLKDDSIDNKVLTRSDKNRG KSDNVPSEEVVKKMKNYWRQLLNAKLITQRKFDNLTKAERGGLSELD KAGFIKRQLVETRQITKHVAQILDSRMNTKYDENDKLIREVKVITLKSKL VSDFRKDFQFYKVREINNYHHAHDAYLNAVVGTALIKKYPKLESEFVYG DYKVYDVRKMIAKSEQEIGKATAKYFFYSNIMNFFKTEITLANGEIRKRP LIETNGETGEIVWDKGRDFATVRKVLSMPQVNIVKKTEVQTGGFSKESI LPKRNSDKLIARKKDWDPKKYGGFDSPTVAYSVLVVAKVEKGKSKKLKS VKELLGITIMERSSFEKNPIDFLEAKGYKEVKKDLIIKLPKYSLFELENGRK RMLASAGELQKGNELALPSKYVNFLYLASHYEKLKGSPEDNEQKQLFV EQHKHYLDEIIEQISEFSKRVILADANLDKVLSAYNKHRDKPIREQAENII HLFTLTNLGAPAAFKYFDTTIDRKRYTSTKEVLDATLIHQSITGLYETRIDL SQLGGD |

| SEQ ID NO: | Description | Sequences |
|---|---|---|
| 47 | SV40 NLS-MaTadA1.0-linker-Cas9(D10A)-SV40 NLS (AA) | PKKKRKVMTGSETDHIRWMRHALTLAQRARDEGEVPVGAVLVLQGQ VIGEGWNRAIGLHDPTAHAEMMALRQGGIVLQNYRLLDTTLYVTFEP CVMCAGAMVHSRIGQLIYGVSNSKRGAAGSLMNVLNYPGMNHKVS VAGGVLAQECAGLLCDFYRMPRQVFNANKQATRQQSINQSGGSSGG SSGSETPGTSESATPESSGGSSGGSDKKYSIGLAIGTNSVGWAVITDEY KVPSKKFKVLGNTDRHSIKKNLIGALLFDSGETAEATRLKRTARRRYTRR KNRICYLQEIFSNEMAKVDDSFFHRLEESFLVEEDKKHERHPIFGNIVDE VAYHEKYPTIYHLRKKLVDSTDKADLRLIYLALAHMIKFRGHFLIEGDLN PDNSDVDKLFIQLVQTYNQLFEENPINASGVDAKAILSARLSKSRRLEN LIAQLPGEKKNGLFGNLIALSLGLTPNFKSNFDLAEDAKLQLSKDTYDD DLDNLLAQIGDQYADLFLAAKNLSDAILLSDILRVNTEITKAPLSASMIK RYDEHHQDLTLLKALVRQQLPEKYKEIFFDQSKNGYAGYIDGGASQEE FYKFIKPILEKMDGTEELLVKLNREDLLRKQRTFDNGSIPHQIHLGELHA ILRRQEDFYPFLKDNREKIEKILTFRIPYYVGPLARGNSRFAWMTRKSEE TITPWNFEEVVDKGASAQSFIERMTNFDKNLPNEKVLPKHSLLYEYFT VYNELTKVKYVTEGMRKPAFLSGEQKKAIVDLLFKTNRKVTVKQLKEDY FKKIECFDSVEISGVEDRFNASLGTYHDLLKIIKDKDFLDNEENEDILEDI VLTLTLFEDREMIEERLKTYAHLFDDKVMKQLKRRRYTGWGRLSRKLIN GIRDKQSGKTILDFLKSDGFANRNFMQLIHDDSLTFKEDIQKAQVSGQ GDSLHEHIANLAGSPAIKKGILQTVKVVDELVKVMGRHKPENIVIEMA RENQTTQKGQKNSRERMKRIEEGIKELGSQILKEHPVENTQLQNEKLY LYYLQNGRDMYVDQELDINRLSDYDVDHIVPQSFLKDDSIDNKVLTRS DKNRGKSDNVPSEEVVKKMKNYWRQLLNAKLITQRKFDNLTKAERG GLSELDKAGFIKRQLVETRQITKHVAQILDSRMNTKYDENDKLIREVKV ITLKSKLVSDFRKDFQFYKVREINNYHHAHDAYLNAVVGTALIKKYPKLE SEFVYGDYKVYDVRKMIAKSEQEIGKATAKYFFYSNIMNFFKTEITLAN GEIRKRPLIETNGETGEIVWDKGRDFATVRKVLSMPQVNIVKKTEVQT GGFSKESILPKRNSDKLIARKKDWDPKKYGGFDSPTVAYSVLVVAKVEK GKSKKLKSVKELLGITIMERSSFEKNPIDFLEAKGYKEVKKDLIIKLPKYSL FELENGRKRMLASAGELQKGNELALPSKYVNFLYLASHYEKLKGSPED NEQKQLFVEQHKHYLDEIIEQISEFSKRVILADANLDKVLSAYNKHRDK PIREQAENIIHLFTLTNLGAPAAFKYFDTTIDRKRYTSTKEVLDATLIHQSI TGLYETRIDLSQLGGDPKKKRKV |
| 48 | SV40 NLS-MaTadA1.0-linker-Cas9(D10A & H840A)-SV40 NLS (AA) | PKKKRKVMTGSETDHIRWMRHALTLAQRARDEGEVPVGAVLVLQGQ VIGEGWNRAIGLHDPTAHAEMMALRQGGIVLQNYRLLDTTLYVTFEP CVMCAGAMVHSRIGQLIYGVSNSKRGAAGSLMNVLNYPGMNHKVS VAGGVLAQECAGLLCDFYRMPRQVFNANKQATRQQSINQSGGSSGG SSGSETPGTSESATPESSGGSSGGSDKKYSIGLAIGTNSVGWAVITDEY KVPSKKFKVLGNTDRHSIKKNLIGALLFDSGETAEATRLKRTARRRYTRR KNRICYLQEIFSNEMAKVDDSFFHRLEESFLVEEDKKHERHPIFGNIVDE VAYHEKYPTIYHLRKKLVDSTDKADLRLIYLALAHMIKFRGHFLIEGDLN PDNSDVDKLFIQLVQTYNQLFEENPINASGVDAKAILSARLSKSRRLEN LIAQLPGEKKNGLFGNLIALSLGLTPNFKSNFDLAEDAKLQLSKDTYDD DLDNLLAQIGDQYADLFLAAKNLSDAILLSDILRVNTEITKAPLSASMIK RYDEHHQDLTLLKALVRQQLPEKYKEIFFDQSKNGYAGYIDGGASQEE FYKFIKPILEKMDGTEELLVKLNREDLLRKQRTFDNGSIPHQIHLGELHA ILRRQEDFYPFLKDNREKIEKILTFRIPYYVGPLARGNSRFAWMTRKSEE TITPWNFEEVVDKGASAQSFIERMTNFDKNLPNEKVLPKHSLLYEYFT VYNELTKVKYVTEGMRKPAFLSGEQKKAIVDLLFKTNRKVTVKQLKEDY FKKIECFDSVEISGVEDRFNASLGTYHDLLKIIKDKDFLDNEENEDILEDI VLTLTLFEDREMIEERLKTYAHLFDDKVMKQLKRRRYTGWGRLSRKLIN GIRDKQSGKTILDFLKSDGFANRNFMQLIHDDSLTFKEDIQKAQVSGQ GDSLHEHIANLAGSPAIKKGILQTVKVVDELVKVMGRHKPENIVIEMA RENQTTQKGQKNSRERMKRIEEGIKELGSQILKEHPVENTQLQNEKLY LYYLQNGRDMYVDQELDINRLSDYDVDAIVPQSFLKDDSIDNKVLTRS DKNRGKSDNVPSEEVVKKMKNYWRQLLNAKLITQRKFDNLTKAERG GLSELDKAGFIKRQLVETRQITKHVAQILDSRMNTKYDENDKLIREVKV ITLKSKLVSDFRKDFQFYKVREINNYHHAHDAYLNAVVGTALIKKYPKLE SEFVYGDYKVYDVRKMIAKSEQEIGKATAKYFFYSNIMNFFKTEITLAN GEIRKRPLIETNGETGEIVWDKGRDFATVRKVLSMPQVNIVKKTEVQT GGFSKESILPKRNSDKLIARKKDWDPKKYGGFDSPTVAYSVLVVAKVEK GKSKKLKSVKELLGITIMERSSFEKNPIDFLEAKGYKEVKKDLIIKLPKYSL FELENGRKRMLASAGELQKGNELALPSKYVNFLYLASHYEKLKGSPED NEQKQLFVEQHKHYLDEIIEQISEFSKRVILADANLDKVLSAYNKHRDK PIREQAENIIHLFTLTNLGAPAAFKYFDTTIDRKRYTSTKEVLDATLIHQSI TGLYETRIDLSQLGGDSGGSPKKKRKV |
| 49 | ZoTadA1.0-Cas9(D10A) (AA) | MSELYSDEYWMEQALERAKRARQQNEIPVGAVVVLNNQIIGEGWN QAITLHNPTAHAEIMALEEAGLSQQNYRLVGATLYVTFEPCMMCAGA IIHSRIERLVYGVSNVKRGAAGSFINLLNYPGINHCVQISSGVLQEQCSS LLCEFYRRPRQVINQQKKSQESLLINSSGGSSGGSSGETPGTSESATPE SSGGSSGGSDKKYSIGLAIGTNSVGWAVITDEYKVPSKKFKVLGNTDR HSIKKNLIGALLFDSGETAEATRLKRTARRRYTRRKNRICYLQEIFSNEM |

| SEQ ID NO: | Description | Sequences |
|---|---|---|
| | | AKVDDSFFHRLEESFLVEEDKKHERHPIFGNIVDEVAYHEKYPTIYHLRK KLVDSTDKADLRLIYLALAHMIKFRGHFLIEGDLNPDNSDVDKLFIQLV QTYNQLFEENPINASGVDAKAILSARLSKSRRLENLIAQLPGEKKNGLF GNLIALSLGLTPNFKSNFDLAEDAKLQLSKDTYDDDLDNLLAQIGDQYA DLFLAAKNLSDAILLSDILRVNTEITKAPLSASMIKRYDEHHQDLTLLKAL VRQQLPEKYKEIFFDQSKNGYAGYIDGGASQEEFYKFIKPILEKMDGTE ELLVKLNREDLLRKQRTFDNGSIPHQIHLGELHAILRRQEDFYPFLKDNR EKIEKILTFRIPYYVGPLARGNSRFAWMTRKSEETITPWNFEEVVDKGA SAQSFIERMTNFDKNLPNEKVLPKHSLLYEYFTVYNELTKVKYVTEGMR KPAFLSGEQKKAIVDLLFKTNRKVTVKQLKEDYFKKIECFDSVEISGVED RFNASLGTYHDLLKIIKDKDFLDNEENEDILEDIVLTLTLFEDREMIEERL KTYAHLFDDKVMKQLKRRRYTGWGRLSRKLINGIRDKQSGKTILDFLKS DGFANRNFMQLIHDDSLTFKEDIQKAQVSGQGDSLHEHIANLAGSPAI KKGILQTVKVVDELVKVMGRHKPENIVIEMARENQTTQKGQKNSRER MKRIEEGIKELGSQILKEHPVENTQLQNEKLYLYYLQNGRDMYVDQEL DINRLSDYDVDHIVPQSFLKDDSIDNKVLTRSDKNRGKSDNVPSEEVV KKMKNYWRQLLNAKLITQRKFDNLTKAERGGLSELDKAGFIKRQLVET RQITKHVAQILDSRMNTKYDENDKLIREVKVITLKSKLVSDFRKDFQFY KVREINNYHHAHDAYLNAVVGTALIKKYPKLESEFVYGDYKVYDVRKM IAKSEQEIGKATAKYFFYSNIMNFFKTEITLANGEIRKRPLIETNGETEIV WDKGRDFATVRKVLSMPQVNIVKKTEVQTGGFSKESILPKRNSDKLIA RKKDWDPKKYGGFDSPTVAYSVLVVAKVEKGKSKKLKSVKELLGITIME RSSFEKNPIDFLEAKGYKEVKKDLIIKLPKYSLFELENGRKRMLASAGEL QKGNELALPSKYVNFLYLASHYEKLKGSPEDNEQKQLFVEQHKHYLDEI IEQISEFSKRVILADANLDKVLSAYNKHRDKPIREQAENIIHLFTLTNLGA PAAFKYFDTTIDRKRYTSTKEVLDATLIHQSITGLYETRIDLSQLGGD |
| 50 | SV40 NLS-ZoTadA1.0-linker-Cas9(D10A)-SV40 NLS (AA) | PKKKRKVMSELYSDEYWMEQALERAKRARQQNEIPVGAVVVLNNQII GEGWNQAITLHNPTAHAEIMALEEAGLSQQNYRLVGATLYVTFEPCM MCAGAIIHSRIERLVYGVSNVKRGAAGSFINLLNYPGINHCVQISSGVL QEQCSSLLCEFYRRPRQVINQQKKSQESLLINSSGSETPGTSESATPESD KKYSIGLAIGTNSVGWAVITDEYKVPSKKFKVLGNTDRHSIKKNLIGALL FDSGETAEATRLKRTARRRYTRRKNRICYLQEIFSNEMAKVDDSFFHRL EESFLVEEDKKHERHPIFGNIVDEVAYHEKYPTIYHLRKKLVDSTDKADL RLIYLALAHMIKFRGHFLIEGDLNPDNSDVDKLFIQLVQTYNQLFEENPI NASGVDAKAILSARLSKSRRLENLIAQLPGEKKNGLFGNLIALSLGLTPN FKSNFDLAEDAKLQLSKDTYDDDLDNLLAQIGDQYADLFLAAKNLSDAI LLSDILRVNTEITKAPLSASMIKRYDEHHQDLTLLKALVRQQLPEKYKEIF FDQSKNGYAGYIDGGASQEEFYKFIKPILEKMDGTEELLVKLNREDLLR KQRTFDNGSIPHQIHLGELHAILRRQEDFYPFLKDNREKIEKILTFRIPYY VGPLARGNSRFAWMTRKSEETITPWNFEEVVDKGASAQSFIERMTNF DKNLPNEKVLPKHSLLYEYFTVYNELTKVKYVTEGMRKPAFLSGEQKKA IVDLLFKTNRKVTVKQLKEDYFKKIECFDSVEISGVEDRFNASLGTYHDL LKIIKDKDFLDNEENEDILEDIVLTLTLFEDREMIEERLKTYAHLFDDKVM KQLKRRRYTGWGRLSRKLINGIRDKQSGKTILDFLKSDGFANRNFMQL IHDDSLTFKEDIQKAQVSGQGDSLHEHIANLAGSPAIKKGILQTVKVVD ELVKVMGRHKPENIVIEMARENQTTQKGQKNSRERMKRIEEGIKELG SQILKEHPVENTQLQNEKLYLYYLQNGRDMYVDQELDINRLSDYDVDH IVPQSFLKDDSIDNKVLTRSDKNRGKSDNVPSEEVVKKMKNYWRQLL NAKLITQRKFDNLTKAERGGLSELDKAGFIKRQLVETRQITKHVAQILDS RMNTKYDENDKLIREVKVITLKSKLVSDFRKDFQFYKVREINNYHHAH DAYLNAVVGTALIKKYPKLESEFVYGDYKVYDVRKMIAKSEQEIGKATA KYFFYSNIMNFFKTEITLANGEIRKRPLIETNGETGEIVWDKGRDFATVR KVLSMPQVNIVKKTEVQTGGFSKESILPKRNSDKLIARKKDWDPKKYG GFDSPTVAYSVLVVAKVEKGKSKKLKSVKELLGITIMERSSFEKNPIDFLE AKGYKEVKKDLIIKLPKYSLFELENGRKRMLASAGELQKGNELALPSKYV NFLYLASHYEKLKGSPEDNEQKQLFVEQHKHYLDEIIEQISEFSKRVILAD ANLDKVLSAYNKHRDKPIREQAENIIHLFTLTNLGAPAAFKYFDTTIDRK RYTSTKEVLDATLIHQSITGLYETRIDLSQLGGDPKKKRKV |
| 51 | SV40 NLS-ZoTadA1.0-linker-Cas9(D10A & H840A)-linker-SV40 NLS (AA) | PKKKRKVMSELYSDEYWMEQALERAKRARQQNEIPVGAVVVLNNQII GEGWNQAITLHNPTAHAEIMALEEAGLSQQNYRLVGATLYVTFEPCM MCAGAIIHSRIERLVYGVSNVKRGAAGSFINLLNYPGINHCVQISSGVL QEQCSSLLCEFYRRPRQVINQQKKSQESLLINSSGGSSGGSSGSETPGT SESATPESSGGSSGGSDKKYSIGLAIGTNSVGWAVITDEYKVPSKKFKVL GNTDRHSIKKNLIGALLFDSGETAEATRLKRTARRRYTRRKNRICYLQEI FSNEMAKVDDSFFHRLEESFLVEEDKKHERHPIFGNIVDEVAYHEKYPT IYHLRKKLVDSTDKADLRLIYLALAHMIKFRGHFLIEGDLNPDNSDVDKL FIQLVQTYNQLFEENPINASGVDAKAILSARLSKSRRLENLIAQLPGEKK NGLFGNLIALSLGLTPNFKSNFDLAEDAKLQLSKDTYDDDLDNLLAQIG DQYADLFLAAKNLSDAILLSDILRVNTEITKAPLSASMIKRYDEHHQDLT LLKALVRQQLPEKYKEIFFDQSKNGYAGYIDGGASQEEFYKFIKPILEKM DGTEELLVKLNREDLLRKQRTFDNGSIPHQIHLGELHAILRRQEDFYPFL KDNREKIEKILTFRIPYYVGPLARGNSRFAWMTRKSEETITPWNFEEVV |

| SEQ ID NO: | Description | Sequences |
|---|---|---|
| | | DKGASAQSFIERMTNFDKNLPNEKVLPKHSLLYEYFTVYNELTKVKYVT<br>EGMRKPAFLSGEQKKAIVDLLFKTNRKVTVKQLKEDYFKKIECFDSVEIS<br>GVEDRFNASLGTYHDLLKIIKDKDFLDNEENEDILEDIVLTLTLFEDREMI<br>EERLKTYAHLFDDKVMKQLKRRRYTGWGRLSRKLINGIRDKQSGKTIL<br>DFLKSDGFANRNFMQLIHDDSLTFKEDIQKAQVSGQGDSLHEHIANL<br>AGSPAIKKGILQTVKVVDELVKVMGRHKPENIVIEMARENQTTQKGQ<br>KNSRERMKRIEEGIKELGSQILKEHPVENTQLQNEKLYLYYLQNGRDM<br>YVDQELDINRLSDYDVDAIVPQSFLKDDSIDNKVLTRSDKNRGKSDNV<br>PSEEVVKKMKNYWRQLLNAKLITQRKFDNLTKAERGGLSELDKAGFIK<br>RQLVETRQITKHVAQILDSRMNTKYDENDKLIREVKVITLKSKLVSDFRK<br>DFQFYKVREINNYHHAHDAYLNAVVGTALIKKYPKLESEFVYGDYKVYD<br>VRKMIAKSEQEIGKATAKYFFYSNIMNFFKTEITLANGEIRKRPLIETNG<br>ETGEIVWDKGRDFATVRKVLSMPQVNIVKKTEVQTGGFSKESILPKRN<br>SDKLIARKKDWDPKKYGGFDSPTVAYSVLVVAKVEKGKSKKLKSVKELL<br>GITIMERSSFEKNPIDFLEAKGYKEVKKDLIIKLPKYSLFELENGRKRMLA<br>SAGELQKGNELALPSKYVNFLYLASHYEKLKGSPEDNEQKQLFVEQHK<br>HYLDEIIEQISEFSKRVILADANLDKVLSAYNKHRDKPIREQAENIIHLFTL<br>TNLGAPAAFKYFDTTIDRKRYTSTKEVLDATLIHQSITGLYETRIDLSQLG<br>GDSGGSPKKKRKV |
| 52 | ErTadA1.0-Cas9(D10A) (AA) | MSDTQIDEKWMRHALTLARRAREEGEVPVGAVLVLGDTVIGEGWNR<br>AIGLHDPTAHAEIMALRQGGKVLENYRLLDTTLYVTFEPCVMCAGAM<br>VHGRVGRLVFGVRNSKRGAAGSLLNILNYAGMNHQVSVEQGVLAAE<br>CAAMLCNFYRQPRAVFNALRDRLRAELLKINSGGSSGGSSGSETPGTS<br>ESATPESSGGSSGGSDKKYSIGLAIGTNSVGWAVITDEYKVPSKKFKVL<br>GNTDRHSIKKNLIGALLFDSGETAEATRLKRTARRRYTRRKNRICYLQEI<br>FSNEMAKVDDSFFHRLEESFLVEEDKKHERHPIFGNIVDEVAYHEKYPT<br>IYHLRKKLVDSTDKADLRLIYLALAHMIKFRGHFLIEGDLNPDNSDVDKL<br>FIQLVQTYNQLFEENPINASGVDAKAILSARLSKSRRLENLIAQLPGEKK<br>NGLFGNLIALSLGLTPNFKSNFDLAEDAKLQLSKDTYDDDLDNLLAQIG<br>DQYADLFLAAKNLSDAILLSDILRVNTEITKAPLSASMIKRYDEHHQDLT<br>LLKALVRQQLPEKYKEIFFDQSKNGYAGYIDGGASQEEFYKFIKPILEKM<br>DGTEELLVKLNREDLLRKQRTFDNGSIPHQIHLGELHAILRRQEDFYPFL<br>KDNREKIEKILTFRIPYYVGPLARGNSRFAWMTRKSEETITPWNFEEVV<br>DKGASAQSFIERMTNFDKNLPNEKVLPKHSLLYEYFTVYNELTKVKYVT<br>EGMRKPAFLSGEQKKAIVDLLFKTNRKVTVKQLKEDYFKKIECFDSVEIS<br>GVEDRFNASLGTYHDLLKIIKDKDFLDNEENEDILEDIVLTLTLFEDREMI<br>EERLKTYAHLFDDKVMKQLKRRRYTGWGRLSRKLINGIRDKQSGKTIL<br>DFLKSDGFANRNFMQLIHDDSLTFKEDIQKAQVSGQGDSLHEHIANL<br>AGSPAIKKGILQTVKVVDELVKVMGRHKPENIVIEMARENQTTQKGQ<br>KNSRERMKRIEEGIKELGSQILKEHPVENTQLQNEKLYLYYLQNGRDM<br>YVDQELDINRLSDYDVDHIVPQSFLKDDSIDNKVLTRSDKNRGKSDNV<br>PSEEVVKKMKNYWRQLLNAKLITQRKFDNLTKAERGGLSELDKAGFIK<br>RQLVETRQITKHVAQILDSRMNTKYDENDKLIREVKVITLKSKLVSDFRK<br>DFQFYKVREINNYHHAHDAYLNAVVGTALIKKYPKLESEFVYGDYKVYD<br>VRKMIAKSEQEIGKATAKYFFYSNIMNFFKTEITLANGEIRKRPLIETNG<br>ETGEIVWDKGRDFATVRKVLSMPQVNIVKKTEVQTGGFSKESILPKRN<br>SDKLIARKKDWDPKKYGGFDSPTVAYSVLVVAKVEKGKSKKLKSVKELL<br>GITIMERSSFEKNPIDFLEAKGYKEVKKDLIIKLPKYSLFELENGRKRMLA<br>SAGELQKGNELALPSKYVNFLYLASHYEKLKGSPEDNEQKQLFVEQHK<br>HYLDEIIEQISEFSKRVILADANLDKVLSAYNKHRDKPIREQAENIIHLFTL<br>TNLGAPAAFKYFDTTIDRKRYTSTKEVLDATLIHQSITGLYETRIDLSQLG<br>GD |
| 53 | SV40 NLS-ErTadA1.0-linker-Cas9(D10A)-SV40 NLS (AA) | PKKKRKVMSDTQIDEKWMRHALTLARRAREEGEVPVGAVLVLGDTVI<br>GEGWNRAIGLHDPTAHAEIMALRQGGKVLENYRLLDTTLYVTFEPCV<br>MCAGAMVHGRVGRLVFGVRNSKRGAAGSLLNILNYAGMNHQVSVE<br>QGVLAAECAAMLCNFYRQPRAVFNALRDRLRAELLKINSGSGTETPGTSE<br>SATPESDKKYSIGLAIGTNSVGWAVITDEYKVPSKKFKVLGNTDRHSIKK<br>NLIGALLFDSGETAEATRLKRTARRRYTRRKNRICYLQEIFSNEMAKVD<br>DSFFHRLEESFLVEEDKKHERHPIFGNIVDEVAYHEKYPTIYHLRKKLVDS<br>TDKADLRLIYLALAHMIKFRGHFLIEGDLNPDNSDVDKLFIQLVQTYNQ<br>LFEENPINASGVDAKAILSARLSKSRRLENLIAQLPGEKKNGLFGNLIAL<br>SLGLTPNFKSNFDLAEDAKLQLSKDTYDDDLDNLLAQIGDQYADLFLAA<br>KNLSDAILLSDILRVNTEITKAPLSASMIKRYDEHHQDLTLLKALVRQQL<br>PEKYKEIFFDQSKNGYAGYIDGGASQEEFYKFIKPILEKMDGTEELLVKL<br>NREDLLRKQRTFDNGSIPHQIHLGELHAILRRQEDFYPFLKDNREKIEKI<br>LTFRIPYYVGPLARGNSRFAWMTRKSEETITPWNFEEVVDKGASAQSF<br>IERMTNFDKNLPNEKVLPKHSLLYEYFTVYNELTKVKYVTEGMRKPAFL<br>SGEQKKAIVDLLFKTNRKVTVKQLKEDYFKKIECFDSVEISGVEDRFNAS<br>LGTYHDLLKIIKDKDFLDNEENEDILEDIVLTLTLFEDREMIEERLKTYAHL<br>FDDKVMKQLKRRRYTGWGRLSRKLINGIRDKQSGKTILDFLKSDGFAN<br>RNFMQLIHDDSLTFKEDIQKAQVSGQGDSLHEHIANLAGSPAIKKGIL<br>QTVKVVDELVKVMGRHKPENIVIEMARENQTTQKGQKNSRERMKRI |

| SEQ ID NO: | Description | Sequences |
|---|---|---|
| | | EEGIKELGSQILKEHPVENTQLQNEKLYLYYLQNGRDMYVDQELDINRL<br>SDYDVDHIVPQSFLKDDSIDNKVLTRSDKNRGKSDNVPSEEVVKKMK<br>NYWRQLLNAKLITQRKFDNLTKAERGGLSELDKAGFIKRQLVETRQITK<br>HVAQILDSRMNTKYDENDKLIREVKVITLKSKLVSDFRKDFQFYKVREI<br>NNYHHAHDAYLNAVVGTALIKKYPKLESEFVYGDYKVYDVRKMIAKSE<br>QEIGKATAKYFFYSNIMNFFKTEITLANGEIRKRPLIETNGETGEIVWDK<br>GRDFATVRKVLSMPQVNIVKKTEVQTGGFSKESILPKRNSDKLIARKKD<br>WDPKKYGGFDSPTVAYSVLVVAKVEKGKSKKLKSVKELLGITIMERSSFE<br>KNPIDFLEAKGYKEVKKDLIIKLPKYSLFELENGRKRMLASAGELQKGNE<br>LALPSKYVNFLYLASHYEKLKGSPEDNEQKQLFVEQHKHYLDEIIEQISE<br>FSKRVILADANLDKVLSAYNKHRDKPIREQAENIIHLFTLTNLGAPAAFK<br>YFDTTIDRKRYTSTKEVLDATLIHQSITGLYETRIDLSQLGGDPKKKRKV |
| 54 | SV40 NLS-<br>ErTadA1.0-linker-<br>Cas9(D10A &<br>H840A)-linker-<br>SV40 NLS (AA) | PKKKRKVMSDTQIDEKWMRHALTLARRAREEGEVPVGAVLVLGDTVI<br>GEGWNRAIGLHDPTAHAEIMALRQGGKVLENYRLLDTTLYVTFEPCV<br>MCAGAMVHGRVGRLVFGVRNSKRGAAGSLLNILNYAGMNHQVSVE<br>QGVLAAECAAMLCNFYRQPRAVFNALRDRLRAELLKINSGGSSGGSS<br>GSETPGTSESATPESSGGSSGGSDKKYSIGLAIGTNSVGWAVITDEYKV<br>PSKKFKVLGNTDRHSIKKNLIGALLFDSGETAEATRLKRTARRRYTRRKN<br>RICYLQEIFSNEMAKVDDSFFHRLEESFLVEEDKKHERHPIFGNIVDEVA<br>YHEKYPTIYHLRKKLVDSTDKADLRLIYLALAHMIKFRGHFLIEGDLNPD<br>NSDVDKLFIQLVQTYNQLFEENPINASGVDAKAILSARLSKSRRLENLIA<br>QLPGEKKNGLFGNLIALSLGLTPNFKSNFDLAEDAKLQLSKDTYDDDLD<br>NLLAQIGDQYADLFLAAKNLSDAILLSDILRVNTEITKAPLSASMIKRYD<br>EHHQDLTLLKALVRQQLPEKYKEIFFDQSKNGYAGYIDGGASQEEFYKF<br>IKPILEKMDGTEELLVKLNREDLLRKQRTFDNGSIPHQIHLGELHAILRR<br>QEDFYPFLKDNREKIEKILTFRIPYYVGPLARGNSRFAWMTRKSEETITP<br>WNFEEVVDKGASAQSFIERMTNFDKNLPNEKVLPKHSLLYEYFTVYNE<br>LTKVKYVTEGMRKPAFLSGEQKKAIVDLLFKTNRKVTVKQLKEDYFKKI<br>ECFDSVEISGVEDRFNASLGTYHDLLKIIKDKDFLDNEENEDILEDIVLTL<br>TLFEDREMIEERLKTYAHLFDDKVMKQLKRRRYTGWGRLSRKLINGIR<br>DKQSGKTILDFLKSDGFANRNFMQLIHDDSLTFKEDIQKAQVSGQGDS<br>LHEHIANLAGSPAIKKGILQTVKVVDELVKVMGRHKPENIVIEMAREN<br>QTTQKGQKNSRERMKRIEEGIKELGSQILKEHPVENTQLQNEKLYLYYL<br>QNGRDMYVDQELDINRLSDYDVDAIVPQSFLKDDSIDNKVLTRSDKN<br>RGKSDNVPSEEVVKKMKNYWRQLLNAKLITQRKFDNLTKAERGGLSE<br>LDKAGFIKRQLVETRQITKHVAQILDSRMNTKYDENDKLIREVKVITLKS<br>KLVSDFRKDFQFYKVREINNYHHAHDAYLNAVVGTALIKKYPKLESEFV<br>YGDYKVYDVRKMIAKSEQEIGKATAKYFFYSNIMNFFKTEITLANGEIRK<br>RPLIETNGETGEIVWDKGRDFATVRKVLSMPQVNIVKKTEVQTGGFSK<br>ESILPKRNSDKLIARKKDWDPKKYGGFDSPTVAYSVLVVAKVEKGKSKK<br>LKSVKELLGITIMERSSFEKNPIDFLEAKGYKEVKKDLIIKLPKYSLFELEN<br>GRKRMLASAGELQKGNELALPSKYVNFLYLASHYEKLKGSPEDNEQKQ<br>LFVEQHKHYLDEIIEQISEFSKRVILADANLDKVLSAYNKHRDKPIREQA<br>ENIIHLFTLTNLGAPAAFKYFDTTIDRKRYTSTKEVLDATLIHQSITGLYET<br>RIDLSQLGGDSGGSPKKKRKV |

EXAMPLES

Figure 16A:
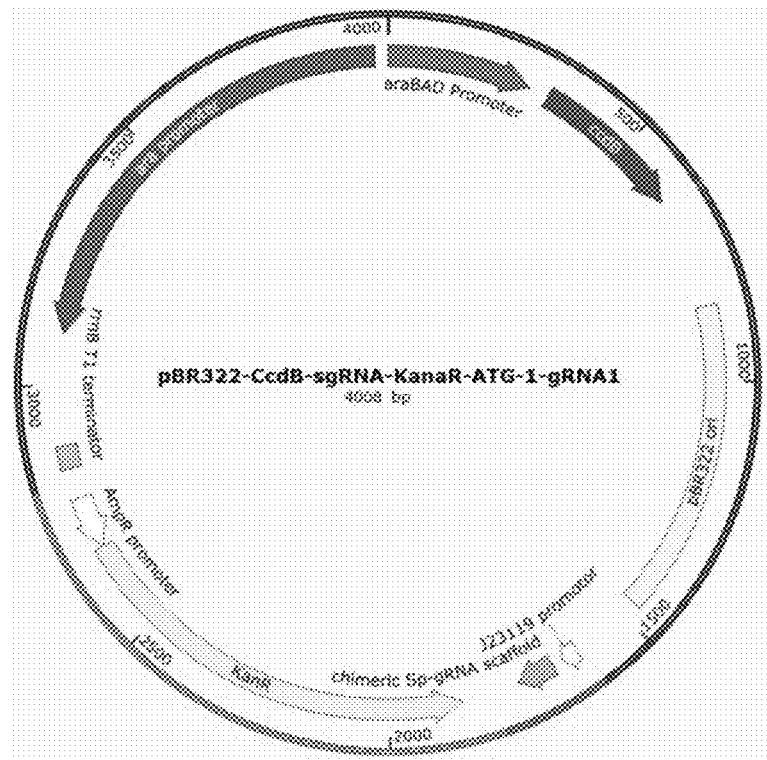
FIG. 16A-FIG. 16D, FIG. 17A-FIG. 17D, FIG. 18, FIG. 19A-FIG. 19B, FIG. 20A-FIG. 20C, FIG. 21A-FIG. 21B, and FIG. 22A-FIG. 22B are schematic structures showing the various adenosine base editors constructed according to the examples of the present invention, where amino acid sequence SGGSSGGS is SEQ ID NO: 11.
Figure 16B:
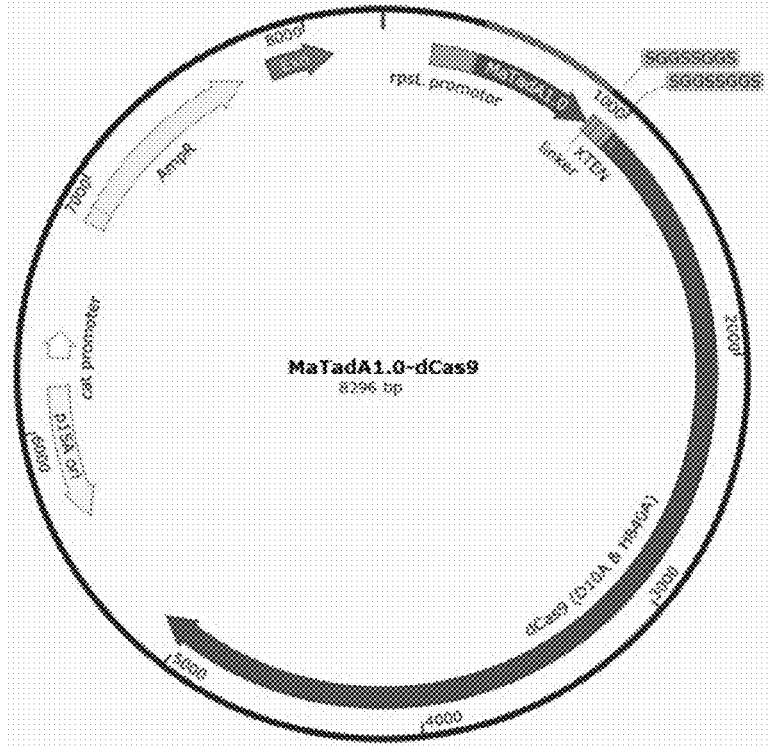
Figure 16C:
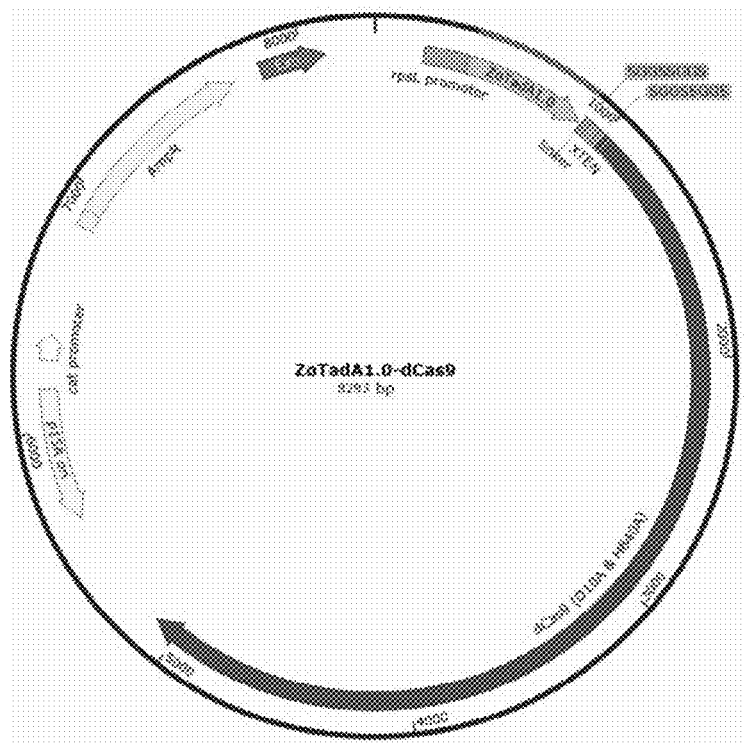
Figure 16D:
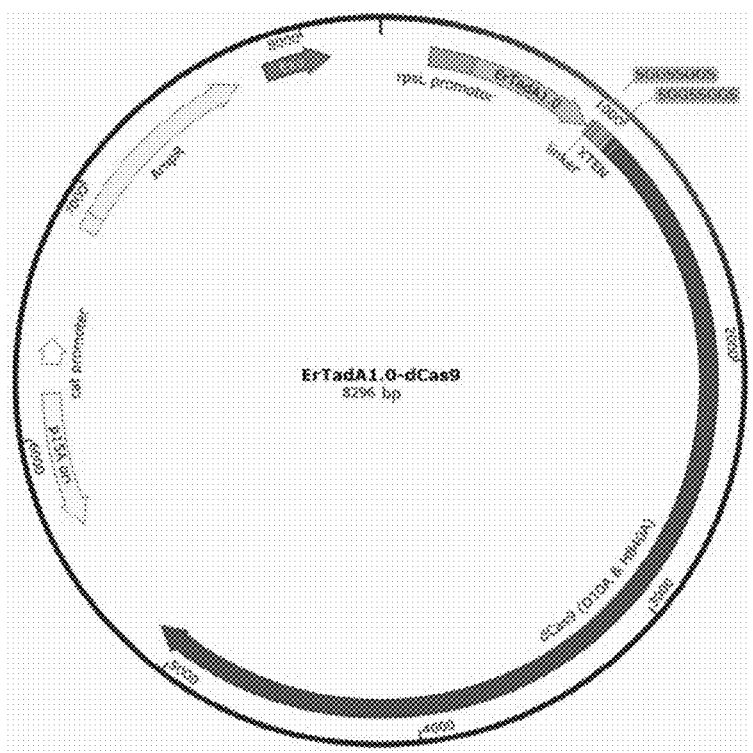

Example 1. Verification of Deamination Effects of the Adenosine Deaminases in Prokaryotic Cells Using Initiation Condon of Gene ccdB 1.1 Construction of Various Base Editor Plasmids in Experimental and Control Groups Two types of base editor plasmids in experimental group were constructed. Plasmid type A: sgRNA-ccdB1, targeting the initiation codon of the antisense strand of ccdB gene and having a sequence of 5'-CTGCATTTATGTCAGACTTG-3' (SEQ ID NO: 42) was constructed with a promoter into a commercial plasmid containing ccdB gene driven by an arabinose-inducible promoter. The plasmid A was labelled as pBR322-ccdB-sgRNA-KanaR-ATG-1-gRNA1 (FIG. 16A). The other type of plasmid (type B) was constructed by incorporating the adenosine deaminases (MaTadA1.0, ZoTadA1.0, ErTadA1.0) linked to dCas9 via a linker into a commercial plasmid. The plasmids were labelled as MaTadA1.0-dCas9, ZoTadA1.0-dCas9 and ErTadA1.0-dCas9, respectively (FIG. 16B-FIG. 16D).

Figure 17A:
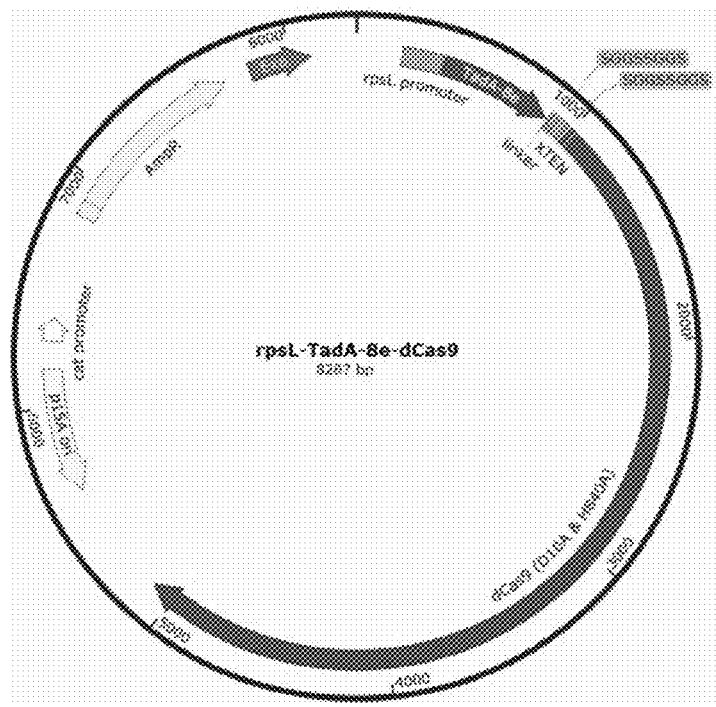
Figure 17B:
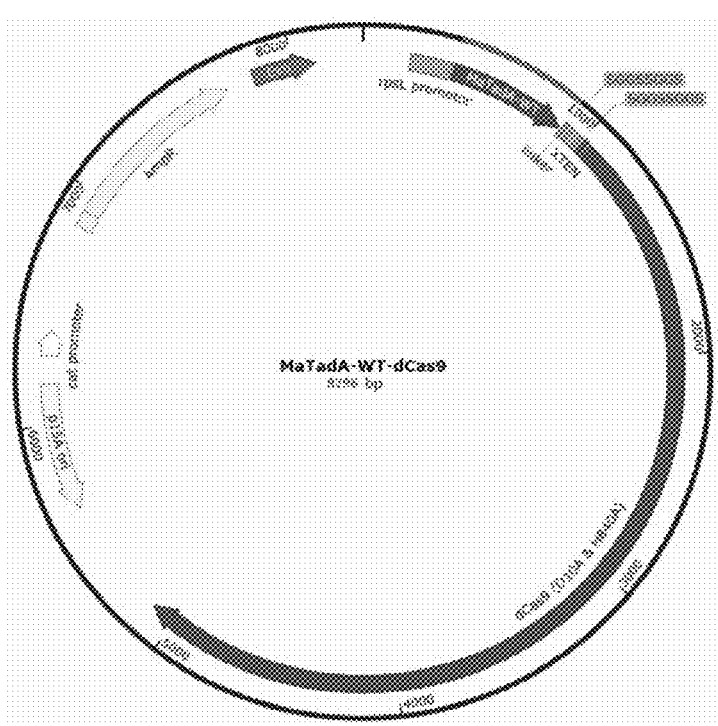
Figure 17C:
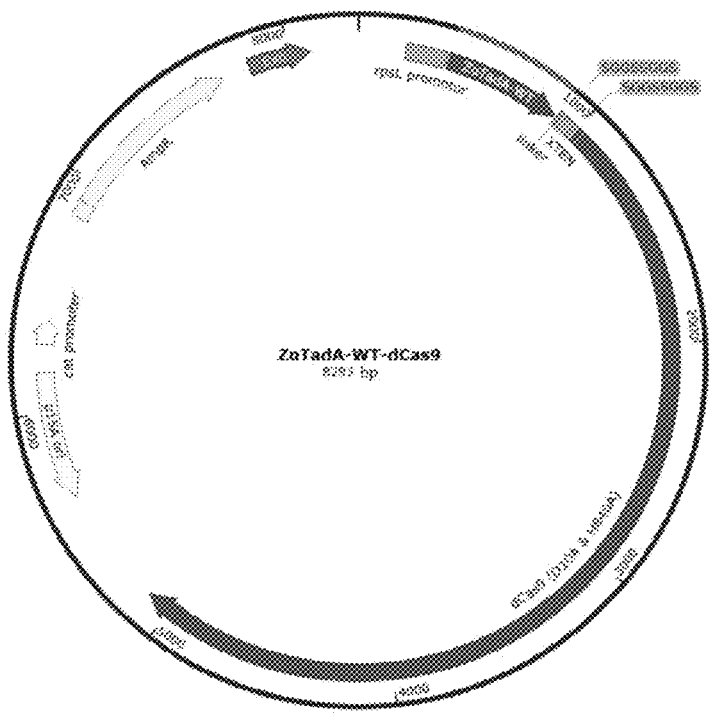
Figure 17D:
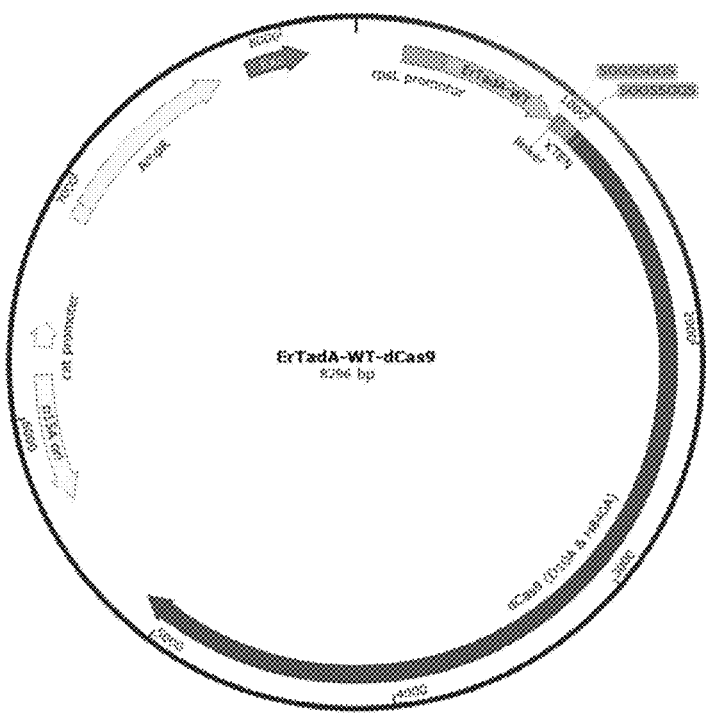

Two types of base editor plasmids in control group were constructed. Plasmid type C: the adenosine deaminases TadA-8e linked to dCas9 via a linker was constructed into a commercial plasmid and labelled as TadA-8e-dCas9 (FIG. 17A). The other type of plasmid (type D) was constructed by incorporating the wild-type adenosine deaminases (MaTadA-WT, ZoTadA-WT or ErTadA-WT) linked to dCas9 via a linker into a commercial plasmid. The plasmids were labelled as MaTadA-WT-dCas9, ZoTadA-WT-dCas9 and ErTadA-WT-dCas9, respectively (FIG. 17B-FIG. 17D) and used as negative controls.

1.2 Verification of the Deaminase Activity of the Base Editors in Prokaryotic Cells Principle of the verification using ccdB gene: the expression of ccdB toxic gene is regulated by the AraBAD Operon. The expression of ccdB is inhibited when culture environment contains a large amount of glucose (final concentration of 100 mM), while ccdB is induced to express when arabinose is contained in the culture environment and the higher the concentration of arabinose is, the higher the expression amount would be. After ccdB is induced to express, it will interact with DNA helicase and destroy the structure of double stranded host DNA. If the adenosine deaminases (MaTadA1.0, ZoTadA1.0, ErTadA1.0) have deamination activities, the initiation codon of the antisense strand of ccdB gene would be edited from TAC to TGC upon binding of dCas9 to the initiation codon area under the guide of the sgRNA, resulting in the editing of the initiation codon in the sense strand of ccdB gene from ATG to ACG, ultimately causing frameshift mutation in ccdB gene and incapability of correctly expressing ccdB protein. In this situation, the host DNA will not be disrupted by the expression product of the recombinant plasmid and the host bacteria will survive and replicate normally. If, however, the adenosine deaminases (MaTadA1.0, ZoTadA1.0, ErTadA1.0) do not have deamination activities, the base editors will not work and ccdB protein will be correctly expressed, leading to interaction with DNA helicase and destroying the structure of the host DNA. In this latter situation, the host bacteria will be killed. Therefore, the deamination activity of the base editors can be verified through the growth of the E. coli.

The plasmid pBR322-ccdB-sgRNA-KanaR-ATG-1-gRNA1 was transformed into competent E. coli cells to obtain stable competent cells. Plasmids MaTadA1.0-dCas9, ZoTadA1.0-dCas9, ErTadA1.0-dCas9, TadA-8e-dCas9, MaTadA-WT-dCas9, ZoTadA-WT-dCas9 or ErTadA-WT-dCas9 were then transformed into the stable competent cells. The E. coli cells were coated on LB solid media containing an antibiotic (kanamycin) and supplemented with 100 nM glucose and various concentrations of arabinose (0 nM, 20 nM and 40 nM), incubated overnight at 37° C. The growth of E. coli cells was observed and provided in FIG. 1A-FIG. 1D, and FIG. 3A-FIG. 3C.

The results showed that the adenosine deaminases (MaTadA1.0, ZoTadA1.0, ErTadA1.0) provided by the present invention and TadA-8e have editing effects on the initiation codon of ccdB gene. E. coli cells normally grew in all groups supplemented with glucose but no arabinose. In dCas9 control, MaTadA-WT-dCas9, ZoTadA-WT-dCas9, and ErTadA-WT-dCas9 groups, E. coli cells did not grow when supplemented with glucose and different concentrations of arabinoses, indicating the base editors did not work and arabinose-induced ccdB protein expression was normally occurred, which resulted in death of E. coli cells. However, in TadA-8e-dCas9, MaTadA1.0-dCas9, ZoTadA1.0-dCas9, and ErTadA1.0-dCas9 groups, E. coli cells grew when supplemented with glucose and different concentrations of arabinoses, indicating the adenosine deaminases of the base editors have deamination activity and results in frameshift mutation in the ccdB gene, such that the ccdB gene could not be correctly expressed and the E. coli cells survived.

Example 2. Function Verification of Other Adenosine Deaminases in Prokaryotic Cells The base editing effects on the initiation codon region in a prokaryotic cell of the adenosine base editors constructed with adenosine deaminases MaTadA1.0-1, MaTadA1.0-2, MaTadA1.0-3, ZoTadA1.0-1, ZoTadA1.0-2, ZoTadA1.0-3, ErTadA1.0-1, ErTadA1.0-2 and ErTadA1.0-3, respectively, and dCas9 were verified using the methods described in Example 1, and the results were shown in FIG. 5A-FIG. 5C.

Figure 18:
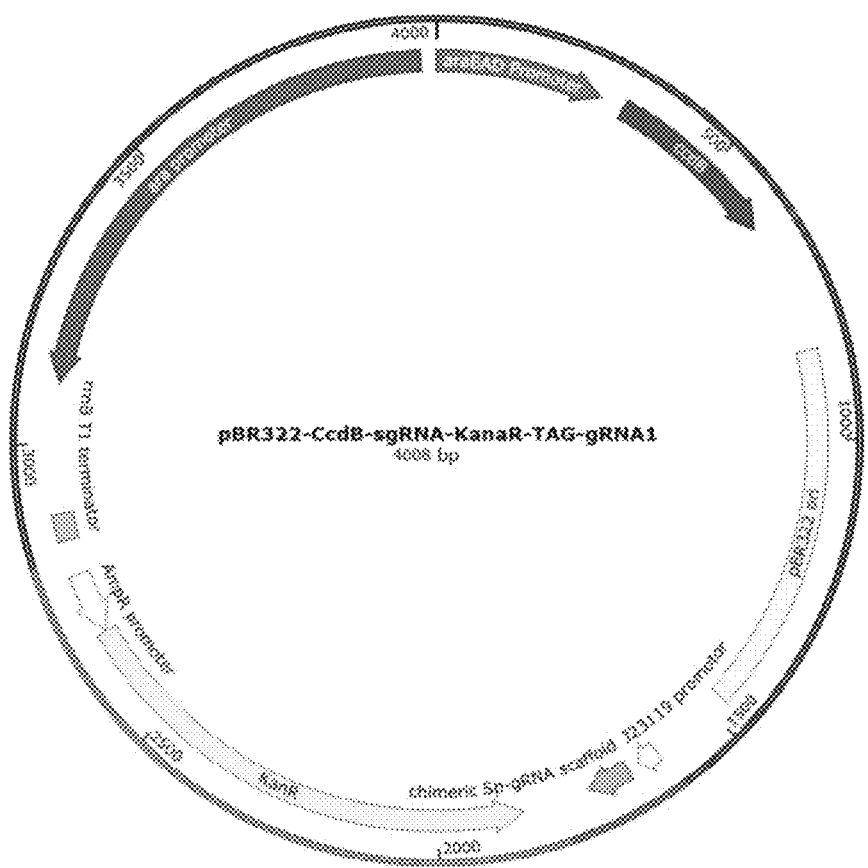

Example 3. Comparison of Editing Efficiencies of the Adenosine Deaminases MaTadA1.0 and TadA-8e on the Stop Codon of ccdB Gene in Prokaryotic Cells 3.1 Construction of Various Base Editor Plasmids in Experimental and Control Groups Two types of base editor plasmids in experimental group were constructed. Plasmid type E: sgRNA-ccdB2, targeting the stop codon of the antisense strand of ccdB gene and having a sequence of 5'-atatagctaagatgtcacgg-3' (SEQ ID NO: 43) was constructed with a promoter into a commercial plasmid containing ccdB gene driven by an arabinose-inducible promoter. The plasmid E was labelled as pBR322-CcdB-sgRNA-KanaR-TAG-gRNA1 (FIG. 18). The other type of plasmid was the plasmid MaTadA1.0-dCas9 constructed according to step 1.1 in Example 1 (FIG. 16A-FIG. 16D).

The base editor plasmid in control group was TadA-8e-dCas9 as constructed according to step 1.1 in Example 1 (FIG. 17A-FIG. 17D).

3.2 Verification of the Deaminase Activity of the Base Editors in Prokaryotic Cells on Adenosine a in ccdB Stop Codon.

Principle of the verification using ccdB gene: the main active domain of ccdB protein is located at the terminal amino acids WGI. The adenosine deaminase MaTadA1.0 was proven to have deamination activity in the above, the stop codon of the antisense strand of ccdB gene would be edited from ATC to GTC upon binding of dCas9 to the stop codon area under the guide of the sgRNA, resulting in the editing of the initiation codon in the sense strand of ccdB gene from TAG to CAG, ultimately causing frameshift mutation in ccdB gene and incapability of correctly expressing ccdB protein. In this situation, the host DNA will not be disrupted by the expression product of the recombinant plasmid and the host bacteria will survive and replicate normally. The deamination activity of the base editors can be verified through the growth of the E. coli cells.

The plasmid pBR322-CcdB-sgRNA-KanaR-TAG-gRNA1 was transformed into competent E. coli cells to obtain stable competent cells. Plasmids MaTadA1.0-dCas9 and TadA-8e-dCas9 were then transformed into the stable competent cells. The E. coli cells were coated on LB solid media containing an antibiotic (kanamycin) and supplemented with 100 nM glucose and various concentrations of arabinose (0 nM, 20 nM and 40 nM), incubated overnight at 37° C. The growth of E. coli cells was observed and provided in FIG. 2 and FIG. 4.

E. coli cells normally grew in all groups supplemented with glucose but no arabinose. In dCas9 control and MaTadA-WT-dCas9 groups, E. coli cells did not grow when supplemented with glucose and different concentrations of arabinoses, indicating the base editors did not work and arabinose-induced ccdB protein expression was normally occurred, which resulted in death of E. coli cells. However, in TadA-8e-dCas9 and MaTadA1.0-dCas9 groups, E. coli cells grew when supplemented with glucose and different concentrations of arabinoses, indicating the adenosine deaminases of the base editors have deamination activity and results in frameshift mutation in the ccdB gene, such that the ccdB gene could not be correctly expressed and the E. coli cells survived. The results showed that both MaTadA1.0 and TadA-8e have editing effects on ccdB gene stop codon, slightly weaker than the effects on the initiation codon though.

Example 4. Function Verification of Adenosine Deaminases MaTadA1.1, MaTadA1.2, MaTadA1.3, MaTadA1.4 and MaTadA1.5 in Prokaryotic Cells The base editing effects on the initiation codon region in a prokaryotic cell of the adenosine base editors constructed with adenosine deaminases MaTadA1.1, MaTadA1.2, MaTadA1.3, MaTadA1.4 and MaTadA1.5, respectively, and dCas9 were verified using the methods described in Example 1, and the results were shown in FIG. 1A-FIG. 1B, and FIG. 3A-FIG. 3C. From FIG. 3A-FIG. 3C, it was shown that all the adenosine deaminases had editing effects with the adenosine deaminase MaTadA1.1 had the best effects, superior to adenosine deaminases MaTadA1.2, MaTadA1.3 and MaTadA1.5, which are in turn superior to adenosine deaminase MaTadA1.4.

Figure 19A:
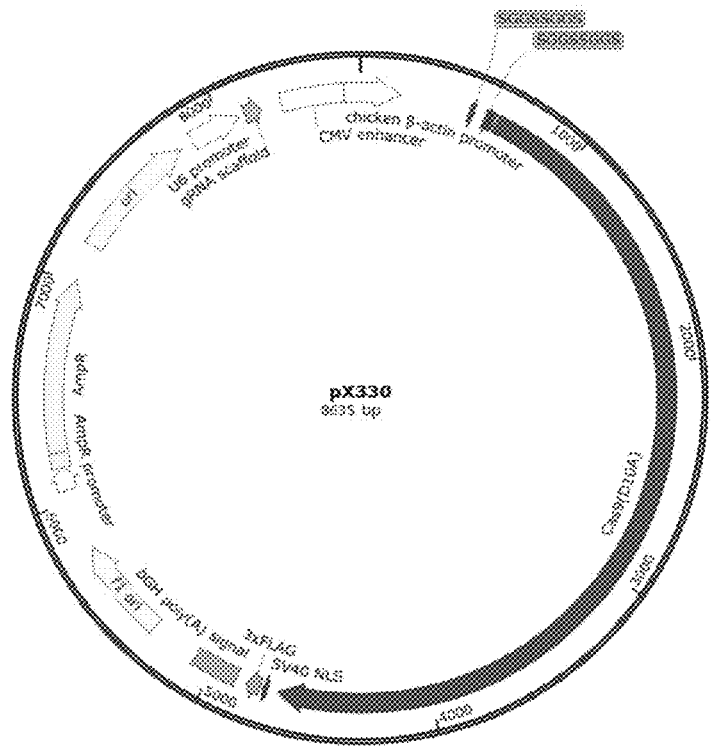
Figure 19B:
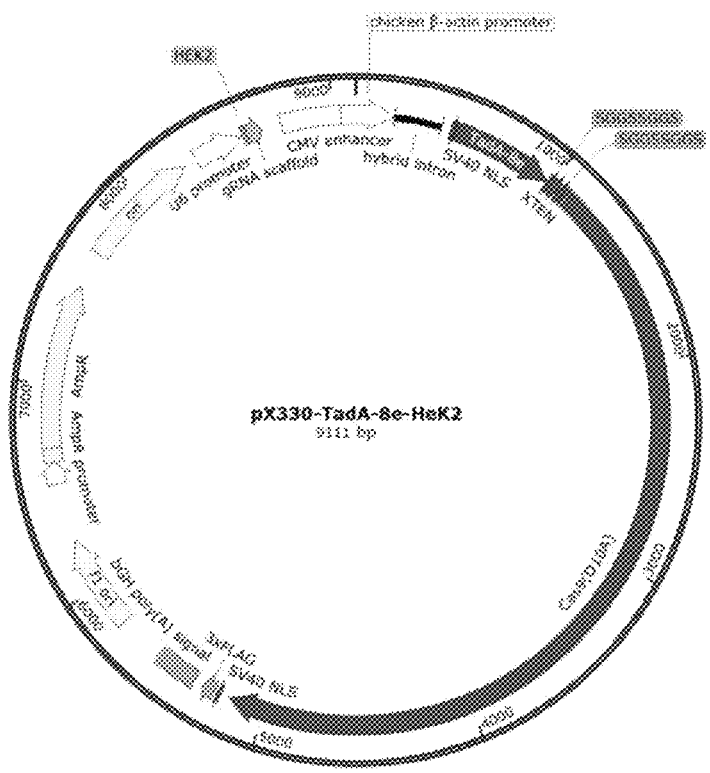
Figure 20A:
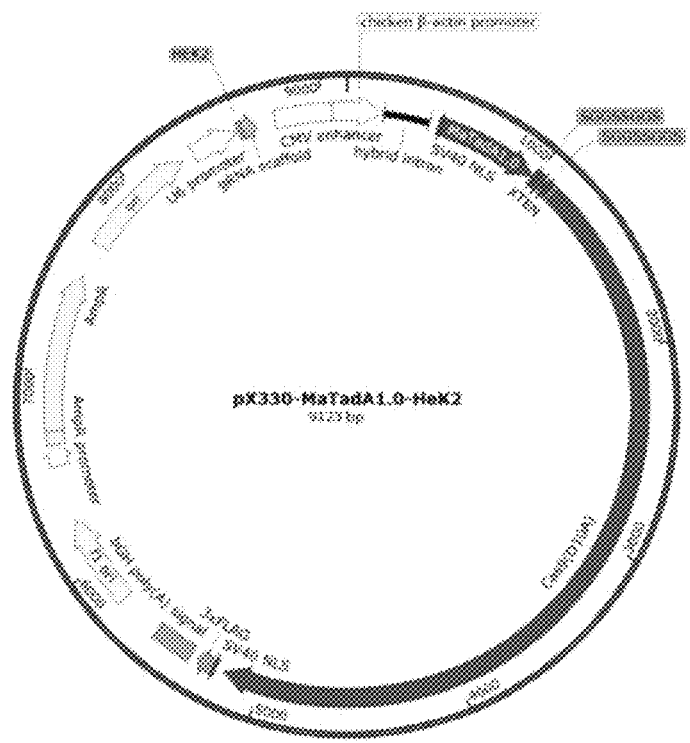
Figure 20B:
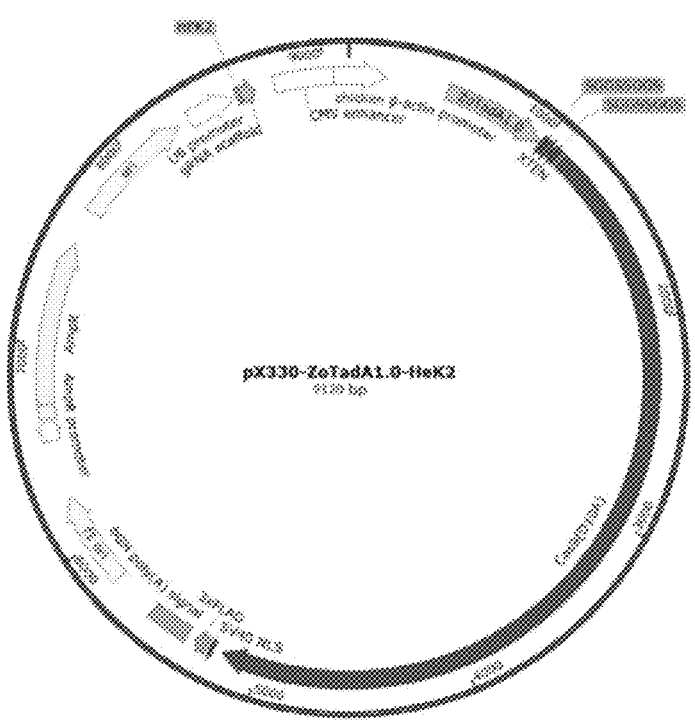
Figure 20C:
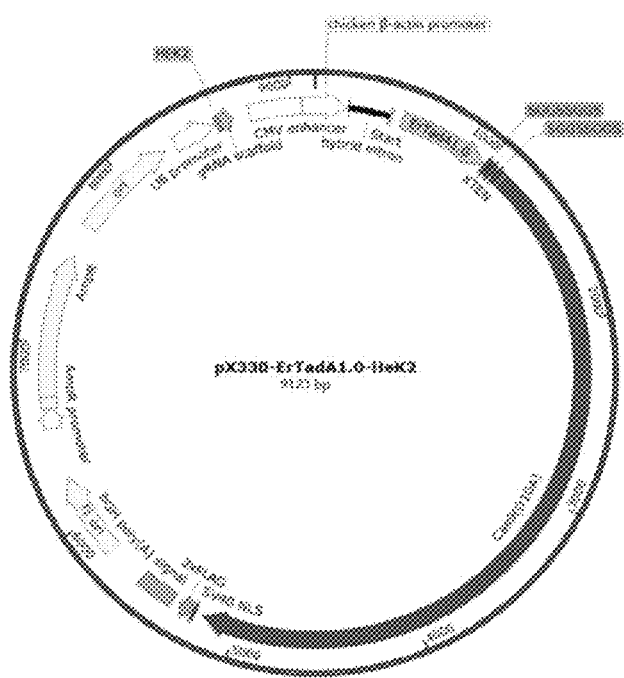
Figure 21A:
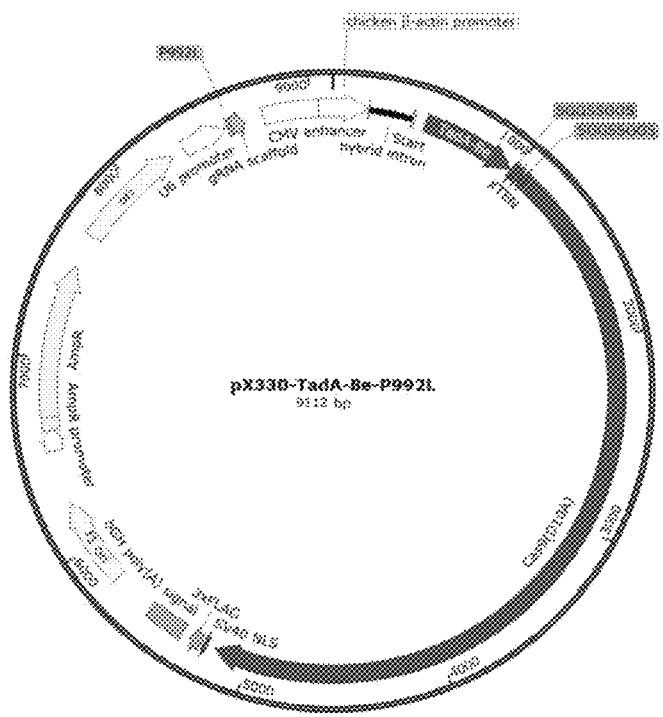
Figure 21B:
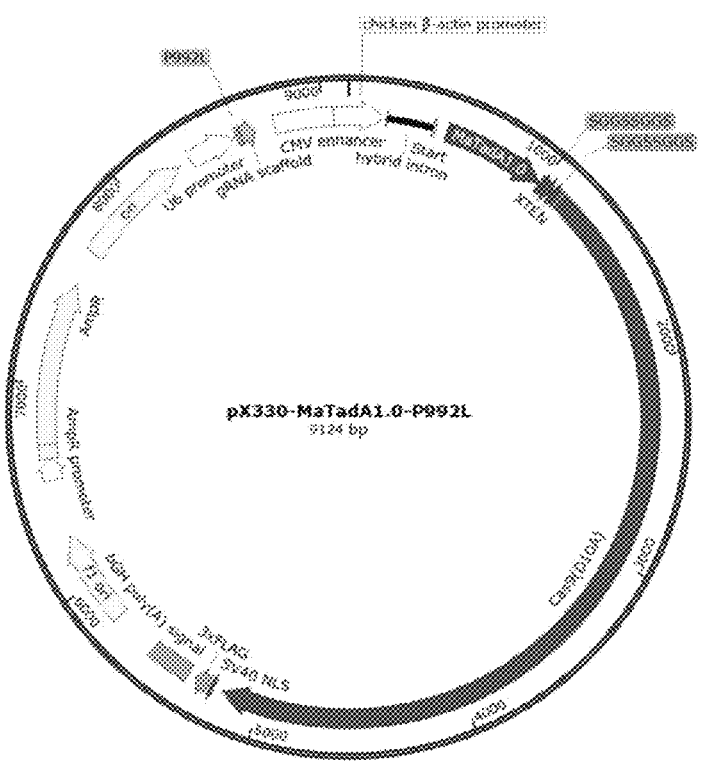
Figure 22A:
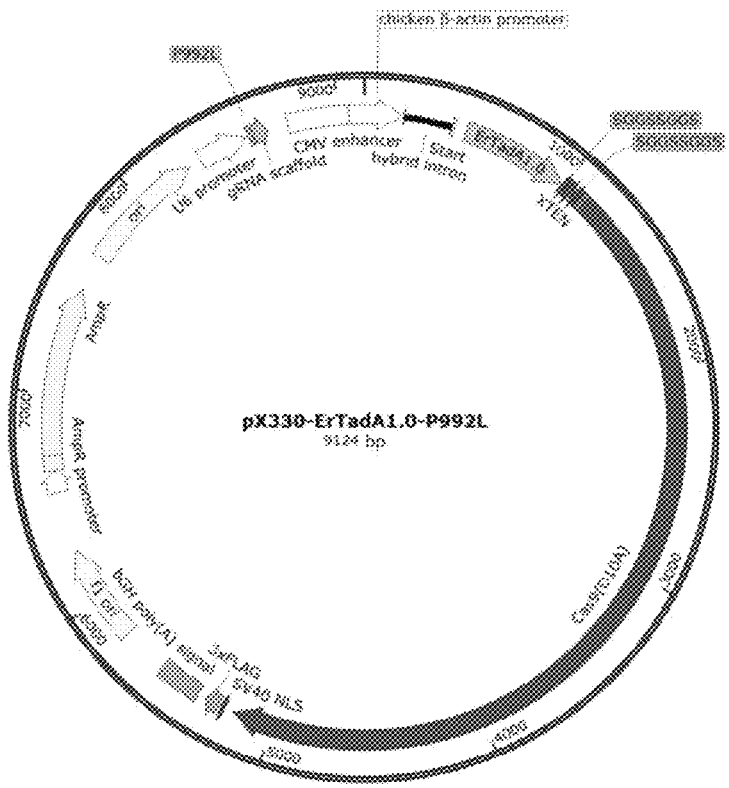
Figure 22B:
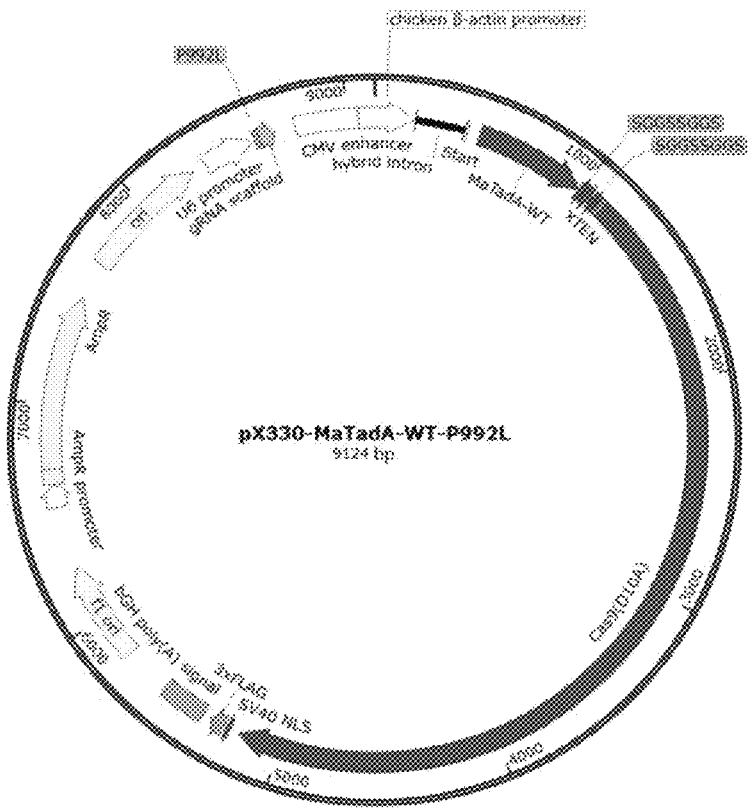

Example 5. Verification of the Deaminase Activity of the Adenosine Deaminases in 293T Human Cells The adenosine deaminases MaTadA 1.0, ZoTadA1.0, ErTadA 1.0, TadA-8e and MaTadA-WT were constructed, respectively, into a eukaryotic expression vector comprising chicken β-actin promoter and nCas9 gene, and sgRNA sequence driven by a U6 promoter, to form recombinant adenosine base editor vectors, labelled as pX330-MaTadA1.0-HeK2 (FIG. 20A), pX330-ZoTadA1.0-HeK2 (FIG. 20B), pX330-ErTadA1.0-HeK2 (FIG. 20C), pX330-TadA-8e-HeK2 (FIG. 19B), pX330-MaTadA1.0-P992L (FIG. 21B), pX330-ErTadA1.0-P992L (FIG. 22A), pX330-TadA-8e-P992L (FIG. 21A), and pX330-MaTadA-WT-P992L (FIG. 22B), respectively. The sgRNA included two segments, i.e., the targeting segment (also known as spacer sequence in the context of endogenous CRISPR system) and the protein binding segment which contained direct repeat sequences. The targeting segment of the sgRNA acts on target gene Hek-2 and ATP3B gene P992L site. A blank control plasmid that did not containing adenosine deaminase but containing sgRNA with only protein binding segment scaffold and on targeting segment, was also constructed and labelled as px330 (FIG. 19A). sgRNA targeting Hek-2 was 5'-gaacacaaagcatagactgc-3' (SEQ ID NO: 44). sgRNA targeting p992L was 5'-gcgtgagegtggccagcccca-3' (SEQ ID NO: 45).

The adenine base editor vectors were then transfected into human cells by liposome transfection and cultured at 37° C. and 5% carbon dioxide concentration for 72h. DNA was extracted from all cells, and the sequences containing the target site were amplified. The PCR products were sequenced, and the sequencing results were compared with the corresponding genes of the human genome. The editing efficiencies of the adenine base editors were determined for the target gene. The results showed that the editing efficiencies of the adenine base editor vectors provided by the present invention for Hek-2 site and ATP7B gene P992L site could reach more than 50%, and part of the original sequencing data were shown in FIGS. 6-15.

FIG. 6 shows the sequencing results after HEK2 gene editing by pX330-MaTadA1.0-HeK2 in 293T cells. Results show editing effects, and the editing window was position 3, 5, and 7. The data in the lower table showed the values at each nucleotide site, with the value below 10 treated as noise. The A→G editing efficiency was about 13% at position 3, about 54% at position 5, and about 53% at position 7.

Figure 7:
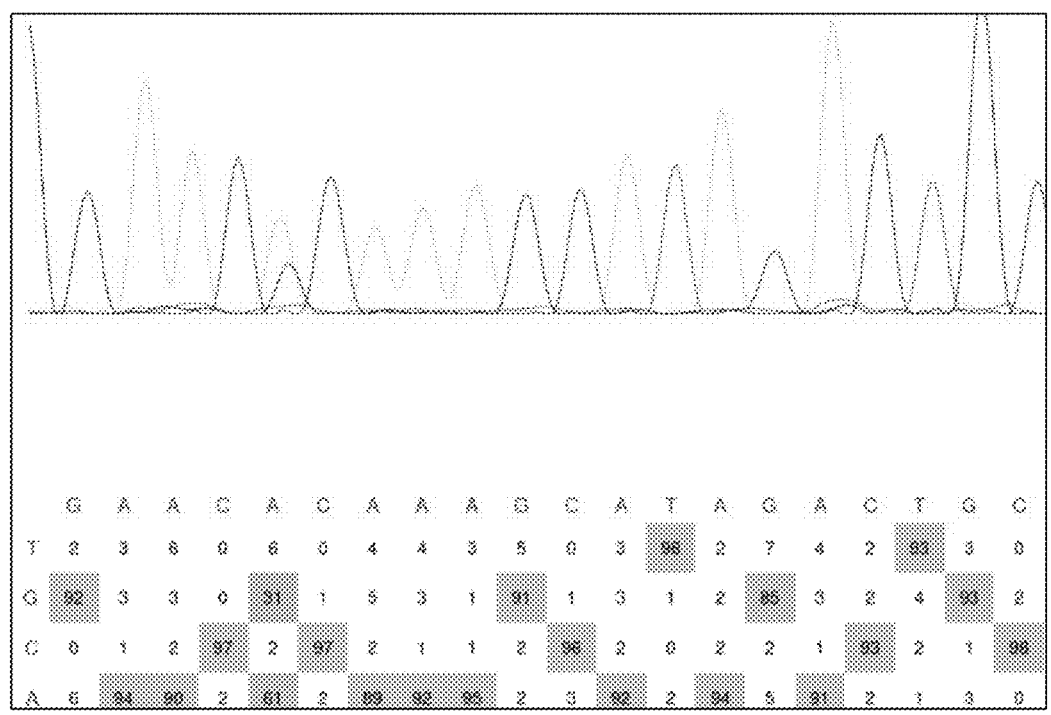

FIG. 7 shows the sequencing results after HEK2 gene editing by pX330-ZoTadA1.0-HeK2 in 293T cells. Results show editing effects, and the editing window was position 5. The data in the lower table showed the values at each nucleotide site, with the value below 10 treated as noise. The A→G editing efficiency was about 31% at position 5.

Figure 8:
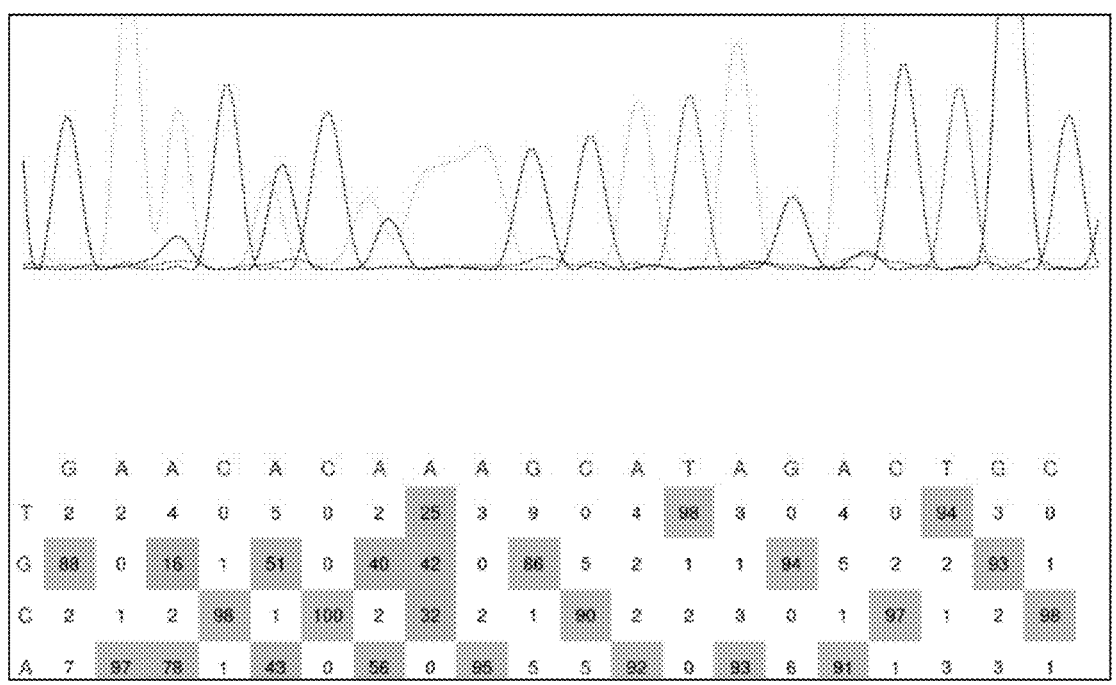

FIG. 8 shows the sequencing results after HEK2 gene editing by pX330-ErTadA1.0-HEK2 in 293T cells. Results show editing effects, and the editing window was position 3, 5, 7 and 8. The data in the lower table showed the values at each nucleotide site, with the value below 10 treated as noise. The A→G editing efficiency was about 16% at position 3, about 51% at position 5, about 40% at position 7, and about 42% at position 8. Positions 7, 8, and 9 correspond all to adenine A and sequencing map showed obvious adenine A overlapping peaks and no peak for other bases. The values generated by the software were interfered by the overlapping peaks and showed the existence of other bases. This was an error generated by the software and the sequencing map shall prevail. From the sequencing map, A8 position had the highest editing efficiency.

Figure 9:
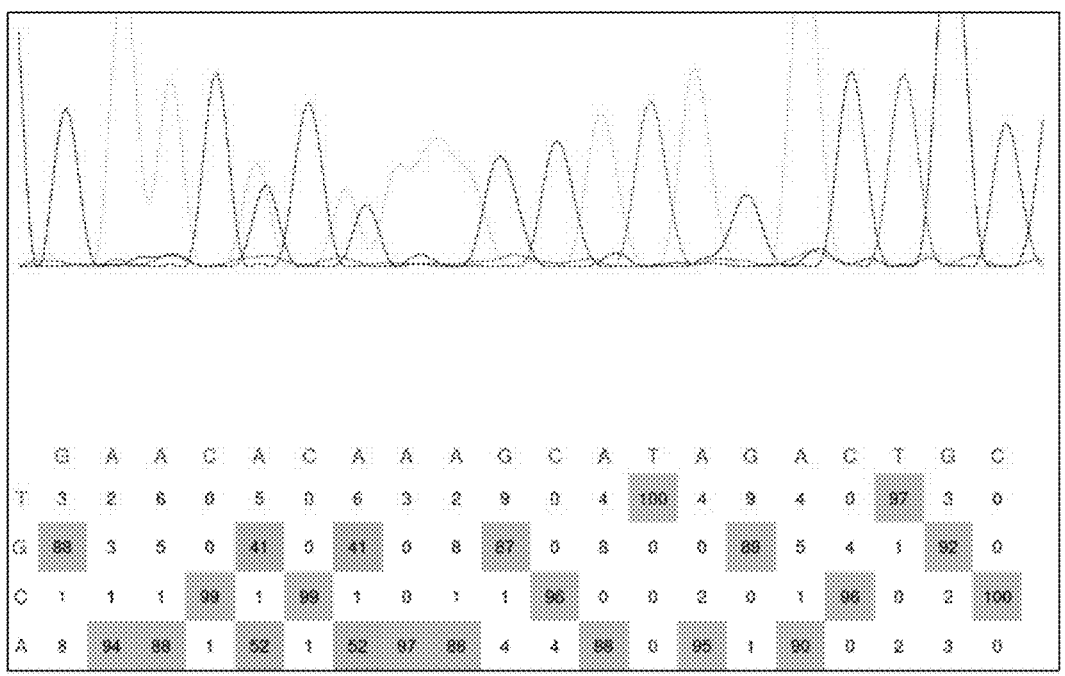

FIG. 9 shows the sequencing results after HEK2 gene editing by pX330-TadA-8e-HeK2 in 293T cells. Results show editing effects, and the editing window was positions 5 and 7. The data in the lower table showed the values at each nucleotide site, with the value below 10 treated as noise. The A→G editing efficiency was about 41% at position 5 and about 41% at position 7.

Figure 10:
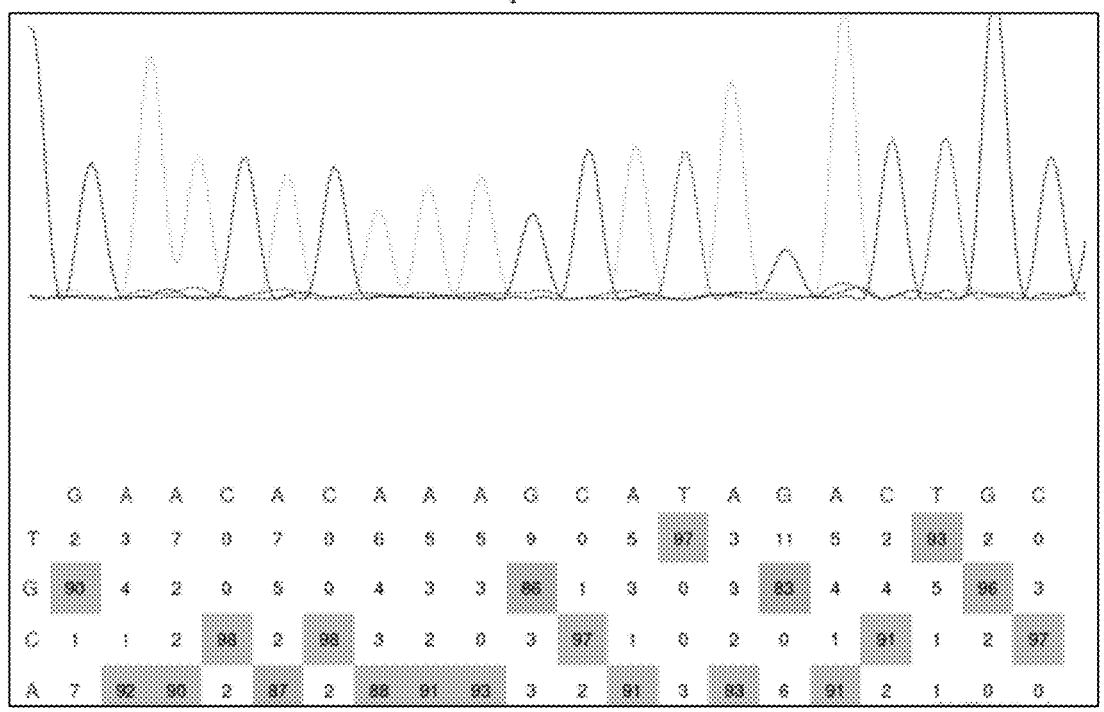

FIG. 10 shows the sequencing results after HEK2 gene editing by pX330 blank vector in 293T cells. Results show no editing effect.

Figure 11:
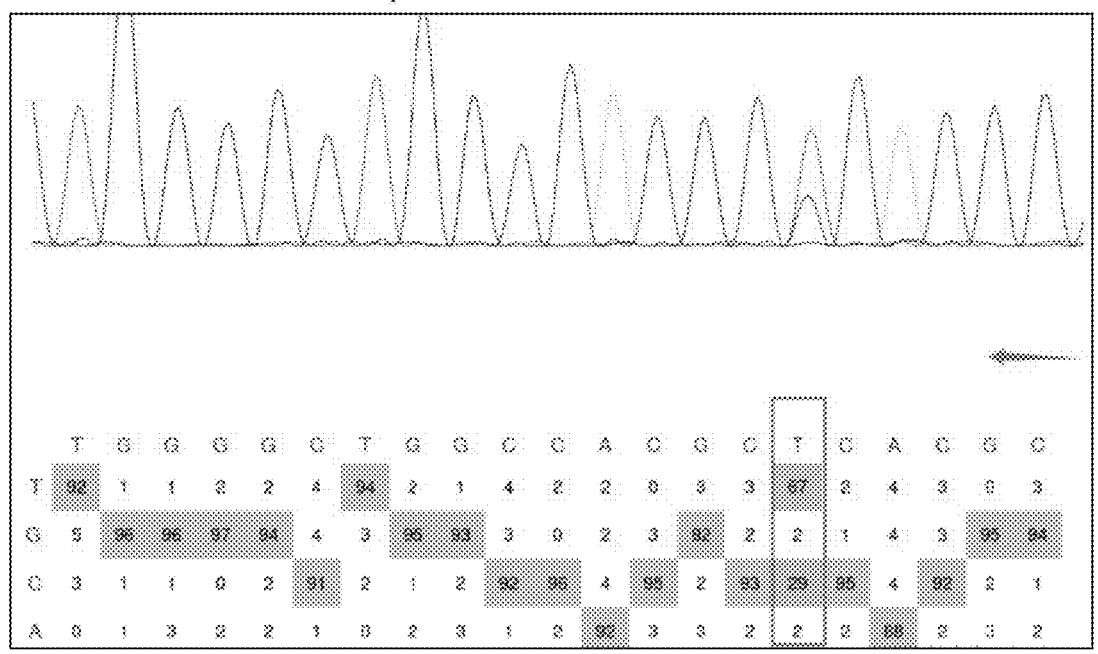
FIGS. 11-15 are sequencing results after p992L gene editing by various adenosine base editors in 293T cells. Sequences shown in the upper panel, are all SEQ ID NO: 81.

FIG. 11 shows the sequencing results after p992L gene editing by pX330-MaTadA1.0-P992L in 293T cells. Results show editing effects with overlapping peaks. The A→G editing efficiency was about 29% at position 6. The sequencing results were shown as the antisense strand of sgRNA (3' to 5') due to primer reasons (same hereinafter).

Figure 12:
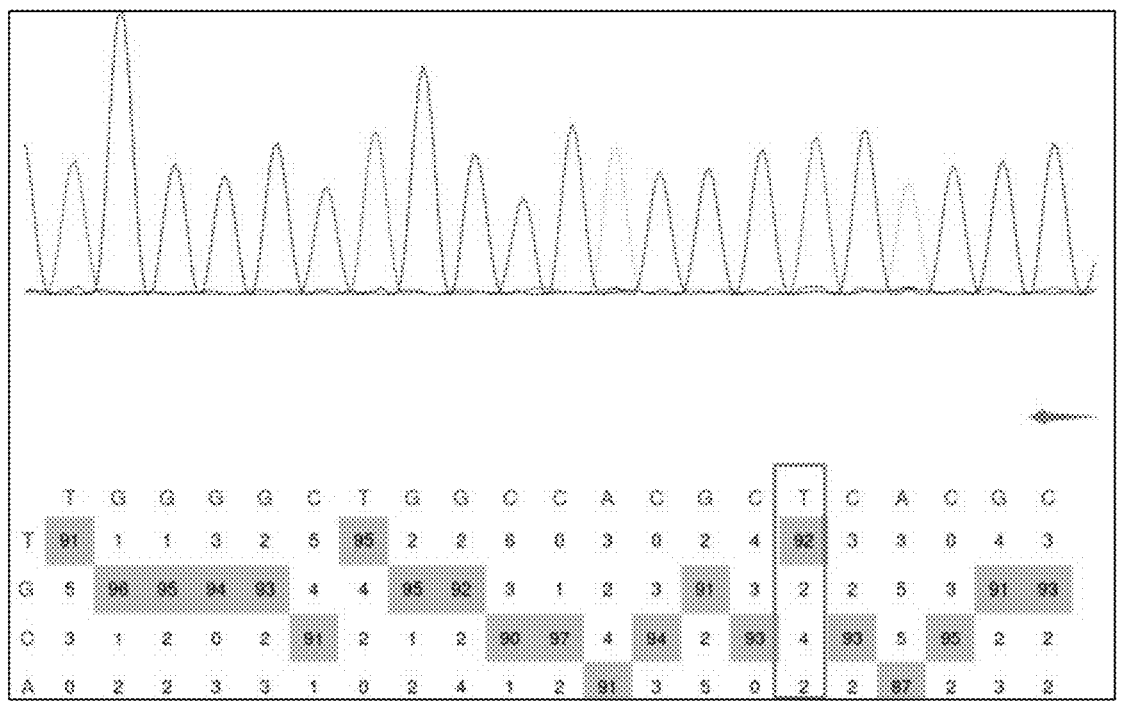

FIG. 12 shows the sequencing results after p992L gene editing by pX330-MaTadA-WT-nCas9-P992L in 293T cells. Results show no editing effects (without overlapping peak).

Figure 13:
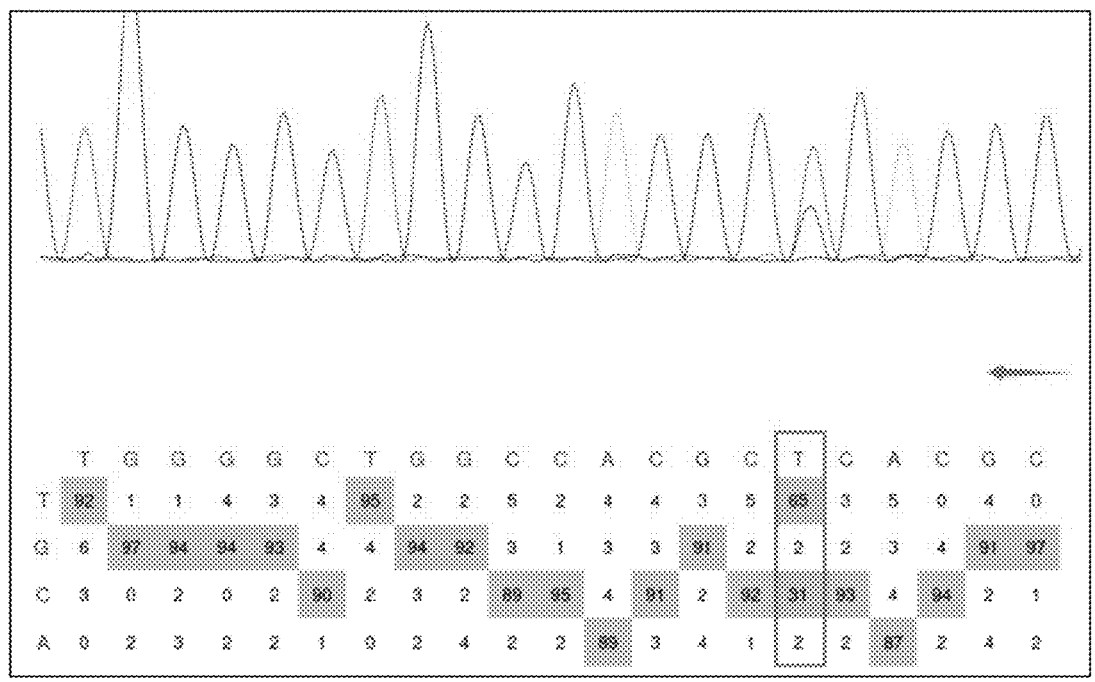

FIG. 13 shows the sequencing results after p992L gene editing by pX330-ErTadA1.0-nCas9-P992L in 293T cells. Results show editing effects with overlapping peaks. The A→G editing efficiency was about 31% at position 6.

Figure 14:
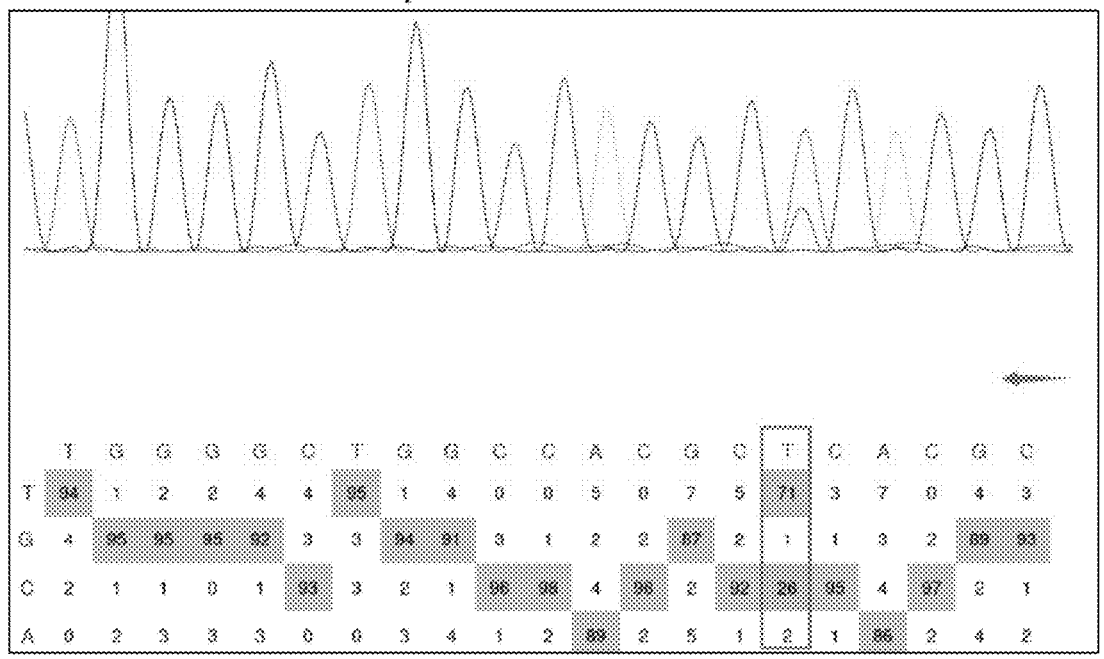

FIG. 14 shows the sequencing results after p992L gene editing by pX330-TadA-8e-P992L in 293T cells. Results show editing effects. The A→G editing efficiency was about 26% at position 6, lower than that was obtained in HKE2 gene editing at the same site.

Figure 15:
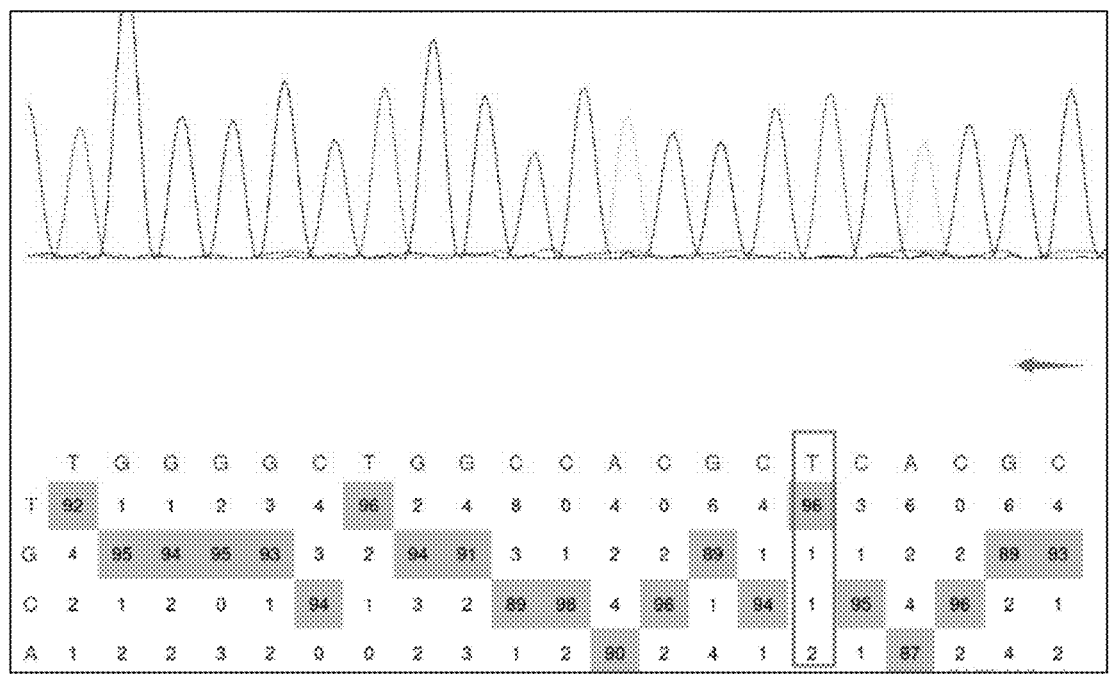

FIG. 15 shows the sequencing results after p992L gene editing by pX330 blank vector in 293T cells. Results show no editing effects.

What is claimed is:

1. An adenosine deaminase, comprising an amino acid sequence having about 85% to about 99.5% sequence identity to SEQ ID NO: 1 and having an amino acid substitution at each of residues E168 and E169, relative to the sequence shown in SEQ ID NO: 1.

2. The adenosine deaminase according to claim 1, wherein the amino acid sequence having about 85% to about 99.5% sequence identity to SEQ ID NO: 1 further includes an amino acid substitution at one or more residues selected from the group consisting of W23, Y36, P48, H51, L84, A106, D108, V109, K110, T111, D119, G122, H123, S146, F149, R152, H156, and K157, relative to the sequence SEQ ID NO: 1.

3. The adenosine deaminase according to claim 1, wherein the amino acid sequence having about 85% to about 99.5% sequence identity to SEQ ID NO: 1 further includes an amino acid substitution at each one of the residues of W23, Y36, P48, H51, L84, A106, D108, V109, T111, D119, G122, H123, S146, F149, R152, H156, and K157, relative to the sequence SEQ ID NO: 1.

4. The adenosine deaminase according to claim 3, wherein:
    (a) the substitution at W23 is selected from the group consisting of W23R, W23K and 23H;
    (b) the substitution at Y36 is selected from the group consisting of Y36L, Y36V, Y36I and Y36P;
    (c) the substitution at P48 is P48A;
    (d) the substitution at H51 is selected from the group consisting of H51L, H51V, H51I and H51P;
    (e) the substitution at L84 is selected from the group consisting of L84F, L84W and L84Y;
    (f) the substitution at A106 is selected from the group consisting of A106V, A106I, A106L and A106P;
    (g) the substitution at D108 is D108N;
    (h) the substitution at V109 is V109S;
    (i) the substitution at T111 is selected from the group consisting of T111R, T111K and T111H;
    (j) the substitution at D119 is selected from the group consisting of D119N, D119R and D119Q;
    (k) the substitution at G122 is G122N;
    (l) the substitution at H123 is H123Y;
    (m) the substitution at S146 is S146C;
    (n) the substitution at F149 is selected from the group consisting of F149Y and F149H;
    (o) the substitution at R152 is R152P;
    (p) the substitution at H156 is selected from the group consisting of H156F, H156W and H156Y;
    (q) the substitution at K157 is K157N;
    (r) the substitution at E168 is E168I; and
    (s) the substitution at E169 is E169N.

5. The adenosine deaminase according to claim 4, wherein the adenosine deaminase comprises an amino acid sequence selected from the group consisting of SEQ ID NOs: 2 to 10 or an amino acid sequence having at least about 95% sequence identity to the amino acid sequence of any of SEQ ID NOs: 2 to 10, with the proviso that the adenosine deaminase does not include the amino acid sequence shown in SEQ ID NO: 1.

6. The adenosine deaminase according to claim 5, wherein the adenosine deaminase comprises:
    (i) the amino acid sequence of SEQ ID NO: 2 or an amino acid sequence having at least about 95% sequence identity to the amino acid sequence shown in SEQ ID NO: 2; or
    (ii) the amino acid sequence of SEQ ID NO: 6 or an amino acid sequence having at least about 95% sequence identity to SEQ ID NO: 6;
    with the proviso that the adenosine deaminase does not include the amino acid sequence SEQ ID NO: 1.

7. The adenosine deaminase according to claim 1, wherein the substitution at residue E168 is E168I and the substitution at residue E169 is E169N.

8. A base editor comprising an adenosine deaminase according to claim 1, further comprising a cytidine deaminase domain.

9. A base editor comprising a first adenosine deaminase according to claim 1, further comprising a second adenosine deaminase domain that is the same as or different from the first adenosine deaminase.

10. A base editor comprising an adenosine deaminase according to claim 1, further comprising one or more nuclear localization sequences.

11. A base editor comprising an adenosine deaminase according to claim 1, further comprising a programmable DNA binding protein domain selected from Cas9 or Cas12 protein domains.

12. The base editor according to claim 11, wherein the programmable DNA binding protein domain is a dCas9 domain or an nCas9 domain.

13. The base editor according to claim 12, wherein the base editor comprises an architecture selected from the group consisting of:
    NH$_2$-[NLS]-[MaTadA1.0]-[dCas9/nCas9]-[NLS]-COOH;
    NH$_2$-[NLS]-[dCas9/nCas9]-[MaTadA1.0]-[NLS]-COOH;
    NH$_2$-[NLS]-[MaTadA1.0-1]-[dCas9/nCas9]-[NLS]-COOH;
    NH$_2$-[NLS]-[dCas9/nCas9]-[MaTadA1.0-1]-[NLS]-COOH;
    NH$_2$-[NLS]-[MaTadA1.0-2]-[dCas9/nCas9]-[NLS]-COOH;
    NH$_2$-[NLS]-[dCas9/nCas9]-[MaTadA1.0-2]-[NLS]-COOH;

NH$_2$-[NLS]-[MaTadA1.0-3]-[dCas9/nCas9]-[NLS]-COOH;

NH$_2$-[NLS]-[dCas9/nCas9]-[MaTadA1.0-3]-[NLS]-COOH;

NH$_2$-[NLS]-[MaTadA1.1]-[dCas9/nCas9]-[NLS]-COOH;

NH$_2$-[NLS]-[dCas9/nCas9]-[MaTadA1.1]-[NLS]-COOH;

NH$_2$-[NLS]-[MaTadA1.2]-[dCas9/nCas9]-[NLS]-COOH;

NH$_2$-[NLS]-[dCas9/nCas9]-[MaTadA1.2]-[NLS]-COOH;

NH$_2$-[NLS]-[MaTadA1.3]-[dCas9/nCas9]-[NLS]-COOH;

NH$_2$-[NLS]-[dCas9/nCas9]-[MaTadA1.3]-[NLS]-COOH;

NH$_2$-[NLS]-[MaTadA1.4]-[dCas9/nCas9]-[NLS]-COOH;

NH$_2$-[NLS]-[dCas9/nCas9]-[MaTadA1.4]-[NLS]-COOH;

NH$_2$-[NLS]-[MaTadA1.5]-[dCas9/nCas9]-[NLS]-COOH; and

NH$_2$-[NLS]-[dCas9/nCas9]-[MaTadA1.5]-[NLS]-COOH.

14. A complex comprising the base editor according to claim 11 and a guide RNA, wherein the guide RNA is linked to the programmable DNA binding protein domain of the base editor.

15. A base editor comprising an adenosine deaminase according to claim 1, wherein the base editor comprises an amino acid sequence selected from the group consisting of SEQ ID NOs: 46 to 48.

16. A polynucleotide encoding an adenosine deaminase comprising an amino acid sequence having about 85% to about 99.5% sequence identity to SEQ ID NO: 1 and having an amino acid substitution at each of residues E168 and E169, relative to the sequence SEQ ID NO: 1.

17. A vector comprising the polynucleotide according to claim 16.

18. A pharmaceutical composition comprising the vector of claim 17 and a pharmaceutically acceptable carrier.

19. A cell comprising the vector according to claim 17.

20. A pharmaceutical composition comprising the cell of claim 19 and a pharmaceutically acceptable carrier.

21. A pharmaceutical composition comprising a base editor comprising an adenosine deaminase according to claim 1 or a complex comprising the base editor comprising an adenosine deaminase according to claim 1 and a guide RNA; and a pharmaceutically acceptable carrier.

* * * * *